United States Patent
Flavell et al.

(10) Patent No.: US 10,433,527 B2
(45) Date of Patent: *Oct. 8, 2019

(54) GENETICALLY MODIFIED NON-HUMAN ANIMALS AND METHODS OF USE THEREOF

(71) Applicants: Regeneron Pharmaceuticals, Inc., Tarrytown, NY (US); Yale University, New Haven, CT (US); Institute for Research in Biomedicine (IRB), Bellinzona (CH)

(72) Inventors: Richard Flavell, Guilford, CT (US); Markus Manz, Zollikon (CH); Anthony Rongvaux, New Haven, CT (US); Till Strowig, Braunschweig (DE); Tim Willinger, Ultran (SE); Andrew J. Murphy, Croton-on-Hudson, NY (US); Sean Stevens, Del Mar, CA (US); George Yancopoulos, Yorktown Heights, NY (US)

(73) Assignees: Regeneron Pharmaceuticals, Inc., Tarrytown, NY (US); Yale University, New Haven, CT (US); Institute for Research in Biomedicine (IRB), Bellinzona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,602

(22) Filed: May 15, 2018

(65) Prior Publication Data
US 2019/0082663 A1 Mar. 21, 2019

Related U.S. Application Data

(63) Continuation of application No. 15/598,080, filed on May 17, 2017, now abandoned, which is a continuation of application No. 14/420,318, filed as application No. PCT/US2013/058448 on Sep. 6, 2013, now Pat. No. 9,820,476.

(60) Provisional application No. 61/698,002, filed on Sep. 7, 2012, provisional application No. 61/775,171, filed on Mar. 8, 2013.

(51) Int. Cl.
| A01K 67/027 | (2006.01) |
| C12N 5/0789 | (2010.01) |
| C12N 15/87 | (2006.01) |

(52) U.S. Cl.
CPC ...... *A01K 67/0278* (2013.01); *A01K 67/0271* (2013.01); *C12N 15/87* (2013.01); *A01K 2207/12* (2013.01); *A01K 2207/15* (2013.01); *A01K 2217/072* (2013.01); *A01K 2217/15* (2013.01); *A01K 2227/105* (2013.01); *A01K 2267/0331* (2013.01); *A01K 2267/0381* (2013.01); *A01K 2267/0387* (2013.01)

(58) Field of Classification Search
CPC ............ A01K 67/0278; A01K 2207/15; A01K 2217/072; A01K 2227/105; A01K 2267/0331; A01K 2267/0387; A01K 67/0271; A01K 2207/12; A01K 2217/15; C12N 15/87
USPC .................................. 800/18, 13; 424/93.1
See application file for complete search history.

(56) References Cited

U.S. PATENT DOCUMENTS

| 4,736,866 | A | 4/1988 | Leder et al. |
| 4,870,009 | A | 9/1989 | Evans et al. |
| 5,222,982 | A | 6/1993 | Ommaya |
| 5,385,582 | A | 1/1995 | Ommaya |
| 5,573,930 | A | 11/1996 | Ladner et al. |
| 5,583,278 | A | 12/1996 | Alt et al. |
| 5,633,426 | A | 5/1997 | Namikawa et al. |
| 5,652,373 | A | 7/1997 | Reisner et al. |
| 5,663,481 | A | 9/1997 | Gallinger et al. |
| 5,681,729 | A | 10/1997 | Kudo et al. |
| 5,709,843 | A | 1/1998 | Reisner et al. |
| 5,750,826 | A | 5/1998 | Borkowski et al. |
| 5,849,288 | A | 12/1998 | Reisner et al. |
| 5,866,757 | A | 2/1999 | Reisner et al. |
| 6,018,096 | A | 1/2000 | Keating et al. |
| 6,353,150 | B1 | 3/2002 | Dick et al. |
| 6,455,756 | B1 | 9/2002 | Chen et al. |
| 6,586,251 | B2 | 7/2003 | Economides et al. |
| 7,273,753 | B2 | 9/2007 | Crawford et al. |
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 7,759,541 | B2 | 7/2010 | Wolf et al. |
| 8,541,646 | B2 | 9/2013 | Stevens et al. |
| 8,692,052 | B2 | 4/2014 | Stevens et al. |
| 8,847,004 | B2 | 9/2014 | Murphy et al. |
| 8,878,001 | B2 | 11/2014 | Wang et al. |

(Continued)

FOREIGN PATENT DOCUMENTS

| CN | 101250553 | 8/2008 |
| EP | 0322240 | 6/1989 |

(Continued)

OTHER PUBLICATIONS

U.S. Appl. No. 15/954,450, filed Apr. 16, 2018, Herndler-Brandstetter, Dietmar, et al.
Ashizawa, et al (2017) "Antitumor Effect of Programmed Death-1 (PD-1) Blockade in Humanized the NOG-MHC Double Knockout Mouse"; *Clin Cancer Res*; 23(1); pp. 149-158.
Chang, et al (2015) "Anti-CCR4 monoclonal antibody enhances antitumor immunity by modulating tumor-infiltrating Tregs in an ovarian cancer xenograft humanized mouse model"; *Oncoimmunology* 5(3): e1090075. 14 pages.

(Continued)

*Primary Examiner* — Anne Marie S Wehbe
(74) *Attorney, Agent, or Firm* — Tor Smeland; Ilona Gont; Michael B. Rubin

(57) ABSTRACT

The invention relates generally to genetically modified non-human animals expressing human polypeptides and their methods of use.

12 Claims, 36 Drawing Sheets

(56) References Cited

U.S. PATENT DOCUMENTS

| | | | |
|---|---|---|---|
| 9,127,292 B2 | 9/2015 | Murphy et al. | |
| 9,155,290 B2 | 10/2015 | Rojas | |
| 9,193,977 B2 | 11/2015 | Murphy et al. | |
| 9,301,509 B2 | 4/2016 | Stevens et al. | |
| 9,402,377 B2 | 8/2016 | Flavell | |
| 9,462,794 B2 | 10/2016 | Murphy et al. | |
| 9,554,563 B2 | 1/2017 | Stevens et al. | |
| 9,655,352 B2 | 5/2017 | Stevens et al. | |
| 9,820,476 B2* | 11/2017 | Flavell | A01K 67/0271 |
| 9,901,082 B2 | 2/2018 | Flavell et al. | |
| 9,986,724 B2 | 6/2018 | Flavell et al. | |
| 2002/0037523 A1 | 3/2002 | Ruben et al. | |
| 2003/0028911 A1 | 2/2003 | Huang et al. | |
| 2005/0208474 A1 | 9/2005 | Lau et al. | |
| 2007/0254842 A1 | 11/2007 | Bankiewicz | |
| 2008/0081064 A1 | 4/2008 | Jelle et al. | |
| 2008/0311095 A1 | 12/2008 | Holmes et al. | |
| 2009/0196903 A1 | 8/2009 | Kliman | |
| 2011/0200982 A1 | 8/2011 | Stevens et al. | |
| 2012/0157667 A1 | 6/2012 | Chen | |
| 2013/0022996 A1 | 1/2013 | Stevens et al. | |
| 2013/0024957 A1 | 1/2013 | Stevens et al. | |
| 2013/0042330 A1 | 2/2013 | Murphy et al. | |
| 2013/0117873 A1 | 5/2013 | Wang et al. | |
| 2014/0090095 A1 | 3/2014 | Stevens et al. | |
| 2014/0134662 A1 | 5/2014 | Flavell et al. | |
| 2015/0047061 A1 | 2/2015 | Murphy et al. | |
| 2015/0089678 A1 | 3/2015 | Murphy et al. | |
| 2015/0089679 A1 | 3/2015 | Murphy et al. | |
| 2015/0208622 A1 | 7/2015 | Flavell et al. | |
| 2015/0327524 A1 | 11/2015 | Murphy et al. | |
| 2016/0050896 A1 | 10/2016 | Murphy et al. | |
| 2016/0295844 A1 | 10/2016 | Herndler-Brandstetter et al. | |
| 2016/0366862 A1 | 12/2016 | Flavell et al. | |
| 2016/0374321 A1 | 12/2016 | Murphy et al. | |
| 2017/0172121 A1 | 6/2017 | Murphy et al. | |
| 2017/0273285 A1 | 9/2017 | Murphy et al. | |
| 2018/0020647 A1 | 1/2018 | Flavell et al. | |
| 2018/0049413 A1 | 2/2018 | Flavell et al. | |

FOREIGN PATENT DOCUMENTS

| | | |
|---|---|---|
| EP | 0438053 | 7/1991 |
| EP | 0517199 | 12/1992 |
| EP | 1452093 | 9/2004 |
| GB | 2434578 A | 8/2007 |
| RU | 2425880 C2 | 8/2011 |
| WO | WO 198803173 | 5/1988 |
| WO | WO 1989012823 | 12/1989 |
| WO | WO 1991016910 | 11/1991 |
| WO | WO 1991018615 | 12/1991 |
| WO | WO 1993005796 | 4/1993 |
| WO | WO 1998044788 | 10/1998 |
| WO | WO 200115521 | 3/2001 |
| WO | WO 2002066630 | 8/2002 |
| WO | WO 2003018744 | 3/2003 |
| WO | WO 2003039232 | 5/2003 |
| WO | WO 2004005496 | 1/2004 |
| WO | WO 2004022738 | 3/2004 |
| WO | WO 2004060052 | 7/2004 |
| WO | WO 2008010100 | 1/2008 |
| WO | WO 2008069659 | 6/2008 |
| WO | WO 2009034328 | 3/2009 |
| WO | WO 2009042917 | 4/2009 |
| WO | WO 2011002727 | 1/2011 |
| WO | WO 2011044050 | 4/2011 |
| WO | WO 2012040207 | 3/2012 |
| WO | WO 2012051572 | 4/2012 |
| WO | WO 2012112544 | 8/2012 |
| WO | WO 2013063556 | 5/2013 |
| WO | WO 2014071397 | 5/2014 |
| WO | WO 2015042557 | 3/2015 |
| WO | WO 2015179317 | 11/2015 |
| WO | WO 2016168212 | 10/2016 |

OTHER PUBLICATIONS

Cuende, et al (2015) "Monoclonal antibodies against GARP/TGF-β1 complexes inhibit the immunosuppressive activity of human regulatory T cells in vivo"; Sci Transl Med. 7(284):284ra56; pp. 1-13.

Das, et al (2016) "Microenvironment-dependent growth of preneoplastic and malignant plasma cells in humanized mice"; Nat Med. 22(11); pp. 1351-1357.

Hayday Adrian and Viney Joanne L.; (2000) "The ins and outs of body surface immunology"; Science 290(5489):97-100.

Hofker Marten H., et al., Transgenic mouse methods and protocols, Methods in molecular biology, vol. 209 (2002-2003), p. 51-58.

Houdebine Louis-Marie (2009) "Methods to Generate Transgenic Animals"; Genetic Engineering in Livestock: New Applications and Interdisciplinary Perspectives; pp. 31-48.

Keefer (2015) "Artificial cloning of domestic animals"; PNAS 112; pp. 8874-8878.

Mcdermott et al. (2010) "Comparison of human cord blood engraftment between immunocompromised mouse strains"; Blood 116(2); pp. 193-200.

Patil et al. (2011) "Transgenic animals and drug development: A review"; Indian Journal of Public Health research & Development, vol. 2, No. 1; pp. 106-109.

Rybchin C. N., "Principles of Genetic Engineering";Saint-Petersburg, Publisher SPbGTU, 2002; p. 411-413.

Sanmamed, et al (2015) "Nivolumab and Urelumab Enhance Antitumor Activity of Human T Lymphocytes Engrafted in Rag2-/-IL2Rγnull Immunodeficient Mice"; Cancer Res. 75(17); pp. 3466-3478.

Sanmamed, et al (2016) "Defining the optimal murine models to investigate immune checkpoint blockers and their combination with other immunotherapies"; Ann Oncol. 27(7); pp. 1190-1198.

Selsby et al (2015) "Porcine Models of Muscular Dystrophy"; ILAR Journal, vol. 56, No. 1; pp. 116-126.

Theocharides et al (2016) "Humanized hemato-lymphoid system mice"; Haematologica. (1); 5-19.

Vudattu, et al (2014) "Humanized mice as a model for aberrant responses in human T cell immunotherapy"; J Immunol. 193(2): pp. 587-596.

Waldron-Lynch, et al. (2012) "Teplizumab induces human gut-tropic regulatory cells in humanized mice and patients"; Sci Transl Med. 4(118):118ra12; pp. 1-12.

Yu et al (2017) "A novel humanized mouse model with significant improvement of class-switched, antigen-specific antibody production"; Blood. 129(8); pp. 959-969.

Brevini, et al. (2010) "No shortcuts to pig embryonic stem cells"; Theriogenology. 74(4); pp. 544-550.

Cao et al. (2009) "Isolation and culture of primary bovine embryonic stem cell colonies by a novel method"; J Exp Zool A Ecol Genet Physiol. 311(5); pp. 368-376.

Paris and Stout (2010) "Equine embryos and embryonic stem cells Defining reliable markers of pluripotency"; Theriogenology 74(4); pp. 516-524.

Abadie V., et al; (2014) "IL-15: a central regulator of celiac disease immunopathology"; Immunol Rev. 260(1):221-34.

Abboud et al., (2003) "Analysis of the Mouse CSF-1 Gene Promoter in a Transgenic Mouse Model" The Journal of Histochemistry & Cytochemistry, 51(7):941-949.

Appenheir et al (2007) "Conservation of IL-6 trans-signaling mechanisms controlling L-selectin adhesion by fever-range thermal stress"; Eur J Immunol. 37(10):2856-67.

Alves et al.; (2009) "Characterization of the thymic IL-7 niche in vivo"; Proceedings of the National Academy of Sciences, 106(5); pp. 1512-1517.

Angulo-Barturen Inigo, et al; "A Murine Model of falciparum-Malaria by in Vivo Selection of Competent Strains in Non-Myelodepleted Mice Engrafted with Human Erythrocytes"; PLoS ONE, vol. 3. No. 5; May 2008, pp. 1-14; XP055166984

(56) References Cited

OTHER PUBLICATIONS

Arranz Eduardo and Garrote Jose A. (2011) "IL-15 modulates the effect of retinoic acid, promoting inflammation rather than oral tolerance to dietary antigen"; *Expert Rev. Gastroenterol. Hepatol. 5(3)*; pp. 315-317.
Auffray et al., (2009), "Blood monocytes: development, heterogeneity, and relationship with dendritic cells"; *Annual review of immunology 27*, 669-692.
Badell et al. (2000) "Human malaria in immunocompromised mice: an in vivo model to study defense mechanisms against Plasmodium falciparum"; *JEM 192(11)*: pp. 1653-1659.
Baenziger et al., (2006), "Disseminated and Sustained HIV infection in $CD34^{30}$ Cord Blood Cell-Transplanted Rag2-/-γc-/-Mice"; *Proc Natl Acad Sci USA 103*: pp. 15951-15956.
Bartley, T.D. et al. (1994) "Identification and cloning of a megakaryocyte growth and development factor that is a ligand for the cytokine receptor Mpl"; *Cell 77*: pp. 1117-1124. (Abstract).
Becker et al., (2010), "Generation of Human Antigen-Specific Monoclonal IgM Antibodies Using Vaccinated Human Immune System Mice"; *PLoS ONE 5(10)*; pp. 1-10.
Bergsagel et al.; (2005); "Cyclin D dysregulation: an early and unifying pathogenic event in multiple myeloma"; *Blood 106*: pp. 296-303.
Bernard, et al; "Establishing humanized mice using stem cells. maximizing the potential"; *Clinical & Experimental Immunology* vol. 152, Issue 3, (Jun. 2008); pp. 406-414.
Biedzka-Sarek; et al. "How to outwit the enemy: dendritic cells face Salmonella"; *APMIS 114(9)*; (Sep. 2006): pp. 589-600.
Billerbeck, et al (2011) "Development of human CD4+FoxP3+ regulatory T cells in human stem cell factor-, granulocyte-macrophage colony-stimulating factor-, and interleukin-3-expressing NOD-SCID IL2Rγ(null) humanized mice"; *Blood 117(11)*; pp. 3076-3086.
Bingle et al., (2002), "The role of tumour-associated macrophages in tumour progression: implications for new anticancer therapies"; *T Journal of pathology 196*: pp. 254-265.
Bird et al., (1988) "Single-Chain Antigen-Binding Proteins"; *Science 242*: pp. 423-426.
Bock; et al. "Improved Engraftment of Humanized Hematopoeitic Cells in Severe Combined Immunodeficient (SCID) Mice Carrying Human Cytokine Transgenes"; *Journal of Exp. Med. 182*; (Dec. 1995); pp. 2037-2043.
Bosma et al. (1989), "The mouse mutation severe combined immune deficiency (scid) is on chromosome 16"; *Immunogenetics 29*: pp. 54-56.
Brehm; et al. (2010) "Parameters for establishing humanized mouse models to study human immunity: Analysis of human hematopoeitic stem cell engraftment in three immunodeficient strains of mice bearing the IL2rγ null mutation"; *Clinical Immunology 135*; pp. 84-98.
Brehm et al., (2012), "Engraftment of human HSCs in nonirradiated newborn NOD-scid IL2rγ$^{null}$ mice is enhanced by transgenic expression of membrane-bound human SCF"; *Blood 119*: pp. 2778-2788.
Burger et al., (2001) "Gp130 and ras mediated signaling in human plasma cell line INA-6: a cytokine-regulated tumor model for plasmacytoma"; *Hematol J*, 2(1): pp. 42-53.
Campbell et al. (1993) "Neurologic disease induced in transgenic mice by cerebral overexpression of interleukin 6"; *Proc. Natl. Acad. Sci. USA*, 90: pp. 10061-10065.
Calvi; et al. "Osteoblastic cells regulate the haematopoietic stem cell niche"; *Nature 425* (Oct. 2003); pp. 841-846.
Carstea, et al. (2009) "Germline competence of mouse ES and iPS cell lines: Chimera technologies and genetic background"; *World Journals of Stem Cells*, vol. 1, No. 1; pp. 22-29.
Chen et al., "Expression of human cytokines dramatically improves reconstitution of specific human-blood lineage cells in humanized mice"; *PNAS 106(51)*: (Dec. 22, 2009) pp. 21783-21788.
Chen et al. (2012) "Human extramedullary bone marrow in mice: a novel in vivo model of genetically controlled hematopoietic microenvironment"; *Blood 119(21)*; pp. 4971-4980.

Cheng et al. (2010)"Therapeutic Antibodies Targeting CSF1 Impede Macrophage Recruitment in a Xenograft Model of Tenosynovial Giant Cell Tumor"; *Sarcoma*, Article ID 174528; pp. 1-7.
Chicha et al. (2005) "Human Adaptive Immune System Rag2-/-γc-/-Mice"; *Annals of NY Academy of Science 104*; pp. 236-243.
Chng et al. (2005) "A validated FISH trisomy index demonstrates the hyperdiploid and nonhyperdiploid dichotomy in MGUS"; *Blood 106(6)*: pp. 2156-2161.
Chow et al., (2011) "Studying the mononuclear phagocyte system in the molecular age" *Nature reviews Immunology 11*: pp. 788-798.
Clark, et al.; "A future for transgenic livestock"; *Natures Reviews*, vol. 4; (Oct. 2003); pp. 825-833.
Cocco; et al. "CD34+ Cord Blood Cell-Transplanted Rag2-/-γc-/-Mice as a Model for Epstein-Barr Virus Infection"; *The American Journal of Pathology 173(5)*: (Nov. 2008); pp. 1369-1378.
Coussens et al. (2013) "Neutralizing tumor-promoting chronic inflammation: a magic bullet?"; *Science 339*: pp. 286-291.
Cros et al. (2010) "Human $CD14^{dim}$ Monocytes Patrol and Sense Nucleic Acids and Viruses via TLR7 and TLR8 Receptors"; *Immunity 33*: pp. 375-386.
Dai et al.; "Incomplete restoration of colony-stimulating factor 1 (CSF-1) function in CSF-1-deficient Csflop/Csflop mice by transgenic expression of cell surface CSF-1"; *Blood 103(3)*:1114-1123 (Feb. 1, 2004).
Danos et al. (1988) "Safe and efficient generation of recombinant retroviruses with amphotropic and ecotropic host ranges"; *PNAS 85(17)*: pp. 6460-6464.
Dao; et al. (1999) "Immunodeficient mice as models of human hematopoietic stem cell engraftment"; *Current Opinion in Immunol 11*; 532-537.
Denning, et al (2001) "Deletion of the alpha(1,3)galactosyl transferase (GGTA1) gene and the prion protein (PrP) gene in sheep"; *Nat Biotech*; 19; pp. 559-562.
Dennis Melvin B. (2002) "Welfare issues of genetically modified animals"; *ILAR Journal*, vol. 43, No. 2; pp. 100-109.
Denton PW, et al. (2012) "IL-2 receptor γ-chain molecule is critical for intestinal T-cell reconstitution in humanized mice"; *Mucosal Immunol*; 5(5); pp. 555-566.
Depaolo, et al. (2011) "Co-adjuvant effects of retinoic acid and IL-15 induce inflammatory immunity to dietary antigens"; *Nature. 471*; pp. 220-224.
De Raeve and Vanderkerken, (2005), "The role of the bone marrow microenvironment in multiple myeloma"; *Histol Histopathol. 20*: pp. 1227-1250.
De Sauvage, F.J. et al. (1994) "Stimulation of megakaryocytopoiesis and thrombopoiesis by the c-Mpl ligand"; *Nature 369*: pp. 533-538.
Dewan et al., (2004) "Prompt tumor formation and maintenance of constitutive NF-κB activity of multiple myeloma cells in NOD/SCID/γc$^{null}$ mice"; *Cancer Sci. 95*; pp. 564-568.
Dhodapkar (2009) "Myeloid neighborhood in myeloma: Cancer's underbelly" *Am J Hematol. 84*: pp. 395-396.
Diminici et al. (2006) "Minimal criteria for defining multipotent mesenchymal stromal cells, The International Society for Cellular Therapy position statement"; *Cytotherapy 8*: pp. 315-317.
Drake, et al. (2012) "Engineering humanized mice for improved hematopoietic reconstitution"; *Cell Mol Immunol. 9(3)*; pp. 215-224.
Egeblad et al., (2010), "Tumors as organs: complex tissues that interface with the entire Organism"; *Developmental Cell 18*: pp. 884-901.
Eisenbarth et al.; "Development and Characterization of a Human IL-7 Transgenic Humanized Mouse Model,"; *iwhm2, 2nd International Workshop on Humanized Mice, Program & Abstract Book*; Sint Olofskapel, Amsterdam, The Netherlands, Apr. 3-6, 2009, Abstract #19.
El-Ad et al. (2013) "viSNE enables visualization of high dimensional single-cell data and reveals phenotypic heterogeneity of leukemia"; *Nat. Biotechnol. 31(6)*;pp. 545-552.
Epstein et al., (2005), "The SCID-hu myeloma model"; *Methods Mol Med*, 113: pp. 183-190.

(56) References Cited

OTHER PUBLICATIONS

Erta M. et al., (2012) "Interleukin-6, a major cytokine in the central nervous system"; *Int J Biol Sci. 8(9)*:1254-66. doi: 10.7150/ijbs. 4679. Epub Oct. 25, 2012.
Extended European Search Report for EP Application No. 16157878.6 dated May 23, 2016.
Fattori, et al., (1994) "Development of Progressive Kidney Damage and Myeloma Kidney in Interleukin-6 Transgenic Mice"; *Blood*, 83(9): pp. 2570-2579.
Fattori et al. (1995) "IL-6 Expression in Neurons of Transgenic Mice Causes Reactive Astrocytosis and Increase in Ramified Microglial Cells but no Neuronal Damage"; *European Journal of D Neuroscience*, 7: 2441-2449.
Felix, R. et al. (1990) "Macrophage colony stimulating factor restores IN VIVO bone resorption in the OP/OP osteopetrotic mouse"; *Endocrinology 127*: pp. 2592-2594.
Fisher et al.; (1993) "Lymphoprolierative Disorders in an IL-7 Transgenic Mouse Line"; *Leukemia*, 7(2): pp. 566-568.
Flavell, Richard A. "Tissue-resident T cells in a novel humanized mouse model" Presentation: CSH Meeting, Apr. 16, 2015; 23 pages.
Fonseca et al., (2002), "Genomic abnormalities in monoclonal gammopathy of undetermined significance" *Blood 100*: pp. 1417-1424.
Foss et al. (1995) "Frequent Expression of IL-7 Gene Transcripts in Tumor Cells of Classical Hodgkin's Disease"; *American Journal of Pathology*, 146(1): pp. 33-39.
Fox, N., et al. (2002) "Thrombopoietin expands hematopoietic stem cells after transplantation"; *J Clin Invest 110*: pp, 389-394.
Freeden Jeffry et al. (1995) "Lymphopenia in Interleukin (IL)-7 Gene-deleted Mice Identifies IL-7 as a Nonredundant Cytokine"; *J. Exp. Med., 181*; pp. 1519-1526.
Fry et al. (2001) "A potential role for interleukin-7 in T-cell homeostasis"; *Blood*, 97: pp. 2983-2990.
Fry et al. (2006) "IL-7 comes of age"; *Blood*, 107(1): pp. 2587-2588.
Fry et al. (2005) "The Many Faces of IL-7: From Lymphopoiesis to Peripheral T Cell Maintenance"; *Journal of Immunology*, 174: pp. 6571-6576.
Fry, et al. (2002) "Interleukin-7: from bench to clinic"; *Blood*, 99(11): pp. 3892-3904.
Fukuchi, Y., et al. (1998) "Cytokine dependent growth of human TF-1 leukemic cell line in human GMCSF and IL-3 producing transgenic SCID mice"; *Leukemia Research*, vol. 22: pp. 837-843.
Galán J.E. & Curtiss, R. (1991) "Distribution of the invA,-B,-C, and -D genes of *S. thyphimurium* among other *Salmonella.* Serovars: invA mutants of *Salmonella typhi* are deficient for entry into mammalian cells"; *Infect. Immun.* 59(9): pp. 2901-2908.
Garcia, Sylvie et al; "Humanized mice: Current states an perspectives"; *Immunology Letters*, Elsevier BV, NL, vol. 146, No. 1-2; Aug. 30, 2012; pp. 1-7; XP002681730.
Geiselhart et al. (2001) "IL-7 Administration Alters the CD4: CDS Ratio, Increases T Cell Numbers, and Increases T Cell Function in the Absence of Activation"; *The Journal of Immunology*, 166: 3019-3027.
Goldman; et al. "BMP4 regulates the hematopoietic stem cell niche"; *Blood 114(20)*; (Nov. 2009):4393-4401.
Goldman, et al. (2004) "Transgenic animals in medicine: integration and expression of foreign genes, theoretical and applied aspects"; *Med Sci Monit*, vol. 10, No. 11; pp. RA274-RA285.
Goodwin et al. (1989) "Human interleukin 7: Molecular cloning and growth factor activity on human and murine B-lineage cells"; *Proc. Natl. Acad. Sci. USA*, 86: pp. 302-306.
Gorantla; et al. "Human Immunodeficiency Virus Type 1 Pathobiology Studied in Humanized BALB/c-Rag2-/-Yc-/- Mice": *Journal of Virology 81(6)*: (Mar. 2007), pp. 2700-2712.
Goya et al. (2003) "Sustained interleukin-6 signalling leads to the development of lymphoid organ-like structures in the lung"; *Journal of Pathology*, 200: pp. 82-87.
Greenblatt, et al. (2012) "Graft versus host disease in the bone marrow, liver and thymus humanized mouse model"; *PLoS One 7(9)*; e44664.
Greiner; et al. "Improved Engraftment of Human Spleen Cells in NOD/LtSz-scid/scid Mice as Compared with C. B-17-scid/scid Mice"; *American Journal of Pathology 146(4)*: (Apr. 1995), pp. 888-902.
Groen, R. W. J., et al; "Reconstructing the human hematopoietic niche in immunodeficient mice: opportunities for studying primary multiple myeloma"; *BLOOD*, vol. 120, No. 3, May 31, 2012; pp. e9-e16, XP055113167.
Guimond et al. (2005) "Cytokine Signals in T-Cell Homeostasis"; *J. Immunother*, 28; pp. 289-294.
Haley, (2003), "Species differences in the structure and function of the immune System"; *Toxicology 188*: pp. 49-71.
Hao et al., (2012) "Macrophages in tumor microenvironments and the progression of tumors"; *Clinical & developmental immunology*: 948098. 11 pages.
Hayakawa J., et al, (2009), "Busulfan produces efficient human cell engraftment in NOD/LtSz-Scid IL2Rgamma(null) mice"; *Stem Cells*, 27(1): pp. 175-182.
Heinrich et al. (1990) "Interleukin-6 and the acute phase response"; *Biochem. J. 265*: pp. 621-636.
Hideshima et al., (2007), "Understanding multiple myeloma pathogenesis in the bone marrow to identify new therapeutic targets"; *Nat Rev Cancer. 7*: pp. 585-598.
Hiramatsu, Hidefumi, et al. (2003) "Complete reconstitution of human lymphocytes from cord blood CD34+ cells using the NOD/SCID/γcnull mice model"; *Blood*, vol. 102, No. 3; pp. 873-880.
Hirano et al. (1985) "Purification to homogeneity and characterization of human B-cell differentiation factor (BCDF or BSFp-2)"; *Proc. Natl. Acad. Sci. USA*, 82: pp. 5490-5494.
Hirano et al. (1986) "Complementary DNA for a novel human interleukin (BSF-2) that induces B lymphocytes to produce immunoglobulin"; *Nature*, 324: pp. 73-76.
Hirano et al. (1990) "Biological and clinical aspects of interleukin 6"; *Immunology*, 11: pp. 443-449.
Hirota et al. (1995) "Continuous activation of gp130, a signal-transducing receptor component for interleukin 6-related cytokines, causes myocardial hypertrophy in mice"; *Proc. Natl. Acad. Sci. D USA*, 92: pp. 4862-4866.
Hofer; et al. "RAG2-/-yc-/-Mice Transplanted with CD34+ Cells from Human Cord Blood Show Low Levels of Intestinal Engraftment and Are Resistant to Rectal Transmission of Human Immunodeficiency Virus", *Journal of Virology 82(24)*: (Dec. 2008), 12145-12153.
Holyoake et al. (1999) "Functional differences between transplantable human hematopoietic stem cells from fetal liver, cord blood, and adult marrow"; *Exp Hematol. 27(9)*: pp. 1418-1427.
Houdebine, Louis-Marie (2007) "Transgenic animal models in biomedical research"; *Methods in Molecular Biology*, vol. 360; pp. 163-202.
Hu, Z. et al; "Macrophages prevent human red blood cell reconstitution in immunodeficient mice"; *BLOOD*, vol. 118, No. 22; Nov. 24, 2011; pp. 5938-5946.
Huo; et al. "Humanized Mouse Model of Cooley's Anemia"; *J. Biol. Chem 284(8)*: (Feb. 2009), 4889-4896.
Huntington et al. (2009) "IL-15 trans-presentation promotes human NK cell development and differentiation in vivo"; *Journal of experimental medicine 206(1)*; pp. 25-34.
Huston et al., (1988), "Protein engineering of antibody binding sites: recovery of specific activity in an anti-digoxin single-chain Fv analogue produced in *Escherichia coli*"; *Proc. Natl. Acad. Sci. USA 85(16)*: pp. 5879-5883.
Inagaki et al. (2000) "SHPS-1 regulates integrin-mediated cytoskeletal reorganization and cell motility"; *EMBO J. 19(24)*; pp. 6721-6731.
Irvine et al., "Colony-stimulating factor-1 (CSF-1) delivers a proatherogenic signal to human macrophages"; *Journal of Leukocyte Biology*, 85:278-288 (Feb. 2009).
Ishikawa et al. (2005) "Development of functional human blood and immune systems in NOD/SCID/IL2 receptor {gamma} chain(null) mice"; *Blood. 106(5)*; Sep. 1, 2005:1565-73. Epub May 26, 2005.

(56) References Cited

OTHER PUBLICATIONS

Ito et al., "NOD/SCID/gamma(c)(null) mouse: an excellent recipient mouse model for engraftment of human cells"; *Blood 100(9)*; Nov. 1, 2002; pp. 3175-3182.

Ito, et al (2013) "Establishment of a human allergy model using human IL-3/GM-CSF-transgenic NOG mice"; *The Journal of Immunology 191(6)*; pp. 2890-2899.

IWHM2 2nd International Workshop on Humanized Mice, Colorado State University, Program & Abstract Book. (Apr. 3-6, 2009), Sint Olofskapei/Amsterdam, NL.

The Jackson Laboratory, "Strain Name: C; 12954-Rag2tm1.1F1v; Csf1tm1.1(CSF1)F1v; Il2rgtm1.1F1v/J" JAX Mice Database, http://jaxmic.jax.org/strain/107708.html, 6 pages (Jan. 26, 2012).

Jacob et al. (2010) "Gene targeting in the rat: advances and opportunities"; *Trends Genet. 26(12)*:510-518. doi: 10.1016/j.tig.2010.08.006. Epub Oct. 1, 2010.

Jacobs et al. (2010) "IL-7 Is Essential for Homeostatic Control of T Cell Metabolism In Vivo"; The *Journal of Immunology*, 184: 3461-3469.

Jimenez-Diaz et al. (2009) "Improved murine model of malaria using Plasmodium falciparum competent strains and non-myelodepleted NOD-scid IL2Rgnull mice engrafted with human erythrocytes. Antimicrob Agents"; *Chemother 53*: pp. 4533-4536.

Kalueff A.V. et al. (2004) "Intranasal administration of human IL-6 increases the severity of chemically induced seizures in rats"; *Neurosci Lett. 365(2)*:pp. 106-110.

Kamel-Reid and Dick, "Engraftment of immune-deficient mice with human hematopoietic stem cells"; *Science.* 242 (4886):Dec. 23, 1988; 1706-1709.

Kandalaft et al. (2011) "Angiogenesis and the tumor vasculature as antitumor immune modulators: the role of vascular endothelial growth factor and endothelin"; *Curr Top Microbiol Immunol.* 344: pp. 129-148.

Kang et al. (1999) "Defective Development of y/o T Cells in Interleukin 7 Receptor-deficient Mice Is Due to Impaired Expression of T Cell Receptor y Genes"; *J. Exp. Med., 190(7)*: 973-982.

Katano, I. et al. (2015) "Predominant development of mature and functional human NK cells in a novel human IL-2-producing transgenic NOG mouse"; *Journal of Immunology*,194(7); pp. 3513-3525.

Kaufmann et al., (2004), "Both IGH translocations and chromosome 13q deletions are early events in monoclonalgammopathy of undetermined significance and do not evolve during transition to multiple myeloma" *Leukemia.* 18: pp. 1879-1882.

Kaushansky, K. et al. (1994) "Promotion of megakaryocyte progenitor expansion and differentiation by the c-Mp1 ligand thrombopoietin", *Nature 369*: pp. 568-571.

Kaushansky, K. (1998) "Thrombopoietin", *N Engl J Med 339*: pp. 746-754.

Kaushansky, K. (2005) "The molecular mechanisms that control thrombopoiesis"; *J Clin Invest 115*: pp. 3339-3347.

Kaushansky, K. (2008) "Historical review: megakaryopoiesis and thrombopoiesis"; *Blood 111*: pp. 981-986.

Keller et al. (1996) "Molecular and Cellular Biology of Interleukin-6 and its Receptor"; *Frontiers in Bioscience*, 1: 340-357.

Kieper et al. (2002) "Overexpression of Interleukin (IL)-7 Leads to IL-15-independent Generation of Memory Phenotype CD+T Cells"; *J. Exp. Med.*, 195(12): pp. 1533-1539.

Kieran, Seay et al. (20150 In Vivo Activation of Human NK Cells by Treatment with an Interleukin-15 Superagonist Potently Inhibits Acute InVivo HIV-1 Infection in Humanized Mice'; *Journal of Virology*, vol. 89. No. 12; pp. 6264-6274.

Kim et al. (2011) "Seeing is Believing: Illuminating the Source of In Vivo Interleukin-7"; *Immune Network*, 11(1): pp. 1-7.

Kim, D.K., et al. (1998) "Engraftment of human myelody splastic syndrome derived cell line in transgenic severe combined immunodeficient (TG-SCID) mice expressing human GM-CSF and IL-3"; *European Journal of Haematology*, vol. 61; pp. 93-99.

Kinoshita Ichiro, et al. (2008) "Molecular pathophysiology of lung cancer-identification of lung cancer stem cells"; *Nippon Rinsho*, vol. 66, Suppl 6; pp. 95-99 (w/partial English translation).

Kirito, K. et al. (2003) "Thrombopoietin stimulates Hoxb4 expression: an explanation for the favorable effects of TPO on hematopoietic stem cells"; *Blood 102*:3172-3178.

Kirma et al.; "Overexpression of the Colony-Stimulating Factor (CSF-1) and/or Its Receptor c-fms in Mammary Glands of Transgenic Mice Results in Hyperplasia and Tumor Formulation"; *Cancer Resesarch*, 64; :pp. 4162-4170 (Jun. 15, 2004).

Kishimoto, Tadamitsu (1989) "The Biology of Interleukin-6"; *Blood*, 74(1): pp. 1-10.

Kishimoto, Tadamitsu, (2010) "IL-6: from its discovery to clinical applications"; *International Immunology*, 22(5): pp. 347-352.

Kirma et al., "Overexpression of the Colony-Stimulating Factor (CSF-1) and/or Its Receptor c-fms in Mammary Glands of Transgenic Mice Results in Hyperplasia and Tumor Formulation"; *Cancer Resesarch*, 64:4162-4170 (Jun. 15, 2004).

Kondo; et al. (2001) "Lymphocyte development from hematopoietic stem cells"; *Current Opn Gen & Dev 11*; pp. 520-526.

Kosco-Vilbois; et al. "A mightier mouse with human adaptive immunity"; *Nature Biotechnology*, 22 (6); (Jun. 2004); pp. 684-685.

Kovalchuk et al. (2002) "IL-6 transgenic mouse model for extraosseous plasmacytoma"; *PNAS*, 99(3): pp. 1509-1514.

Kraus et al. (2010) "A more cost effective and rapid high percentage germ-line transmitting chimeric mouse generation procedure via microinjection of 2-cell, 4-cell, and 8-cell embryos with ES and iPS cells"; *Genesis* 48(6): pp. 394-399.

Kuehl and Bergsagel (2002) "Multiple myeloma: evolving genetic events and host interactions"; *Nat Rev Cancer*. 2(3): pp. 175-187.

Kukreja et al. (2006) "Enhancement of clonogenicity of human multiple myeloma by dendritic cells", *J Exp Med. 203(8)*: pp. 1859-1865.

Kuruvilla; et al. (2007) "Dengue virus infection and immune response in humanized RAG2-1-yc-1-(RAG-hu) mice"; *Virology*, 369; pp. 143-152.

Kuter, D.J. & Rosenberg, R.D. (1995) "The reciprocal relationship of thrombopoietin (c-Mpl ligand) to changes in the platelet mass during busulfan-induced thrombocytopenia in the rabbit", *Blood 85*: pp. 2720-2730.

Landgren et al. (2009) "Monoclonal gammopathy of undetermined significance (MGUS) consistently precedes multiple myeloma: a prospective study"; *Blood 113(22)*; pp. 5412-5417.

Lapidot et al., (1992) "Cytokine stimulation of multilineage hematopoiesis from immature human cells engrafted in SCID mice"; *Science 255(5048)*; pp. 1137-1141.

Lebrec Herve, et al. (2013) "Homeostasis of human NK cells is not IL-15 dependent"; *J Immunol. 191(11)*; pp. 5551-5558.

Legrand; et al. (2006) "Experimental Models to Study Development and Function of the Human Immune System in Vivo"; *The Journal of Immunology 176*; pp. 2053-2058.

Legrand; et al. "Humanized Mice for Modeling Human Infectious Disease: Challenges, Progress, and Outlook"; *Cell Host & Microbe*, vol. 6, No. 1; (Jul. 2009); pp. 5-9. XP00258476.

Legrand et al., (2011) "Functional CD47/signal regulatory protein alpha (SIRP(alpha)) interaction is required for optimal human T- and natural killer-(NK) cell homeostasis in vivo", *Proc Natl Acad Sci USA 108(32)*: pp. 13224-13229.

Lemay L.G. et al: (1990) "Role of interleukin 6 in fever in rats"; *Am J Physiol. 258(3 Pt 2)*:R798-803.

Libby; et al. "Humanized nonobese diabetic-scid IL2ry null mice are susceptible to lethal *Salmonella typhi* infection"; *PNAS 107(35)*: (Aug. 2010) pp. 15589-15594.

Lie and Petropoulos (1998) "Advances in quantitative PCR technology: 5' nuclease assays"; *Curr. Opin. Biotechnology 9(1)*; pp. 43-48.

Liton et al. (2005) "Specific Targeting of Gene Expression to a Subset of Human Trabecular Meshwork Cells Using the Chitinase 3-Like 1 Promoter"; *Invest Ophthalmol Vis Sci.46(1)*; pp. 1831-1890.

Lombard-Platet et al. (1995) "Expression of Functional MHC Class II Molecules by a Mouse Pro-B Cell Clone"; *Developmental Immunology*, 4: pp. 85-92.

(56) References Cited

OTHER PUBLICATIONS

Lok, S. et al. (1994) "Cloning and expression of murine thrombopoietin cDNA and stimulation of platelet production in vivo", *Nature 369*: pp. 565-568.
Lu et al. (2009) "Epitope-tagged receptor knock-in mice reveal that differential desensitization of alpha2-adrenergic responses is because of ligand-selective internalization."; *J. Bioi. Chem.*, 284(19), 13233-13243.
Luo; et al. (2001) "Knock-in mice with chimeric human/murine p53 gene develop normally and show wild-type p53 responses to DNA damaging agents: a new biomedical research tool", *Oncogene 20*: pp. 320-328.
Lupton et al. (1990) "Characterization of the Human and Murine IL-7 Genes"; *The Journal of Immunology 144(9)*: pp. 3592-3601.
Ma et al. (2006) "Diverse functions of IL-2, IL-15, and IL-7 in lymphoid homeostasis"; *Annu Rev Immunol.* 24: 657-79.
Macbride Megan M.; "Meeting report: International Workshop on Humanized Mice 5"; Mar. 8, 2016; XP002758867; 4 pages.
Macchiarini, et al. "Humanized mice: are we there yet?"; *Journal of Experimental Medicine*, vol. 202, No. 10; (Nov. 2005); pp. 1307-1311; XP002559426.
Mahajan et al. (2005) "Homeostasis of T Cell Diversity"; *Cellular & Molecular Immunology*, 2(1): pp. 1-10.
Maione et al. (1998) "Coexpression of IL-6 and soluble IL-6R causes nodular regenerative hyperplasia and adenomas of the liver"; *The EMBO Journal*, 17(19): 5588-5597.
Majumder et al. (1996) "Xenogeneic expression of human stem cell factor in transgenic mice mimics codominant c-kit mutations", *Blood 87(8)*: 3203-3211.
Maksimenko, et al (2013) "Use of transgenic animals in biotechnology: prospects and problems"; *Acta Naturae*, vol. 5, No. 1; pp. 33-46.
Manz Markud M., et al.; "Human-Hemato-Lymphoid-System Mice: Opportunities and Challenges"; *Immunity*, vol. 26, No. 5; (May 2007); pp. 537-541.
Manz; et al. "Renaissance for mouse models of human hematopoiesis and immunobiology"; *Nature Immun. 10(10)*: (Oct. 2009), pp. 1039-1042.
Mason; et al. "Alcohol Exacerbates Murine Pulmonary Tuberculosis"; *Infection and Immunity* 72 (5): (May 2004) pp. 2556-2563.
Mazurier; et al. (1999) "A Novel Immunodeficient Mouse Model-RAG2 X Common Cytokine Receptor y Chain Double Mutants—Requiring Exogenous Cytokine Administration for Human Hematopoietic Stem Cell Engraftment"; *Journal of Interferon and Cytokine Research*, 19: pp. 533-541.
Mazzucchelli et al. (2007) "Interleukin-7 receptor expression: intelligent design"; *Nature*, 7: pp. 144-154.
Mazzucchelli et al. (2009) "Visualization and Identification of IL-7 Producing Cells in Reporter Mice"; *PLOS ONE*, 4(11): p. e7637.
Mcburney et al. "Murine PGK-1 promoter drives widespread but not uniform expression in transgenic mice"; *Dev Dyn.200(4)*: (Aug. 1994); pp. 278-293.
Mccune et al., "The SCID-hu mouse: murine model for the analysis of human hematolymphoid differentiation and function" *Science 241(4873)*: Sep. 23, 1988; pp. 1632-1639.
Mestas & Hughes, "Of mice and not men: differences between mouse and human immunology"; *J Immunol. 172(5)*: Mar. 1, 2004; pp. 2731-2738.
Mertsching et al. (1995) "IL-7 transgenic mice: analysis of the role of IL-7 in the differentiation of thymocytes in vivo and in vitro"; *International Immunology*, 7(3): pp. 401-414.
Meyer et al. "Gene targeting by homologous recombination in mouse zygotes mediated by zinc-finger nucleases"; *Proc Natl Acad Sci U S A*. Aug. 24, 2010; 107(34):15022-6. doi: 10.1073/pnas.1009424107. Epub Aug. 4, 2010.
Miller et al. (1985) "Generation of helper-free amphotropic retroviruses that transduce a dominant-acting, methotrexate-resistant dihydrofolate reductase gene"; *Mol Cell Biol.5(3)*: pp. 431-437.
Miller et al. "Redesign of retrovirus packaging cell lines to avoid recombination leading to helper virus production"; *Mol Cell Biol. 6(8)*: ( Aug. 1986); 2895-902.
Mittrucker; et al. (2000) "Cutting Edge: Role of B Lymphocytes in Protective Immunity Against *Salmonella typhimurium* Infection"; *J. lmmunol. 164*: pp. 1648-1652.
Miyakawa et al. (2004) "Establishment of a new model of human multiple myeloma using NOD/SCID/$y_c^{null}$ (NOG) mice"; *Biochem. Biophys. Res. Comm.*, vol. 313; pp. 258-262.
Mlecnik Bernhard, et al. (2014) "Functional network pipeline reveals genetic determinants associated with in situ lymphocyte proliferation and survival of cancer patients"; *Sci Transl Med.* 6:228ra37.
Moreadith et al. (1997) "Gene targeting in embryonic stem cells: the new physiology and metabolism"; J. Mol. Med.75(3); pp. 208-216.
Moreno et al. (2006) "The course of infections and pathology in immunomodulated NOD/LtSz-SCID mice inoculated with Plasmodium falciparum laboratory lines and clinical isolates"; *Int. J. Parasitol.* 36: pp. 361-369.
Mosier et al., "Transfer of a functional human immune system to mice with severe combined immunodeficiency"; *Nature 335(6187)*: Sep. 15, 1988; 256-259.
Motz and Coukos, "Deciphering and reversing tumor immune suppression"; *Immunity 39(1)*:Jul. 25, 2013; 61-73.
Mullins (1996) "Transgenesis in the rat and larger mammals"; *J Clin Invest* , pp. 1557 1560.
Munitic et al. (2004) "Dynamic regulation of IL-7 receptor expression is required for normal thymopoiesis"; *Blood*, 104: pp. 4165-4172.
Munoz et al. (2009) "Constraints to Progress in Embryonic Stem Cells from Domestic Species"; *Stem Cell Rev. and Rep.* 5: pp. 6-9.
Murphy et al. (1993) "Antitumor Effects of lnterleukin-7 and Adoptive Immunotherapy on Human Colon Carcinoma Xenografts"; *J. Clin. Invest.*, 92: pp. 1918-1924.
Murphy, D., BAC-based Modifications of the Mouse Genome: The Big and the Backward, Wellcome Trust Advanced Course: Genetic Manipulation of ES Cells, 58 pages (2009).
Murphy, D. MFA: the turducken of alleles, Wellcome Trust Advanced Course: Genetic Manipulation of ES Cells, 76 pages (2010).
Murray; et al. "Thrombopoietin mobilizes CD34+ cell subsets into peripheral blood and expands multilineage progenitors in bone marrow of cancer patients with normal hematopoiesis"; *Exp Hematol 26(3)*: (Mar. 1998), pp. 207-216.
Nagy et al. (1990) "Embryonic stem cells alone are able to support fetal development in the mouse"; *Development 110(3)*: pp. 815-821.
Naka et al. (2002) "The paradigm of IL-6: from basic science to medicine"; *Arthritis Research*, 4(3): S233-S242.
Nelson and Bissell (2006) "Of extracellular matrix, scaffolds, and signaling: tissue architecture regulates development, homeostasis, and cancer"; *Annu Rev Cell Dev Biol.22*: pp. 287-309.
Nevus Biologicals-a Bio-Techne Brand, "Human IL-6 Protein 5 µg", NBP2-34901 (4 pages) (2016).
Nicolini; et al. (2004) "NOD/SCID mice engineered to express human IL-3, GM-CSF and Steel factor constitutively mobilize engrafted human progenitors and compromise human stem cell regeneration"; *Leukemia 18*: pp. 341-347.
Niemann et al. (2005) "Transgenic farm animals. present and future"; *Rev. Sci. Tech. Off. Int .Epiz.* 24(1): pp. 285-298.
Nishimura, et al; (2000) "Differential Roles of Interleukin 15 mRNA Isoforms Generated by Alternative Splicing in Immune Responses In Vivo"; *J Exp Med. 191(1)*; pp. 157-170.
Nochi T, et al. (2013) "Cryptopatches are essential for the development of human GALT"; *Cell Rep*; 3(6); pp. 1874-1884.
Northemann, et al (1989) "Structure of the Rat Interleukin 6 Gene and Its Expression in Macrophage-derived Cell"; *J Biol Chem. 264(27)*: pp. 16072-16082.
O'Connell et al. (2010) "Lentiviral Vector Delivery of Human Interleukin-7 (hiL-7) to Human Immune System (HIS) Mice Expands T Lymphocyte Populations"; *PLOS ONE 5(8)*: pp. 1-10.
Palm NW, et al. (2014) "Immunoglobulin A coating identifies colitogenic bacteria in inflammatory bowel disease"; *Cell*; 158(10); pp. 1000-1010.

(56) References Cited

OTHER PUBLICATIONS

Papanicolaou Dimitris et al. (1998) "The Pathophysiologic Roles of Interleukin-6 in Human Disease"; *Ann Intern Med. 128*: pp. 127-137.
Pear et al. (1993) "Production of high-titer helper-free retroviruses by transient transfection"; *Proc Natl Acad Sci U S A.* 90(18): pp. 8392-8396.
Pearson et al. (2008), "Creation of "Humanized" Mice to Study Human Immunity"; *Curr. Protoc. Immunol. 81*: pp. 1-15.
Pek et al., "Characterization and IL-15 dependence of NK cells in humanized mice"; *Immunobiology.216(1-2)*: (Jan.-Feb. 2011) pp. 218-224.
Peters et al. (1996). "The Function of the Soluble Interleukin 6 (IL-6) Receptor In Vivo: Sensitization of Human Soluble IL-6 Receptor Transgenic Mice 6 Towards IL-6 and Prolongation of the Plasma D Half-life ofiL-6"; *J. Exp. Med. 183*: pp. 1399-1406.
Pierfrancesco Tassone, et al: "A clinically relevant SCID-hu in vivo model multiple myeloma"; *Blood American Society of Hematology*. US. vol. 106. No. 2; Jul. 15, 2005; pp. 713-716; XP002633148.
Pixley et al., "CSF-1 regulation of the wandering macrophage: complexity in action"; *Trends in Cell Biology*, 14(11): pp. 628-638 (Nov. 2004).
Pleiman et al. (1991) "Organization of the Murine and Human Interleukin-7 Receptor Genes: Two mRNAs Generated by Differential Splicing and Presence of a Type 1-Interferon-Inducible Promoter"; *Molecular and Cellular Biology*, 11 (6): pp. 3052-3059.
Polejaeva et al (2000) "Cloned pigs produced by nuclear transfer from adult somatic cells"; *Nature 407*; pp. 86-90.
Pollard, Jeffrey W.; "Tumour-educated macrophages promote tumour progression and metastasis"; *Nature Reviews*, 4; (Jan. 2004); pp. 71-78.
Poueymirou et al. (2007) "F0 generation mice that are essentially fully derived from the donor gene-targeted ES cells allowing immediate phenotypic analyses," *Nat Biot 25(1)*: pp. 91-99.
Prelle et al. (2002) "Pluripotent Stem Cells—Model of Embryonic Development, Tool for Gene Targeting, and Basis of Cell Therapy"; *Anal. Histol. Embryol. 31*; pp. 169-186.
Qian, H. et al (2007) "Critical role of thrombopoietin in maintaining adult quiescent hematopoietic stem cells"; *Cell Stem Cell 1*: pp. 671-684.
Qian and Pollard (2010) "Macrophage diversity enhances tumor progression and metastasis", *Cell 141(1)*; pp. 39-51.
Rämer Patrick C. et al. (2011) "Mice with human immune system components as in vivo models for infections with human pathogens"; *Immunol Cell Biol. 89(3)*: pp. 408-416.
Rathinam et al., "Efficient differentiation and function of human macrophages in humaized CSF-1 mice"; *Blood*, 118(11):3119-3132 (Sep. 15, 2011).
Rathinam et al., "Efficient differentiation and function of human macrophages in humaized CSF-1 mice"; *Blood*, 118(11):3119-3128 (Sep. 15, 2011)—Supplemental Figures.
Raulet, (2006), "Missing self recognition and self tolerance of natural killer (NK) cells"; *Seminars in immunology 18(3)*: pp. 145-150.
Repass et al. (2009) "IL7-hCD25 and IL7-Cre BAC transgenic mouse lines: New tools for analysis of IL-7 expressing cells"; *Genesis*, 47(4): pp. 281-287.
Rich et al. (1993) "Cutaneous Lymphoproliferation and Lymphomas in Interleukin 7 Transgenic Mice"; *J. Exp. Med.*, 177: pp. 305-316.
Rieger et al.; "Hematopoietic Cytokines Can Instruct Lineage Choice"; *Science*, 325; (Jul. 10, 2009); pp. 217-218.
Ring, Aaron M. et al. (2012) "Mechanistic and structural insight into the functional dichotomy between IL-2 and IL-15"; *Nat Immunol. 13(12)*: pp. 1187-1195.
Rohrschneider, L.R. et al. (1997) "Growth and differentiation signals regulated by the MCSF receptor", *Mol. Reprod. Dev. 46*: pp. 96-103.
Rongvaux, Anthony; "Improvement of human-hemato-lymphoid-system mice: the human Thrombopoietin knock-in mouse"; IWHM2 2nd International Workshop on Humanized Mice, PowerPoint Presentation; Apr. 3-6, 2009, Sint Olofskapei/Amsterdam, NL; pp. 1-20.
Rongvaux; "Human Thrombopoietin knockin mice efficiently support human hematopoiesis", Flavell Lab, Yale University (ASH—Dec. 6, 2010).
Rongvaux, A., et al.; "Human thrombopoietin knockin mice efficiently support human hematopoiesis in vivo", *PNAS*, vol. 108, No. 6; (Feb. 2011); pp. 2378-2383.
Rongvaux, A. et al. (2012) "MISTRG: a novel humanised mouse model to study human hematopoiesis and myeloid development and function in vivo"; *Immunology*, vol. 137, No. 1, Suppl. 1, pp. 184.
Rongvaux et al. (2013), "Human hemato-lymphoid system mice: current use and future potential for medicine"; *Annu Rev Immunol. 31*: 2013; 635-74 doi: 10.1146/annurev-immunol-032712-095921. Epub Jan. 16, 2013.
Rongvaux, Anthony et al; "Development and function of human innate immune cells in a humanized mouse model"; *Nature Biotechnology*. vol. 32. No. 4; (Apr. 2014) pp. 364-372.
Roychowdhury, Sameek, et al. (2005) "IL-15 but not IL-2 rapidly induces lethal xenogeneic graft-versus-host disease"; *Blood 106(7)*; pp. 2433-2435.
Ryan et al., "Rescue of the colony-stimulating factor 1 (CSF-1)-nullizygous mouse (Csflop/Csflop) phenotype with CSF-1 transgene and identification of sites of local CSF-1 synthesis"; *Blood*, 98(1): pp. 74-84; (Jul. 2001).
Saha et al; (2009); "Technical challenges in using human induced pluripotent stem cells to model disease"; *Cell Stem Cell.5(6)*; pp. 584-595.
Samaridis et al. (1991) "Development of lymphocytes in intereleukin 7-transgenic mice"; *Eur. J. Immunol.*, 21: pp. 453-460.
Sarrazin et al., "MafB Restricts M-CSF-Dependent Myeloid Commitment Divisions of Hematopoietic Stem Cells"; *Cell*, 138:300-313 (Jul. 24, 2009).
Sawamura D. et al.; (1998) "Induction of keratinocyte proliferation and lymphocytic infiltration by in vivo introduction of the IL-6 gene into keratinocytes and possibility of keratinocyte gene therapy for inflammatory skin diseases using IL-6 mutant genes"; *J Immunol. 161(10)*: pp. 5633-5639.
Schluns et al. (2000) "Interleukin-7 mediates the homeostasis of naive and memory COST cells in vivo"; *Nature Immunology 1(5)*; pp. 426-432.
Schorpp et al. (1996) "The human ubiquitin C promoter directs high ubiquitous expression of transgenes in mice," *Nucleic Acids Res. 24(9)*: pp. 1787-1788.
Scudellari, Megan; "The innate debate over HSCs"; *Nature Reports Stem Cells*; (published online Aug. 6, 2009 / doi: 10.1038/stemcells.2009.103); 1 page.
Semenza, G. L. et al; "Polycythemia in transgenic mice expressing the human erythropoietin gene"; *Proceedings of the National Academy of Sciences*, vol. 86, No. 7; (Apr. 1989); pp. 2301-2305.
Semenza Gregg L., et al; "Cell-type-specific and hypoxia-inducible expression of the human erythropoietin gene in transgenic mice"; *GENETICS*, vol. 88; (Oct. 1991); pp. 8725-8729.
Setty, Mala, et al. (2015) "Distinct and Synergistic Contributions of Epithelial Stress and Adaptive Immunity to Functions of Intraepithelial Killer Cells and Active Celiac Disease"; *Gastroenterology 149(3)*: pp. 681-691.
Shalapour et al. (2010) "Commensal microflora and interferon-[gamma] promote steady-state interleukin-7 production in vivo"; *European Journal of Immunology*, 40(9); pp. 2391-2399.
Sherr, C.J. et al. (1988) "Macrophage colony-stimulating factor, CSF-1, and its proto-oncogeneencoded receptor," *Cold Spring Harb. Symp. Quant. Biol. 53 Pt 1*:521-530.
Shinobara, et al. (2007) "Active integration: new strategies for transgenesis"; Transgenic research, vol. 16; pp. 333-339.
Shultz et al. (2000) "NOD/LtSz-Raglnull mice: an immunodeficient and radioresistant model for engraftment of human hematolymphoid cells, HIV infection, and adoptive transfer of NOD mouse diabetogenic T cells"; *J Immunol. 164(5)*: pp. 2496-2507.

(56) References Cited

OTHER PUBLICATIONS

Shultz; et al. (2005) "Human Lymphoid and Myeloid Cell Development in NOD/LtSz-scid IL2Ry null Mice Engrafted with Mobilized Human Hempoietic Stem Cells"; *J Immunol*, 174: pp. 6477-6489.
Shultz, Leonard D., et al; "Humanized mice for immune system investigation: progress, promise and challenges"; *Nature Reviews Immunology*, vol. 12, No. 11; (Nov. 1, 2012); pp. 786-798. XP055064740.
Shultz L D et al; "Humanized mice in translational biomedical research"; *The Journal of Immunology. Nature Pub. Group. GB*, vol. 7. No. 2; (Feb. 2007) pp. 118-130. XP002493022.
Silva et al. (2011) "IL-7 Contributes to the Progression of Human T-cell Acute Lymphoblastic Leukemias"; *Cancer Research*, 71 (14); pp. 4780-4789.
Skjot et al. (2002) "Epitope mapping of the immunodominant antigen TB10.4 and the two homologous proteins TB10.3 and TB12.9, which constitute a subfamily of the esat-6 gene family," Infect. *Immun. 70*: pp. 5446-5453.
Socolovsky, M. et al. (1998) "Cytokines in hematopoiesis: specificity and redundancy in receptor function," *Adv. Protein Chem. 52*: pp. 141-198.
Soderquest et al. (2011) "Monocytes control natural killer cell differentiation to effector phenotypes"; *Blood. 117(17)*:4511-8. doi: 10.1182/blood-2010-10-312264. Epub Mar. 9, 2011.
Sohn B; et al. "Expression and characterization of bioactive human thrombopoietin in the milk of transgenic mice", *DNA Cell Biol 18(11)*; (Nov. 1999), pp. 845-852.
Song; et al. "A Mouse Model for the Human Pathogen *Salmonella typhi*", *Cell Host & Microbe 17()* (Oct. 2010), pp. 369-376.
Spits, Hergen; "New models of human immunity"; *Nature Biotechnology* vol. 32, No. 4; (Apr. 2014), pp. 335-336.
Stanley, E. Richard, "Lineage Commitment: Cytokines Instruct, At Last!"; *Cell Stem Cell*, 5; (Sep. 4, 2009); pp. 234-236.
Stanley, E.R. et al. (1997) "Biology and action of colony—stimulating factor-1," *Mol. Reprod. Dev. 46*: pp. 4-10.
Strowig et al. (2011) "Transgenic expression of human signal regulatory protein alpha in Rag2-/-γc-/-mice improves engraftment of human hematopoietic cells in humanized mice"; *PNAS 108(32)*; pp. 13218-13223.
Strowig Till et al; "Humanized mouse models of infectious diseases"; *Drug Discovery Today: Disease Models*; (Jan. 2012) pp. e11-e16; XP055166844.
Strowig et al. (2010) "Human NK cells of mice with reconstituted human immune system components require preactivation to acquire functional competence," *Blood 116(20)*:4158-67. doi: 10.1182/blood-2010-02-270678. Epub Jul. 29, 2010.
Suematsu et al. (1989) "IgG1 plasmacytosis in interleukin 6 transgenic mice"; *Proc. Natl. Acad. Sci. USA*, 86; pp. 7547-7551.
Suematsu et al. (1992) "Generation of plasmacytomas with the chromosomal translocation t(12;15) in interleukin 6 transgenic mice"; *Proc. Natl. Acad. Sci. USA*, 89; pp. 232-235.
Sugita et al. (1990) "Functional Murine Interleukin 6 Receptor with the Intracisternal a Particle Gene Product at its Cytoplasmic Domain"; *J. Exp. Med.*, 171; pp. 2001-2009.
Takagi et al. (2012) "Membrane-bound human SCF/KL promotes in vivo human hematopoietic engraftment and myeloid differentiation," *Blood. 119(12)*; pp. 2768-2777. doi: 10.1182/blood-2011-05-353201. Epub Jan. 25, 2012.
Takenaka et al. (2007) Polymorphism in Sirpa modulates engraftment of human hematopoietic stem cells; *Nature Immunology 8*: pp. 1313-1323.
Takizawa & Manz (2007) "Macrophage tolerance: CD47-SIRP-alpha-mediated signals matter"; *Nat Immunol. 8(12)*: pp. 1287-1289.
Tan et al. (2001) "IL-7 is critical for homeostatic proliferation and survival of naive T cells"; *PNAS*, 98(15); pp. 8732-8737.

Tanabe et al.; "Genomic Structure of the Murine IL-6 Gene—High Degree Conservation of Potential Regulatory Sequences between Mouse and Human"; *The Journal of Immunology*, D 141; (1988); pp. 3875-3881.
Tang (2013) "Tumor-associated macrophages as potential diagnostic and prognostic biomarkers in breast cancer"; *Cancer Lett. 332(1)*: pp. 3-10; doi: 10.1016/j.canlet.2013.01.024. Epub Jan. 21, 2013.
Tassone et al. (2005) "A clinically relevant SCID-hu in vivo model of human multiple myeloma"; *Blood 106(2)*:pp. 713-716.
Theocharides, et al. (2012) "Disruption of SIRPα signaling in macrophages eliminates human acute myeloid leukemia stem cells in xenografts"; *J Exp Med. 209(10)*; pp. 1883-1899.
Tong et al; (2010) "Production of p53 gene knockout rats by homologous recombination in embryonic stem cells"; *Nature*; pp. 211-215.
Traggiai; et al. "Development of a Human Adaptive Immune System in Cord Blood Cell—Transplanted Mice"; *Science 304*: (Apr. 2004), pp. 104-107.
Tsantikos et al. (2010) "Autoimmune Disease in Lyn-Deficient Mice is Dependent on an Inflammatory Environment Established by IL-6"; *The Journal of Immunology*, 184; pp. 1348-1360.
Tsujinaka et al. (1995) "Muscle Undergoes Atrophy in Associate with Increase of Lysosomal Cathepsin Activity in Interleukin-6 Transgenic Mouse"; *Biochemical and Biophysical Research Communication*, 207(1); pp. 168-174.
Tsujinaka et al. (1996) "Interleukin 6 Receptor Antibody Inhibits Muscle Atrophy and Modulates Proteolytic Systems in Interleukin 6 Transgenic Mice"; *J. Clin. Invest.*, 97(1); pp. 244-249.
Tsuruta, Lisako, et al. (2003); "Transcriptional Regulation of Cytokine Genes"; *Cytokines & Cytokine Receptors: Physiology and Pathological Disorders*, Chapter 23, pp. 383-403.
Ueda, Otoya et al; "Novel genetically-humanized mouse model established to evaluate efficacy of therapeutic agents to human interleukin-6 receptor"; *Scientific Reports*. Nature Publishing Group, GB, vol. 3; Jan. 1, 2013; pp. 1196; XP002692003.
Uehira et al. (1998) "Immunologic Abnormalities Exhibited in IL-7 Transgenic Mice with Dermatitis"; *J. Invest Dermatol*, 110; pp. 740-745.
Uehira et al. (1993) "The development of dermatitis infiltrated by γδ T cells in IL-7 transgenic mice"; *International Immunology*, 5(12); pp. 1619-1627.
Valenzuela et al. (2003) "High-throughput engineering of the mouse genome coupled with high-resolution expression analysis"; *Nat Biot 21 (6)*:652-659.
Valmori et al., (1998) "Enhanced Generation of Specific Tumor-Reactive CTL In Vitro by Selected Melan-A/MART-1 Immunodominant Peptide Analogues"; *Journal of Immunology 160*: pp. 1750-1758.
Van De Wiele et al. (2007) "Impaired thymopoiesis in interleukin-7 receptor transgenic mice is not corrected by Bcl-2"; *Cellular Immunology*, 250; pp. 31-39.
Van Der Weyden et al. (2002) "Tools for Targeted Manipulation of the Mouse Genome"; *Physiological Genomics 11*; pp. 133-164.
Van Lent et al. (2009) "IL-7 enhances thymic human T cell development in "human immune system" Rag2-/-IL-2Rgammac-/- mice without affecting peripheral T cell homeostasis"; *J Immunol. 183(12)*: pp. 7645-7655.
Vaughan, Ashley M. et al; "Development of humanized mouse models to study human malaria parasite infection"; *Future Microbiology*, vol. 7, No. 5; (May 2012); pp. 657-665.
Verstegen et al. (2003) "Thrombopoietin is a major limiting factor for selective outgrowth of human umbilical cord blood cells in non-obese diabetic/severe combined immunodeficient recipient mice"; *British Journal of Hematology 122*; pp. 837-846.
Vivier et al., (2008) "Functions of natural killer cells"; *Nat Immunol. 9(5)*: pp. 503-510.
Wall (1997) "Transgenic dairy cattle: genetic engineering on a large scale"; *J Dairy Sci*; 80: pp. 2213-2224.
Watanabe (1997), "GM-CSF-mobilized peripheral blood CD34+ cells differ from steady-state bone marrow CD34+ cells in adhesion molecule expression"; *Bone Marrow Transplant. 19(12)*: pp. 1175-1181.

(56) References Cited

OTHER PUBLICATIONS

Watanabe et al. (1998) "Interleukin 7 Transgenic Mice Develop Chronic Colitis with Decreased Interleukin 7 Protein Accumulation in the Colonic Mucosa"; *J. Exp. Med.*, 187(3); pp. 389-402.
Watanabe Takeshi (2008) "Development of Humanized Mouse and Its Application"; *Chemistry and Biology*, vol. 46, No. 9, pp. 614-620 (Partial English translation attached).
Watanabe et al. (2009) "The analysis of the functions of human B and T cells in humanized NOD/shi-scid/gammac(null) (NOG) mice (hu-HSC NOG mice)"; *Int Immunol.* 21(7): pp. 843-858. doi: 10.1093/intimm/dxp050. Epub Jun. 10, 2009.
Wei et al.; "Transgenic expression of CSF-1 in CSF-1 receptor-expressing cells lead to macrophage activation, osteoporosis, and early death"; *Journal of Leukocyte Biology*, 80: pp. 1445-1453 (Dec. 2006).
Weissenbach et al. (1980) "Two interferon mRNAs in human fibroblasts: In vitro translation and D *Escherichia coli* cloning studies"; *Proc. Natl. Acad. Sci. USA*, 77(12); pp. 7152-7156.
Wendling, F. et al. (1994) "cMpl ligand is a humoral regulator of megakaryocytopoiesis"; *Nature 369*: pp. 571-574.
Wheeler et al. (2001) "Transgenic Technology and Applications in Swine"; *Theriogenology*, 56; pp. 1345-1369.
Wiktor-Jedrzejczak, W. et al. (1990) "Total absence of colony-stimulating factor 1 in the macrophage-deficient osteopetrotic (op/op) mouse" *Proc. Natl Acad. Sci. USA 87*: pp. 4828-4832.
Williams, et al. (1997) "IL-7 Overexpression in Transgenic Mouse Keratinocytes Causes a Lymphoproliferative Skin Disease Dominated by Intermediate TCR Cells"; *The Journal of Immunology 159*; pp. 3044-3056.
Willinger Tim; "A new flavor of the humanized mouse: The human IL-3/GM-CSF knock-in mouse"; IWHM2 2nd International Workshop on Humanized Mice, PowerPoint Presentation; Apr. 3-6, 2009; Sint Olofskapei/Amsterdam, NL; pp. 1-23.
Willinger, et al; "Human IL-3/GM-CSF knock-in mice support human alveolar macrophage development and human immune responses in the lung"; *PNAS 108(6)*; (Feb. 2011); pp. 2390-2395.
Willinger et al. (2011) "Improving human hemato-lymphoid-system mice by cytokine knock-in gene replacement"; *Trends in Immunology*, 32(7); pp. 321-327.
Wilmut (2003) "Dolly-her life and legacy"; Cloning Stem Cell 5; pp. 99-1 00.
Woodroofe et al. (1992) "Long-Term Consequences of Interleukin-6 Overexpression in Transgenic Mice"; *DNA and Cell Biology 11(8)*; pp. 587-592.
Yaccoby et al. (1998) "Primary myeloma cells growing in SCID-hu mice: a model for studying the biology and treatment of myeloma and its manifestations" *Blood 92(8)*: pp. 2908-2913.
Yaccoby and Epstein, (1999) "The proliferative potential of myeloma plasma cells manifest in the SCID-hu host"; *Blood. 94(10)*: pp. 3576-3582.
Yajima et al. (2008) "A new humanized mouse model of Epstein-Barr virus infection that reproduces persistent infection, lymphoproliferative disorder, and cell-mediated and humoral immune responses"; *J Infect Dis. 198(5)*: pp. 673-682. doi: 10.1086/590502.
Yamasaki et al. (1988) "Cloning and Expression of the Human Interleukin-6 (BSF-2/IFNβ2) Receptor"; *Science*, 241; pp. 825-828.
Yanagimachi (2002) "Cloning: experience from the mouse and other animals"; Mol Cell Endocrinol. 187; pp. 241-248.
Yao et al. (2014) "CyTOF supports efficient detection of immune cell subsets from small samples"; J. of Immunological Methods 415; pp. 1-5.
Yasukawa et al. (1987) "Structure and expression of human B cell stimulatory factor-2 (BSF-2/IL-6) gene"; *The EMBO Journal*, 6(10); pp. 2939-2945.
Yeung, Y.G. and Stanley, E.R. (2003) "Proteomic approaches to the analysis of early events in colony-stimulating factor-1 signal transduction," *Mol. Cell. Proteomics* 2:1143-1155.
Yoshihara, H. et al. (2007) "Thrombopoietin/MPL signaling regulates hematopoietic stem cell quiescence and interaction with the osteoblastic niche"; *Cell Stem Cell. 1(6)*: pp. 685-697. doi: 10.1016/j.stem.2007.10.020. Epub Nov. 20, 2007.
Yoshida, H. et al. (1990) "The murine mutation osteopetrosis is in the coding region of the macrophage colony stimulating factor gene," *Nature 345*:pp. 442-444.
Young; et al. (2009) "Infectious disease: Tuberculosis"; *Eur. J. Immunol 39*: pp. 1991-2058.
Yu et al., "CSF-1 receptor structure/function in MacCsf1r-/- macrophages: regulation of proliferation, differentiation, and morphology"; *Journal of Leukocyte Biology*, 84: (Sep. 2008). pp. 852-863.
Zang, WP et al. "Transfer and Expression of Recombinant Human Thrombopoietin Gene in COS-7 Cells and Mice In Vivo", [Article in Chinese] Zhongguo Shi Yan Xue Ye Xue Za Zhi 9(1): (Mar. 2001), English Abstract.
Zang, W, et al. "Thrombopoietic effect of recombinant human thrombopoietin gene transferred to mice mediated by electric pulse on normal and experimental thrombocytopenia mice", [Article in Chinese] *Zhonghua Xue Ye Xue Za Zhi.* 22(3): (Mar. 2001), English Abstract.
Zhan et al., "The molecular classification of multiple myeloma"; *Blood 108(6)*; Sep. 15, 2006; p. 2020-2028. Epub May 25, 2006.
Zhao; et al."Thrombopoietin: a potential T-helper lymphocyte stimulator. Change in T-lymphocyte composition and blood cytokine levels in thrombopoietin eDNA transferred mice", *Haematolgica 83(6)*: (Jun. 1998) pp. 572-573.
Zhou et al. (1997) "Transgenic Mice Overexpressing Human c-mpl Ligand Exhibit Chronic Thrombocytosis and Display Enhanced Recovery From 5-Fluorouracil or Antiplatelet Serum Treatment"; *Blood 89*: pp. 1551-1559.
Zhou Hongxia, et al. (2009) "Developing tTA transgenic rats for inducible and reversible gene expression"; *International Journal of Biological Sciences 5*; pp. 171-181.
Zilberstein et al. (1986) "Structure and expression of cDNA and genes for human interferon-beta-2; a distinct species inducible by growth-stimulatory cytokines"; *The EMBO Journal*, 5(10); pp. 2529-2537.
Herndler-Brandstetter D. et al: (2017) "Humanized mouse model supports development, function, and tissue residency of human natural killer cells"; Proc Natl Acad Sci U S A. 114(45); pp. E9626-E9634.
Kaushansky, et al (2014) "Of men in mice: the success and promise of humanized mouse models for human malaria parasite infections"; Cellular Microbiology, vol. 16, No. 5; pp. 602-611.
Madan A., et al (1995) "Regulated basal, inducible, and tissue-specific human erythropoietin gene expression in transgenic mice requires multiple cis DNA sequences"; Blood, vol. 85, No. 10; pp. 2735-2741.

\* cited by examiner

E

F

Comparison of engraftment levels and immune cell development and function in recipient mice with single gene replacement, in NSG, MISTRG and in humans

| | RAG2⁻/⁻ IL2Rγ⁻/⁻ (RG) | RG TPO^h/h | RG IL-3/GM-CSF^h/h | RG M-CSF^h/h | hSIRPα^h RG / NSG | MISTRG | Human |
|---|---|---|---|---|---|---|---|
| Blood hCD45⁺ cells (%) | 5-20 | 5-20 | 5-20 | 20-40 | 10-60 | 10-80 | 100 |
| BM hCD45⁺ (%) | 20-80 | 75-90 | 20-80 | 20-80 | 60-90 | 85-99 | 100 |
| Human CD33⁺ myeloid cells (% of hCD45) | 1-7 | 10-20 | 5-10 | 10-30 | 5-15 | 30-50 | 50-70 |
| Human NK cells (% of hCD45) | 0-1 | ND | ND | ND | 0.5-2 | 1-7 | 1-6 |
| Human NK cell function | - | ND | ND | ND | - | + | + |
| Serum TNFα (ng/ml, 90 min post LPS) | ND | ND | ND | ND | 0.3-3 | 10-200 | ND |
| Lung alveolar macrophages | - | - | + | - | - | + | + |

ND: Not determined

Figure 16

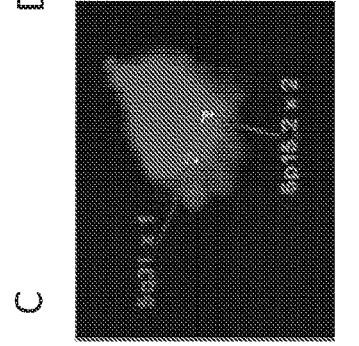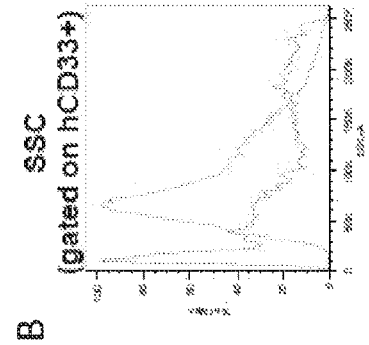
Figure 17

GENETICALLY MODIFIED NON-HUMAN ANIMALS AND METHODS OF USE THEREOF

This application is a continuation of U.S. application Ser. No. 15/598,080, filed May 17, 2017, which application is a continuation of U.S. application Ser. No. 14/420,318, filed Feb. 6, 2015, now U.S. Pat. No. 9,820,476, which application is a National Stage of International Application No. PCT/US2013/058448, filed Sep. 6, 2013, which application claims priority to U.S. Provisional Application Ser. No. 61/698,002, filed Sep. 7, 2012, and to U.S. Provisional Application Ser. No. 61/775,171, filed Mar. 8, 2013, the contents of each of which are incorporated by reference herein in their entireties.

BACKGROUND OF THE INVENTION

The aim of biomedical research is to gain a better understanding of human physiology and to use this knowledge to prevent, treat or cure human diseases. Due to practical and ethical barriers to the experimentation on human subjects, many studies are conducted on small animal models, such as the mouse. However, mice are not people and the knowledge gained from animal experimentation is not always applicable to humans. In this context, mice repopulated with a human hemato-lymphoid system (HHLS) represent a useful small animal model for the study of human hematopoiesis and immune function in vivo.

HHLS mice are generated by the transplantation of human hematopoietic stem and progenitor cells (HSPCs) and/or human fetal tissues into recipient mice deficient in the innate and adaptive arms of the immune response. The first models of HHLS mice were developed in the late 1980s (Mosier et al., 1988, Nature 335:256-259; McCune et al., 1988, Science 241:1632-1639; Kamel-Reid and Dick, 1988, Science 242:1706-1709), and have been undergoing a series of improvements since then (Legrand et al., 2006, Journal of Immunology 176:2053-2058; Shultz et al., 2007, Nature Reviews Immunology 7:118-130). The strains of mice currently used as recipients for human hematopoietic engraftment share three characteristics. First, they lack B and T cells due to the Scid mutation in the gene encoding the PRKDC protein (Mosier et al., 1988, Nature 335:256-259; McCune et al., 1988, Science 241:1632-1639), or due to deletion of one of the two Rag genes (Shultz et al., 2000, Journal of immunology 164:2496-2507; Traggiai et al., 2004, Science 304:104-107). Second, deletion or mutation of the Il2rg gene that encodese the common gamma chain ($\gamma_c$) of cytokine receptors abolishes IL-15 signaling and results in the absence of NK cells (Traggiai et al., 2004, Science 304:104-107; Ito et al. 2002, Blood 100:3175-3182). Third, the interaction between the SIRPA receptor expressed on mouse macrophages and the CD47 ligand on human cells provides an inhibitory signal to mouse macrophages and confers phagocytic tolerance for the human xenograft (Takenaka et al., 2007, Nature Immunology 8:1313-1323; Takizawa & Manz, 2007, Nature Immunology 8:1287-1289). Cross-species interaction between SIRPA expressed on mouse cells and human CD47 is achieved when using the NOD genetic background which contains a natural polymorphism in the Sirpa gene (Takenaka et al., 2007, Nature Immunology 8:1313-1323; Takizawa & Manz, 2007, Nature Immunology 8:1287-1289; Legrand et al., 2011, Proc Natl Acad Sci USA 108:13224-13229) or by BAC-transgenic expression of the human SIRPA gene (Strowig et al., 2011, Proc Natl Acad Sci USA 108:13218-13223). High levels of human hematopoietic cell engraftment, upon human HSPC transplantation, are achieved when using NOD Scid $\gamma_c^{-/-}$ (NOG (Ito et al. 2002, Blood 100:3175-3182) or NSG (Ishikawa et al., 2005, Blood 106:1565-1573)) or hSIRPA$^{tg}$ RAG2$^{-/-}$ $\gamma_c^{-/-}$ (SRG (Strowig et al., 2011, Proc Natl Acad Sci USA 108:13218-13223)) mice as recipients.

Although human multi-lineage hematopoietic development is observed in these recipient strains, the terminal differentiation, homeostasis and/or effector function of most human cell types is sub-optimal. It has been hypothesized that this condition is due to reduced or absent cross-reactivity between cytokines secreted by mouse tissues and the human receptors expressed on hematopoietic cells (Manz, 2007, Immunity 26:537-541; Willinger et al., 2011, Trends in Immunology 32:321-327). To circumvent this limitation, several strategies have been developed to deliver human cytokines in the mouse host. These methods include the injection of recombinant cytokines (Lapidot et al., 1992, Science 255:1137-1141; van Lent et al., 2009, J. Immunol 183:7645-7655), lentiviral delivery of cytokine-encoding cDNA (O'Connell et al., 2010, PloS One 5(8):e12009), hydrodynamic injection of plasmid DNA (Chen et al., 2009, Proc Natl Acad Sci USA 106:21783-21788), transgenic expression of cDNA (Nicolini et al., et al., 2004, Leukemia 18(2):341-347; Brehm et al., 2012, Blood 119:2778-2788; Takagi et al., 2012, Blood 119:2768-2777) or knock-in replacement of cytokine-encoding genes (Rongvaux et al., 2011, Proc Natl Acad Sci USA 108:2378-2383; Willinger et al., 2011, Proc Natl Acad Sci USA 108:2390-2395; Rathinam et al., 2011, Blood 118:3119-3128). The later method has the advantage of more physiological expression of the human gene. Furthermore, if the human cytokine is not fully cross-reactive on the mouse receptor, it can induce a defect in mouse cell populations and confer an additional competitive advantage to human cells. Using a knock-in gene replacement strategy, humanization of the gene encoding thrombopoietin (Tpo) resulted in better maintenance of functional human hematopoietic stem cells and increased engraftment in the bone marrow (Rongvaux et al., 2011, Proc Natl Acad Sci USA 108:2378-2383); replacement of the genes encoding interleukin-3 and GM-CSF (Il3 and Csf2) induced the loss of mouse lung alveolar macrophages (AM) and the development of functional human AM (Willinger et al., 2011, Proc Natl Acad Sci USA 108:2390-2395); and substitution of the Csf1 gene, which encodes M-CSF, resulted in increased numbers of human monocytes in multiple tissues (Rathinam et al., 2011, Blood 118:3119-3128).

Human and mouse hemato-lymphoid systems differ in many aspects (Haley, 2003, Toxicology 188:49-71; Mestas & Hughes, 2004, J Immunol 172:2731-2738). One of the major differences between the two species lies in their white blood cell (WBC) differential. Human blood is rich in myeloid cells that represent 50-75% of total WBCs. In contrast, mouse blood is dominated by lymphocytes and only 20-30% of WBCs are of myeloid lineages. This species difference, whose functional and evolutionary significance is not understood, is not recapitulated in conventional HHLS mice such as NOG/NSG or SRG. Indeed, human myeloid development is particularly defective in these hosts, with myeloid cells representing only 5-10% of human WBCs.

One application of mice with functional human immune systems is the development and testing of human vaccines. Historically, the induction of immune responses in vivo has been relatively inefficient (2004, Traggiai et al., Science 304:104-107; 2002, Ito et al., Blood 100:3175-3182; 2005, Ishikawa et al., Blood 106:1565-1573; 2005, Shultz et al., J Immunol 174:6477-6489; 2006, Baenziger et al., Proc Natl Acad Sci USA 103:15951-15956). Several studies have reported successful pathogen-specific immune responses upon infection. Although it was reported that around 50% of mice produced virus-specific IgM and IgG upon dengue virus infection (2007, Kuruvilla et al. Virology 369:143-152), other studies reported frequencies below 20% of mice producing antigen-specific IgM and IgG after HIV and EBV infection (2006, Baenziger et al., Proc Natl Acad Sci USA 103:15951-15956; 2008, Yajima et al., J Infect Dis 198:673-682). Upon immunization with adjuvant and antigen, class switching of antigen-specific immunoglobulins is also historically inefficient with only a fraction of immunized animals showing antigen specific IgG responses (2004, Traggiai et al., Science 304:104-107; 2002, Ito et al., Blood 100:3175-3182; 2005, Ishikawa et al., Blood 106:1565-1573; 2005, Shultz et al., J Immunol 174:6477-6489; 2009, Watanabe et al., Int Immunol 21:843-858; 2010, Becker et al., PLoS ONE 5). These studies included NSG and BALB/c RAG2$^{-/-}$ $\gamma_c^{-/-}$ mice and different adjuvant/antigen combinations.

There is a need in the art for humanized non-human animals able to support and sustain engraftment with human hematopoietic cells. The present invention addresses this unmet need in the art.

SUMMARY OF THE INVENTION

The invention relates generally to genetically modified non-human animals expressing at least one of human M-CSF, human IL-3, human GM-CSF, human SIRPA or human TPO, as well as to their methods of use. Thus, in one embodiment, the invention is a genetically modified non-human animal comprising a genome comprising at least one nucleic acid encoding at least one of the group consisting of human M-CSF, human IL-3, human GM-CSF, human SIRPA and human TPO, where the at least one nucleic acid is operably linked to a promoter, and where the animal expresses at least one polypeptide selected from the group consisting of human M-CSF, human IL-3, human GM-CSF, human SIRPA and human TPO. In another embodiment, the invention is a genetically modified non-human animal, comprising a genome comprising a nucleic acid encoding human M-CSF, a nucleic acid encoding human IL-3, a nucleic acid encoding human GM-CSF, a nucleic acid encoding human SIRPA and a nucleic acid encoding human TPO, where each of the nucleic acids encoding human M-CSF, human IL-3, human GM-CSF, human SIRPA and human TPO is operably linked to a promoter, and where the animal expresses human M-CSF polypeptide, human IL-3 polypeptide, human GM-CSF polypeptide, human SIRPA polypeptide and human TPO polypeptide. In some embodiments, the genetically modified non-human animal is immunodeficient. In some embodiments, the genetically modified non-human animal does not express recombination activating gene 2 (Rag-2-/-). In some embodiments, the genetically modified non-human animal does not express IL2 receptor gamma chain (gamma chain-/-). In some embodiments, the genetically modified non-human animal does not express Rag-2 and the genetically modified non-human animal does not express IL2 receptor gamma chain (Rag-2-/- gamma chain-/-). In some embodiments, the genetically modified non-human animal is a rodent. In some embodiments, the genetically modified non-human animal is a mouse. In one embodiment, the genetically modified non-human animal also includes at least one human hematopoietic cell. In one embodiment, the genetically modified non-human animal also includes at least one human cancer cell. In some embodiments, the human cancer cell is a leukemia cell or a melanoma cell.

In another embodiment, the invention is a method of hematopoietic stem and progenitor cell (HSPC) engraftment in a genetically modified non-human animal, where the animal expresses at least one of the group consisting of human M-CSF, human IL-3, human GM-CSF, human SIRPA and human TPO, the method comprising the step of: administering at least one HSPC to the genetically modified animal expressing at least one of the group consisting of human M-CSF, human IL-3, human GM-CSF, human SIRPA and human TPO. In some embodiments, the HSPC is a human HSPC. In one embodiment, the genetically modified non-human animal is a rodent. In one embodiment, the genetically modified non-human animal is a mouse. In one embodiment, the genetically modified non-human animal is immunodeficient. In one embodiment, the genetically modified immunodeficient non-human animal does not express recombination activating gene 2 (Rag-2-/-). In one embodiment, the genetically modified immunodeficient non-human animal does not express endogenous IL2 receptor (gamma chain-/-). In one embodiment, the genetically modified immunodeficient non-human animal does not express endogenous Rag-2 and does not express endogenous gamma chain (Rag-2-/- gamma chain-/-). In one embodiment, the genetically modified animal comprises a human cancer cell. In one embodiment, the human cancer cell is a leukemia cell or a melanoma cell.

In another embodiment, the invention is a genetically modified Rag-2-/-, gamma chain-/- mouse having a genome comprising at least one nucleic acid encoding at least one of the group consisting of human M-CSF, human IL-3, human GM-CSF, human SIRPA and human TPO, where the at least one nucleic acid is operably linked to at least one promoter, where the mouse expresses at least one polypeptide selected from the group consisting of human M-CSF, human IL-3, human GM-CSF, human SIRPA and human TPO. In one embodiment, the genetically modified non-human animal comprises a genome having a nucleic acid encoding human M-CSF, a nucleic acid encoding human IL-3, a nucleic acid encoding human GM-CSF, a nucleic acid encoding human SIRPA and a nucleic acid encoding human TPO, where each of the nucleic acids encoding human M-CSF, human IL-3, human GM-CSF, human SIRPA and human TPO is operably linked to a promoter, and where the animal expresses human M-CSF polypeptide, human IL-3 polypeptide, human GM-CSF polypeptide, human SIRPA polypeptide and human TPO polypeptide. In one embodiment, the genetically modified non-human animal is a rodent. In one embodiment, the genetically modified non-human animal is a mouse. In one embodiment, the genetically modified non-human animal comprises a human hematopoietic cell. In one embodiment, the genetically modified non-human animal comprises a human cancer cell. In some embodiments, the human cancer cell is a leukemia cell or a melanoma cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising (FIG. 1A) Representative flow cytometry analysis of the frequency of mouse and human CD45$^+$ cells in the blood and BM of the indicated recipient mice. Numbers next to gated areas indicate percentages among total CD45$^+$ cells. (FIG. 1B) Combined data of blood engraftment levels (% hCD45$^+$ cells) from 19 independent experiments. In each experiment, a single FL-CD34$^+$ cell sample was split and injected into mice of the respective strains. Each symbol represents an individual mouse and the red bars indicate mean values (n=56-155; ns, not significant; *p<0.05 Tukey test (see FIG. 6 for a complete statistical analysis). The gray horizontal line indicates 10% hCD45$^+$ cells. (FIG. 1C) Engraftment levels in the BM of a representative subset of mice (FIG. 6C) from panel (FIG. 6B) (n=12-16; *p<0.05 Tukey test; see also FIGS. 6D-6E). (FIG. 1D) Representative flow cytometry analysis of hCD45$^+$ cell engraftment in the blood and BM 3 months after intra-hepatic injection of 200,000 FL-CD34$^+$ cells into non-irradiated newborn MISTRG mice. (FIG. 1E) Human CD45$^+$ cell engraftment levels in the blood and BM of MISTRG mice transplanted as in (FIG. 1D) (n=16). In this case, the BM of all mice (including mice with blood hCD45$^+$<10%) are shown.

FIG. 2, comprising (FIG. 2A) Percentages of human myeloid cells (hCD33$^+$) among human hematopoietic cells (hCD45$^+$) in the blood of the indicated recipient mice, engrafted as newborns by intra-hepatic injection of FL-CD34$^+$ cells after X-ray preconditioning. Each symbol represents an individual mouse and the red bars indicate mean values (n=20-113; statistical analysis is shown in FIG. 7A). (FIG. 2B) Human WBC composition in the same mice (n=20-113 mice/group; n=8 human donors; error bars indicate SEM). (FIG. 2C) Immunohistological staining of human myeloid cells (hCD68$^+$) in non-lymphoid tissues of the indicated recipient mice. The black bar represents 20 μm, and the images shown are representative of at least three mice analyzed per group. (FIG. 2D and FIG. 2E) Representative flow cytometry analysis (FIG. 2D) and frequencies (FIG. 2E) of human monocyte subsets, identified by expression of CD14 and CD16 among hCD45$^+$CD33$^+$ cells in the blood of recipient mice (n=8-12 mice/group; error bars indicate SEM). (FIG. 2F and FIG. 2G) Cytokine production by human monocytes isolated from the BM of MITRG recipients and stimulated in vitro with LPS (FIG. 2F) or R848 (FIG. 2G) (error bars indicate SD of triplicates; representative of 3 independent experiments). (FIG. 2H) In vitro phagocytosis of GFP-expressing E. coli by human cells present in the blood of MITRG mice (n=7). (FIGS. 2I, 2J, 2K) In vivo cytokine production measured by ELISA in the serum or by RT-PCR in the lung of mice treated with LPS (Figure I; 90 min, n=15-18), or infected with Listeria monocytogenes (FIG. 2J; day 2, n=6-15) or influenza A/PR8 H1N1 (FIG. 2K; day 3, n=3-5). (FIGS. 2A, 2J, 2K) p-values calculated by one-way ANOVA followed by Tukey posthoc test (*p<0.05); (FIG. 2I) p-value calculated by unpaired Student's t-test on log10-transformed values.

FIG. 3, comprising (FIG. 3A) Quantitative RT-PCR analysis of human IL-15 and IL-15Rα mRNA expression in the liver of engrafted NSG, MITRG, and MISTRG mice (n=7-8; p-values calculated by one-way ANOVA; *, p<0.05 Tukey post hoc test). Expression was normalized to mouse Hprt. (FIG. 3B) Quantitative RT-PCR analysis of human IL-15 and IL-15Rα mRNA expression in human cell populations purified from bone marrow of engrafted MITRG (n=4-5, error bars indicate SEM). Expression was normalized to human HPRT and is shown relative to hCD14$^+$hCD16$^-$ cells. (FIG. 3C and FIG. 3D) Representative flow cytometry analysis (gated on hCD45$^+$mCD45$^-$ cells, lymphocyte gate; numbers next to outlined areas indicate percentages of cells) (FIG. 3C) and absolute number or frequency (FIG. 3D) of human NK cells (hNKp46$^+$hCD3$^-$) in engrafted NSG, MITRG, and MISTRG (n=8-16; p-values calculated by one-way ANOVA; *, p<0.05 Tukey post hoc test). (FIG. 3E) Absolute number of human liver NK (hNKp46$^+$hCD3$^-$) and T cells (hCD3$^+$, shown as control) from engrafted MISTRG mice either left untreated or treated for 3 consecutive days with liposome-encapsulated clodronate to deplete phagocytic cells (n=8; p-value calculated by unpaired Student's t-test; ns, not significant). (FIG. 3F) Labeled LCL721.221 (HLA class I negative) and LCL721.45 (class I positive) cells were injected i.v. in a 1:1 ratio, and the proportions of HLA class I positive or negative, among labeled cells recovered 12 hours later in the spleen, were used to calculate specific NK cell cytotoxicity (n=8, p-value calculated by unpaired student's t-test). (FIG. 3G) Quantitative RT-PCR analysis of human IFNγ mRNA expression in the liver of NSG and MISTRG mice 2 days after Listeria infection (n=8-9, p-value calculated by unpaired student's t-test). Expression was normalized to mouse Hprt. (FIG. 3H and FIG. 3I) Representative flow cytometry analysis (FIG. 3H) and frequency (FIG. 3I) of IFNγ-expressing and degranulating (CD107a$^+$) human liver NK cells from either uninfected or Listeria-infected NSG and MISTRG mice (n=4-11; p-value calculated by one-way ANOVA). Results are combined from two (FIGS. 3A, 3E-3I), three (FIG. 3B), or four (FIGS. 3C, 3D) experiments.

FIG. 4, comprising (FIG. 4A) Infiltration of human hematopoietic cells in the tumor, determined by the expression of mRNA encoding human hematopoietic (PTPRC, encoding CD45) and myeloid (ITGAM, encoding CD11b) markers (n=6-7; p-value calculated by unpaired Student's t-test). (FIG. 4B and FIG. 4D) Representative immunohistochemistry pictures of human myeloid cell markers in tumors from NSG, MISTRG and patients. (FIG. 4C) Quantification of the density of CD163$^+$ cells (n=3 samples/group, 3 slides counted/sample). (FIG. 4E and FIG. 4F) Representative pictures (FIG. 4E) and volume (FIG. 4F) of the tumors in the indicated groups of mice (n=7-24 mice/group). p-values were calculated by Student's t-test (FIG. 4A) or by one-way ANOVA (FIGS. 4C, 4E) followed by Tukey posthoc test (*p<0.05).

FIG. 6, comprising (FIG. 6A) Statistical analysis (one-way ANOVA followed by Tukey post-hoc test; ns, not significant) of the data presented in FIG. 1A (percentage of hCD45$^+$ cells in the blood of recipient mice). (FIG. 6B) Numbers of recipient mice that reach an engraftment level of at least 10% hCD45$^+$ cells in the blood 7-9 weeks after transplantation. (FIG. 6C) Blood engraftment levels of the mice used in FIG. 1C for analysis of the BM. (FIG. 6D) Statistical analysis, similar to (FIG. 6A), of the data presented in FIG. 1C (percentage of hCD45$^+$ cells in the BM of recipient mice). (FIG. 6E) Absolute numbers of hCD45$^+$ cells in the BM (2 femurs and 2 tibias) of recipient mice shown in FIG. 1C. The reduced numbers of cells in the BM of MISTRG is due to the smaller size of the mice at that age (10-12 weeks post-transplantation) and is caused by the first clinical signs of anemia described in detail in FIG. 10.

FIG. 7, comprising (FIG. 7A) Statistical analysis (one-way ANOVA followed by Tukey post-hoc test; ns, not significant) of the data presented in FIG. 2A (percentage of hCD33$^+$ cells in the blood of recipient mice). (FIG. 7B and FIG. 7C) Frequencies (FIG. 7B) and statistical analysis (FIG. 7C) of human myeloid cells (hCD33$^+$) in the BM of recipient mice. (FIG. 7D) Representative flow cytometry analysis of human lymphoid and myeloid lineages in the blood of MISTRG. (FIG. 7E and FIG. 7F) Representative flow cytometry analysis of human monocytes (CD33$^{hi}$SSC$^{lo}$CD66$^-$) and granulocytes (CD33$^+$SS-C$^{hi}$CD66$^+$) in the BM (FIG. 7E) and blood (FIG. 7F) of MISTRG and human donor. (FIG. 7G and FIG. 7H) Absolute numbers of human myeloid cells (hCD33$^+$) in the lung (FIG. 7G) and liver (FIG. 7H) of recipient mice (n=8-12; p-values calculated by one-way ANOVA followed by Tukey posthoc test, *p<0.05).

FIG. 8, comprising (FIG. 8A) Representative flow cytometry analysis of human monocyte subsets, identified by expression of CD14 and CD16 among hCD45$^+$ CD33$^+$ cells in the BM, spleen, lung and liver of the indicated recipient mice. (FIG. 8B) Frequencies (error bars represent SEM) among hCD33$^+$ cells and absolute numbers of monocyte subsets in the lung and liver of recipient mice (n=12 mice/group; p-values calculated by one-way ANOVA; *, p<0.05 Tukey post hoc test).

FIG. 9, comprising

FIG. 10, comprising (FIG. 10A) CFSE-labeled mouse RBCs were transferred into the indicated mice and the frequency of labeled cells was measured at the indicated time points. (FIG. 10B) Engrafted MISTRG were pre-treated or not with clodronate to deplete phagocytic cells and CFSE-labeled mouse RBCs were transferred and monitored as in (FIG. 10A) (p-value, clodronate-effect measured by repeated measure ANOVA for days 1-3). These results show that transferred mouse RBCs are rapidly cleared in vivo by phagocytic cells that are present in MISTRG but not in NSG. (FIG. 10C) RBC counts in the blood of non-engrafted mice (n=9-15) or 8-10 weeks after engraftment with human FL-CD34$^+$ cells (n=11-37). p-values indicate comparison between non-engrafted and engrafted mice of each genotype (Student's unpaired t test). (FIG. 10D) Correlation between human engraftment levels (percentage of hCD45$^+$ cells in the blood) and RBC counts (n=13-22). (FIG. 10E) Flow cytometry analysis of mouse (mTer119$^+$) and human (hCD235a$^+$) erythroid cells in the blood of non-engrafted or engrafted MISTRG, showing that almost all erythroid cells in the blood of engrafted MISTRG are of mouse origin, and human erythroid cells are barely detectable. (FIG. 10F) Representative pictures and spleen weight of engrafted mice of the indicated strains (n=3-22), showing splenomegaly in engrafted MISTRG mice. Spleens from Balb/c mice were used as a control (p-value, one-way ANOVA; *, p<0.05 compared to all other groups, Tukey posthoc test). (FIG. 10G) Histological section of the spleen of engrafted NSG and MISTRG stained with H&E, illustrating the enlargement of the red pulp in MISTRG mice with splenomegaly. (FIG. 10H) Flow cytometry analysis of mouse erythroid progenitors (mTer119$^+$mCD71$^+$), which represent up to 80% of the cells in the spleen of engrafted MISTRG. (FIG. 10I) Blood smears of non-engrafted and engrafted MISTRG illustrate enrichment in reticulocytes. Taken together, these results strongly suggest that anemia in MISTRG results from the absence of human-to-mouse phagocytic tolerance, and massive extra-medullary mouse erythropoiesis fails to compensate for the destruction of mRBCs. Results are representative of at least 5 mice examined in each group (FIGS. 10C, 10E-10I) and 2 independent experiments (FIGS. 10A, 10B).

FIG. 11, comprising (FIG. 11A) Quantitative RT-PCR analysis of human IL-15 and IL-15Rα mRNA expression in the lung of engrafted NSG, MITRG, and MISTRG mice (n=7-8; p-values calculated by one-way ANOVA; *, p<0.05 Tukey post hoc test). Expression was normalized to mouse Hprt. (FIG. 11B) Flow cytometry analysis of IL-15Rα expression on human cell populations (hCD45$^+$mCD45$^-$) from blood of engrafted MISTRG mice (representative of n=4). Histograms represent staining with isotype control or with IL-15Rα antibody, respectively. Results are representative of or combined from two experiments.

FIG. 12, comprising (FIG. 12A and FIG. 12B) Frequency (FIG. 12A) and absolute number (FIG. 12B) of human NK cells (hNKp46$^+$ hCD3$^-$) in engrafted NSG, MITRG, and MISTRG mice (n=8-16; p-values calculated by one-way ANOVA; *, p<0.05 Tukey post hoc test). Results are combined from four experiments.

FIG. 13, comprising (FIG. 13A) Flow cytometry analysis of CD94 and CD161 expression on human blood NK cells from a human donor and engrafted MISTRG (n=3). Histograms represent staining with isotype control Abs or with CD94/CD161 Abs. (FIG. 13B) Flow cytometry analysis of KIR expression on human blood NK cells from a human donor or from engrafted MISTRG mice (n=3). Numbers indicate frequencies of KIR+ cells. (FIG. 13C and FIG. 13D) CD16 surface expression on human NK cells from engrafted NSG, MITRG, and MISTRG mice (n=4-8; p-values calculated by one-way ANOVA; *, p<0.05 Tukey post hoc test). (FIG. 13E and FIG. 13F) Intracellular perforin expression by human liver NK (hNKp46+hCD3−) and T cells (hCD3+) from engrafted NSG and MISTRG mice (n=3; p-value calculated by unpaired Student's t-test). MFI, mean fluorescence intensity. Results are representative of or combined from one (FIG. 13A and FIG. 13B), two (FIG. 13E and FIG. 13F), or four (FIG. 13C and FIG. 13D) experiments.

FIG. 16 shows a comparison of engraftment levels and immune cell development and function in recipient mice with single gene replacement, in NSG, MISTRG and in humans.

FIG. 17, comprising FIGS. 17A-17D, depicts the results of experiments demonstrating that samples isolated from patients with AML, CMML and MDS can be engrafted in MISTRG. (FIG. 17A) Characteristics of the samples used (including type of disease and genetic abnormality found in patient samples), experimental protocol (method of cell purification, number of cells injected per mouse and time post-transplantation at which mice were analyzed) and engraftment results (including number of mice with detectable human engraftment, percentage of human hematopoietic CD45+ cells and myeloid CD33+ cells, and genomic abnormality observed in human cells isolated from the mice). (FIG. 17B) Representative flow cytometry analysis of the granularity (SSC) of myeloid CD33+ cells isolated from a mouse transplanted with RAEB I patient or with normal donor cells, showing deficient granularity in RAEB I samples. (FIG. 17C) Representative fish analysis of human cells isolated from mice transplanted with RAEB II sample and showing absence of chromosome 5q. (FIG. 17D) Caryotype of human cells isolated from mice transplanted with CMML sample and showing deletion in chromosome 6.

DETAILED DESCRIPTION

Figure 1A:
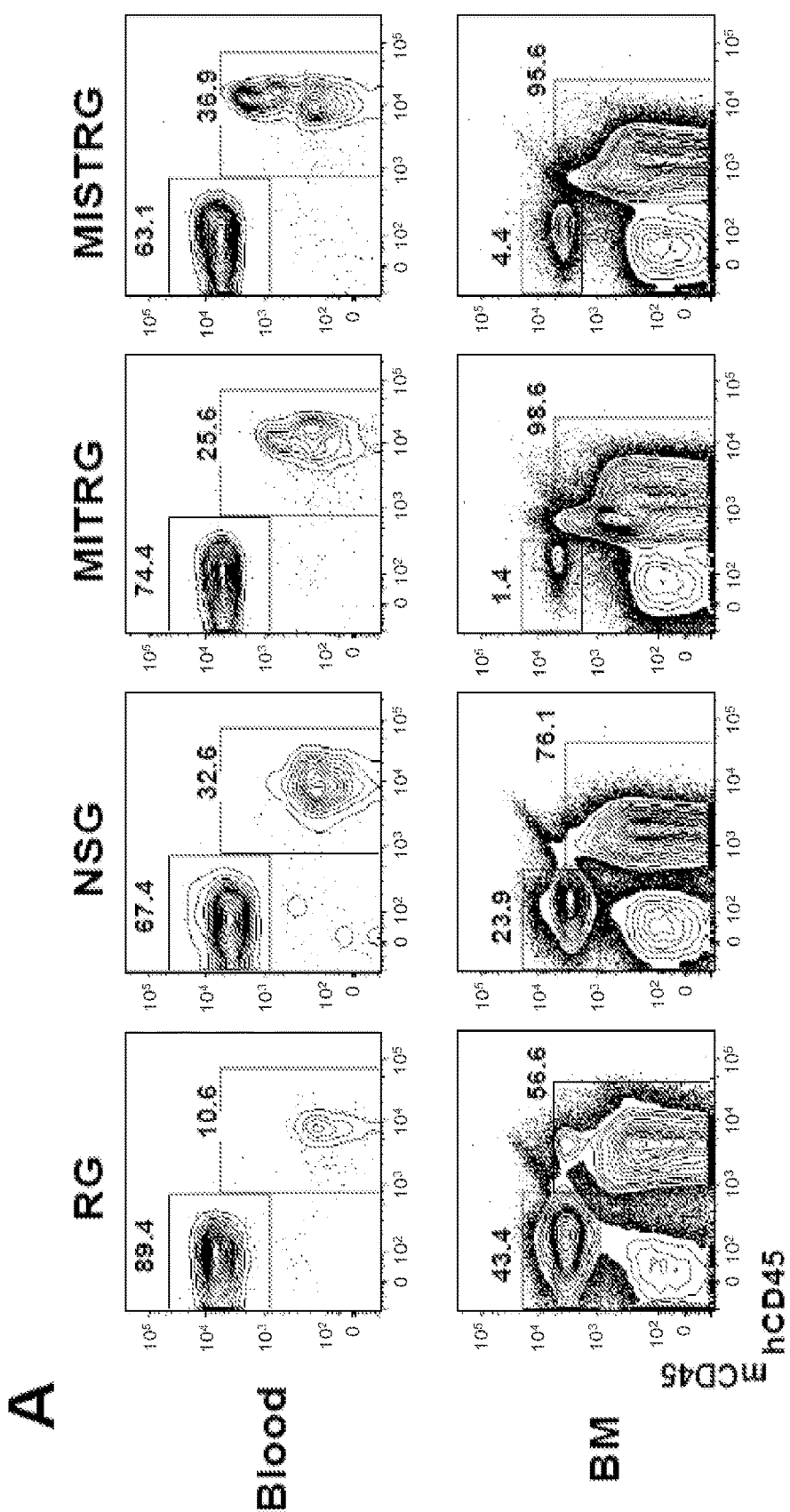
FIGS. 1A-1E, depicts the results of experiments showing that MISTRG mice support high levels of human hematopoietic engraftment. X-ray pre-conditioned newborn mice of the indicated strains were engrafted by intra-hepatic injection of 100,000 human fetal liver-(FL-) CD34$^+$ cells. Human engraftment levels (hCD45$^+$ cells) were measured in the blood 7-9 weeks later, and in the BM 10-12 weeks later.

The invention relates generally to a genetically modified non-human animal expressing at least one of human M-CSF, human IL-3, human GM-CSF, human SIRPA or human TPO. The invention also relates to methods of generating and methods of using the genetically modified non-human animals described herein. In some embodiments, the genetically modified non-human animal is a mouse. In some embodiments, the genetically modified non-human animal described herein is engrafted with human hematopoietic cells. In various embodiments, the human hematopoietic cell engrafted, genetically modified non-human animals of the invention are useful for the in vivo evaluation of the growth and differentiation of hematopoietic and immune cells, for the in vivo evaluation of human hematopoiesis, for the in vivo evaluation of cancer cells, for the in vivo assessment of an immune response, for the in vivo evaluation of vaccines and vaccination regimens, for the use in testing the effect of agents that modulate cancer cell growth or survival, for the in vivo evaluation of a treatment of cancer, for the in vivo production and collection of immune mediators, including human antibodies, and for use in testing the effect of agents that modulate hematopoietic and immune cell function.

Definitions

Unless defined otherwise, all technical and scientific terms used herein have the same meaning as commonly understood by one of ordinary skill in the art to which this invention belongs. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "cancer" as used herein is defined as disease characterized by the uncontrolled proliferation and/or growth of aberrant cells. Cancer cells can spread locally or through the bloodstream and lymphatic system to other parts of the body. Cancer as here herein includes both solid tumors and hematopoietic malignancies. Examples of various cancers amenable to the invention include, but are not limited to, breast cancer, prostate cancer, ovarian cancer, cervical cancer, skin cancer, pancreatic cancer, colorectal cancer, renal cancer, liver cancer, bone cancer, brain cancer, lymphoma, leukemia, lung cancer, myeloidysplastic syndromes, myeloproliferative disorders and the like.

"Constitutive" expression is a state in which a gene product is produced in a living cell under most or all physiological conditions of the cell.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The terms "expression construct" and "expression cassette" are used herein to refer to a double-stranded recombinant DNA molecule containing a desired nucleic acid human coding sequence and containing one or more regulatory elements necessary or desirable for the expression of the operably linked coding sequence.

As used herein, the term "fragment," as applied to a nucleic acid or polypeptide, refers to a subsequence of a larger nucleic acid or polypeptide. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between). A "fragment" of a polypeptide can be at least about 15 nucleotides in length; for example, at least about 50 amino acids to about 100 amino acids; at least about 100 to about 500 amino acids, at least about 500 to about 1000 amino acids, at least about 1000 amino acids to about 1500 amino acids; or about 1500 amino acids to about 2500 amino acids; or about 2500 amino acids (and any integer value in between).

As used herein, the terms "gene" and "recombinant gene" refer to nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

"Homologous" as used herein, refers to the subunit sequence similarity between two polymeric molecules, e.g. between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g. if half (e.g., five positions in a polymer ten subunits in length) of the positions in two compound sequences are homologous then the two sequences are 50% homologous, if 90% of the positions, e.g. 9 of 10, are matched or homologous, the two sequences share 90% homology. By way of example, the DNA sequences 5'-ATTGCC -3' and 5'-TATGGC-3' share 50% homology.

The terms "human hematopoietic stem and progenitor cells" and "human HSPC" as used herein, refer to human self-renewing multipotent hematopoietic stem cells and hematopoietic progenitor cells.

"Inducible" expression is a state in which a gene product is produced in a living cell in response to the presence of a signal in the cell.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The term "operably linked" as used herein refers to a polynucleotide in functional relationship with a second polynucleotide. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region. Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. The term "peptide" typically refers to short polypeptides. The term "protein" typically refers to large polypeptides.

The term "progeny" as used herein refers to a descendent or offspring and includes the differentiated or undifferentiated decedent cell derived from a parent cell. In one usage, the term progeny refers to a descendent cell which is genetically identical to the parent. In another use, the term progeny refers to a descendent cell which is genetically and phenotypically identical to the parent. In yet another usage, the term progeny refers to a descendent cell that has differentiated from the parent cell.

The term "promoter" as used herein refers to a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors. An included promoter can be a constitutive promoter or can provide inducible expression; and can provide ubiquitous, tissue-specific or cell-type specific expression.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

A "recombinant polypeptide" is one, which is produced upon expression of a recombinant polynucleotide.

The term "regulatory element" as used herein refers to a nucleotide sequence which controls some aspect of the expression of nucleic acid sequences. Exemplary regulatory elements illustratively include an enhancer, an internal ribosome entry site (IRES), an intron; an origin of replication, a polyadenylation signal (pA), a promoter, an enhancer, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation. Expression constructs can be generated recombinantly or synthetically using well-known methodology.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding", can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

As used herein, the term "genetically modified" means an animal, the germ cells of which comprise an exogenous human nucleic acid or human nucleic acid sequence. By way of non-limiting examples a genetically modified animal can be a transgenic animal or a knock-in animal, so long as the animal comprises a human nucleic acid sequence.

As used herein, "knock-in" is meant a genetic modification that replaces the genetic information encoded at a chromosomal locus in a non-human animal with a different DNA sequence.

Description

The invention relates to a genetically modified non-human animal expressing human M-CSF, human IL-3/GM-CSF, human SIRPA and human TPO (herein referred to as MIST). The invention also relates to methods of generating and methods of using the genetically modified non-human animals described herein. In some embodiments, the genetically modified non-human animal is a mouse. In some embodiments, the genetically modified non-human animal is an immunodeficient mouse. In a particular embodiment, the immunodeficient mouse is a RAG2$^{-/-}$ $\gamma_c^{-/-}$ mouse. In another particular embodiment, the genetically modified non-human animal of the invention expresses human M-CSF, human IL-3/GM-CSF, and human TPO and does not express RAG2 or $\gamma_c$ (referred to herein as MITRG). In another particular embodiment, the genetically modified non-human animal of the invention expresses human M-CSF, human IL-3/GM-CSF, human SIRPA and human TPO and does not express RAG2 or $\gamma_c$ (referred to herein as MISTRG). In some embodiments, the genetically modified non-human animals described herein are engrafted with a human hematopoietic cell.

In various embodiments, the human hematopoietic cell engrafted, genetically modified non-human animals of the invention are useful for the in vivo evaluation of the growth and differentiation of hematopoietic and immune cells, for the in vivo evaluation of human hematopoiesis, for the in vivo evaluation of cancer cells, for the in vivo assessment of an immune response, for the in vivo evaluation of vaccines and vaccination regimens, for the use in testing the effect of agents that modulate cancer cell growth or survival, for the in vivo evaluation of a treatment of cancer, for the in vivo production and collection of immune mediators, including human antibodies, and for use in testing the effect of agents that modulate hematopoietic and immune cell function.

Genetically Modified Non-Human Animals

The invention includes a genetically modified non-human animal that expresses at least one of human M-CSF, human IL-3/GM-CSF, human SIRPA, human TPO, and any combination thereof In some embodiments, the genetically modified non-human animal that expresses a human nucleic acid also expresses the corresponding non-human animal nucleic acid. In other embodiments, the genetically modified non-human animal that expresses a human nucleic acid does not also express the corresponding non-human animal nucleic acid. In some embodiments, the genetically modified animal is an animal having one or more genes knocked out to render the animal an immunodeficient animal, as elsewhere described herein. To create a genetically modified non-human animal, a nucleic acid encoding a human protein can be incorporated into a recombinant expression vector in a form suitable for expression of the human protein in a non-human host cell. In various embodiments, the recombinant expression vector includes one or more regulatory sequences operatively linked to the nucleic acid encoding the human protein in a manner which allows for transcription of the nucleic acid into mRNA and translation of the mRNA into the human protein. The term "regulatory sequence" is art-recognized and intended to include promoters, enhancers and other expression control elements (e.g., polyadenylation signals). Such regulatory sequences are known to those skilled in the art and are described in 1990, Goeddel, Gene Expression Technology: Methods in Enzymology 185, Academic Press, San Diego, Calif. It should be understood that the design of the expression vector may depend on such factors as the choice of the host cell to be transfected and/or the amount of human protein to be expressed.

A genetically modified animal can be created, for example, by introducing a nucleic acid encoding the human protein (typically linked to appropriate regulatory elements, such as a constitutive or tissue-specific enhancer) into an oocyte, e.g., by microinjection, and allowing the oocyte to develop in a female foster animal. Intronic sequences and polyadenylation signals can also be included in the transgene to increase the efficiency of expression of the transgene. Methods for generating genetically modified animals, particularly animals such as mice, have become conventional in the art and are described, for example, in U.S. Pat. Nos. 4,736,866 and 4,870,009 and 1986, Hogan et al., A Laboratory Manual, Cold Spring Harbor, N.Y., Cold Spring Harbor Laboratory. A genetically modified founder animal can be used to breed additional animals carrying the transgene. Genetically modified animals carrying a transgene encoding the human protein of the invention can further be bred to other genetically modified animals carrying other transgenes, or be bred to knockout animals, e.g., a knockout animal that does not express one or more of its genes. In various embodiments, the genetically modified animal of the invention is a mouse, a rat or a rabbit.

In some embodiments, the genetically modified animal of the invention expresses one or more human nucleic acids from the non-human animal's native promoter and native regulatory elements. In other embodiments, the genetically modified animal of the invention expresses a human nucleic acid from the native human promoter and native regulatory elements. The skilled artisan will understand that the genetically modified animal of the invention includes genetically modified animals that express at least one human nucleic acid from any promoter. Examples of promoters useful in the invention include, but are not limited to, DNA pol II promoter, PGK promoter, ubiquitin promoter, albumin promoter, globin promoter, ovalbumin promoter, SV40 early promoter, the Rous sarcoma virus (RSV) promoter, retroviral LTR and lentiviral LTR. Promoter and enhancer expression systems useful in the invention also include inducible and/or tissue-specific expression systems.

In some embodiments, the invention includes genetically modified immunodeficient animals having a genome that includes a nucleic acid encoding a human polypeptide operably linked to a promoter, wherein the animal expresses the encoded human polypeptide. In various embodiments, the invention includes genetically modified immunodeficient non-human animals having a genome that comprises an expression cassette that includes a nucleic acid encoding at least one human polypeptide, wherein the nucleic acid is operably linked to a promoter and a polyadenylation signal and further contains an intron, and wherein the animal expresses the encoded human polypeptide.

In various embodiments, various methods are used to introduce a human nucleic acid sequence into an immunodeficient animal to produce a genetically modified immunodeficient animal that expresses a human gene. Such techniques are well-known in the art and include, but are not limited to, pronuclear microinjection, transformation of embryonic stem cells, homologous recombination and knock-in techniques. Methods for generating genetically modified animals that can be used include, but are not limited to, those described in Sundberg and Ichiki (2006, Genetically Engineered Mice Handbook, CRC Press), Hofker and van Deursen (2002, Genetically modified Mouse Methods and Protocols, Humana Press), Joyner (2000, Gene Targeting: A Practical Approach, Oxford University Press), Turksen (2002, Embryonic stem cells: Methods and Protocols in Methods Mol Biol., Humana Press), Meyer et al. (2010, Proc. Nat. Acad. Sci. USA 107:15022-15026), and Gibson (2004, A Primer Of Genome Science $2^{nd}$ ed. Sunderland, Mass.: Sinauer), U.S. Pat. No. 6,586,251, Rathinam et al. (2011, Blood 118:3119-28), Willinger et al., (2011, Proc Natl Acad Sci USA, 108:2390-2395), Rongvaux et al., (2011, Proc Natl Acad Sci USA, 108:2378-83) and Valenzuela et al. (2003, Nat Biot 21:652-659).

In some embodiments, the compositions and methods of the invention comprise genetically modified immunodeficient animals deficient in B cell and/or T cell number and/or function, alone, or in combination with a deficiency in NK cell number and/or function (for example, due to an IL2 receptor gamma chain deficiency (i.e., $\gamma_c^{-/-}$)), and having a genome that comprises a human nucleic acid operably linked to a promoter, wherein the animal expresses the encoded human polypeptide. The generation of the genetically modified animal of the invention can be achieved by methods such as DNA injection of an expression construct into a preimplantation embryo or by use of stem cells, such as embryonic stem (ES) cells or induced pluripotent stem (iPS) cells.

In one embodiment, the human nucleic acid is expressed by the native regulatory elements of the human gene. In other embodiments, the human nucleic acid is expressed by the native regulatory elements of the non-human animal. In other embodiments, human nucleic acid is expressed from a ubiquitous promoter. Nonlimiting examples of ubiquitous promoters useful in the expression construct of the compositions and methods of the invention include, a 3-phosphoglycerate kinase (PGK-1) promoter, a beta-actin promoter, a ROSA26 promoter, a heat shock protein 70 (Hsp70) promoter, an EF-1 alpha gene encoding elongation factor 1 alpha (EF1) promoter, an eukaryotic initiation factor 4A (eIF-4A1) promoter, a chloramphenicol acetyltransferase (CAT) promoter and a CMV (cytomegalovirus) promoter.

In other embodiments, the human nucleic acid is expressed from a tissue-specific promoter. Nonlimiting examples of tissue-specific promoters useful in the expression construct of the compositions and methods of the invention include a promoter of a gene expressed in the hematopoietic system, such as a M-CSF promoter, an IL-3 promoter, a GM-CSF promoter, a SIRPA promoter, a TPO promoter, an IFN-β promoter, a Wiskott-Aldrich syndrome protein (WASP) promoter, a CD45 (also called leukocyte common antigen) promoter, a Flt-1 promoter, an endoglin (CD105) promoter and an ICAM-2 (Intracellular Adhesion Molecule 2) promoter. These and other promoters useful in the compositions and methods of the invention are known in the art as exemplified in Abboud et al. (2003, J. Histochem & Cytochem. 51:941-949), Schorpp et al. (1996, NAR 24:1787-1788), McBurney et al. (1994, Devel. Dynamics, 200:278-293) and Majumder et al. (1996, Blood 87:3203-3211). Further to comprising a promoter, one or more additional regulatory elements, such as an enhancer element or intron sequence, is included in various embodiments of the invention. Examples of enhancers useful in the compositions and methods of the invention include, but are not limited to, a cytomegalovirus (CMV) early enhancer element and an SV40 enhancer element. Examples of intron sequences useful in the compositions and methods of the invention include, but are not limited to, the beta globin intron or a generic intron. Other additional regulatory elements useful in some embodiments of the invention include, but are not limited to, a transcription termination sequence and an mRNA polyadenylation (pA) sequence.

In some embodiments, the methods of introduction of the human nucleic acid expression construct into a preimplantation embryo include linearization of the expression construct before it is injected into a preimplantation embryo. In preferred embodiments, the expression construct is injected into fertilized oocytes. Fertilized oocytes can be collected from superovulated females the day after mating and injected with the expression construct. The injected oocytes are either cultured overnight or transferred directly into oviducts of 0.5-day p.c. pseudopregnant females. Methods for superovulation, harvesting of oocytes, expression construct injection and embryo transfer are known in the art and described in Manipulating the Mouse Embryo (2002, A Laboratory Manual, 3rd edition, Cold Spring Harbor Laboratory Press). Offspring can be evaluated for the presence of the introduced nucleic acid by DNA analysis (e.g., PCR, Southern blot, DNA sequencing, etc.) or by protein analysis (e.g., ELISA, Western blot, etc.).

In other embodiments, the expression construct may be transfected into stem cells (ES cells or iPS cells) using well-known methods, such as electroporation, calcium-phosphate precipitation and lipofection. The cells can be evaluated for the presence of the introduced nucleic acid by DNA analysis (e.g., PCR, Southern blot, DNA sequencing, etc.) or by protein analysis (e.g., ELISA, Western blot, etc.). Cells determined to have incorporated the expression construct can then be microinjected into preimplantation embryos. For a detailed description of methods known in the art useful for the compositions and methods of the invention, see Nagy et al., (2002, Manipulating the Mouse Embryo: A Laboratory Manual, 3rd edition, Cold Spring Harbor Laboratory Press), Nagy et al. (1990, Development 110:815-821), U.S. Pat. Nos. 7,576,259, 7,659,442, 7,294,754, and Kraus et al. (2010, Genesis 48:394-399).

The genetically modified non-human animals of the invention can be crossed to immunodeficient animal to create an immunodeficient animal expressing at least one human nucleic acid. Various embodiments of the invention provide genetically modified animals that include a human nucleic acid in substantially all of their cells, as well as genetically modified animals that include a human nucleic acid in some, but not all their cells. One or multiple copies, adjacent or distant to one another, of the human nucleic acid may be integrated into the genome of the cells of the genetically modified animals.

In some embodiments, the invention is a genetically modified non-human mouse engrafted with at least one human hematopoietic cell. In other embodiments, the invention is a method of engrafting human hematopoietic cells in a genetically modified non-human animal. The engrafted human hematopoietic cells useful in the compositions and methods of the invention include any human hematopoietic cell. Non-limiting examples of human hematopoietic cells useful in the invention include, but are not limited to, HSC, HSPC, leukemia initiating cells (LIC), and hematopoietic cells of any lineage at any stage of differentiation, including terminally differentiated hematopoietic cells of any lineage. Such hematopoietic cells can be derived from any tissue or location of a human donor, including, but not limited to, bone marrow, peripheral blood, liver, fetal liver, or umbilical cord blood. Such hematopoietic cells can be isolated from any human donor, including healthy donors, as well as donors with disease, such as cancer, including leukemia.

In other embodiments, the invention is a method of engrafting human hematopoietic cells in a genetically modified non-human animal. In some embodiments, the genetically modified non-human animal into which human hematopoietic cells are engrafted is an immunodeficient animal. Engraftment of hematopoietic cells in the genetically modified animal of the invention is characterized by the presence of human hematopoietic cells in the engrafted animal. In particular embodiments, engraftment of hematopoietic cells in an immunodeficient animal is characterized by the presence of differentiated human hematopoietic cells in the engrafted animal in which hematopoietic cells are provided, as compared with appropriate control animals.

In some embodiments, the animals of the invention are transplanted with human cancer cells (e.g., human solid tumors, etc.) in addition to human hematopoietic cells. In various embodiments, the human cancer cells can be a cancer cell line or primary human cancer cell isolated from a patient, from any of many different types of cancer (including, by way of non-limiting examples, melanoma, breast cancer, lung cancer, etc.) In some embodiments, the human cancer cell and the HSPC are isolated from the same patient and transplanted into the same non-human animal.

The genetically modified non-human animals provided in various embodiments of the present invention have various utilities such as, but not limited to, for use as models of growth and differentiation of hematopoietic cells, for the in vivo evaluation of human hematopoiesis, for the in vivo evaluation of cancer cells, for in vivo study of an immune response, for in vivo evaluation of vaccines and vaccination regimens, for the use in testing the effect of agents that modulate cancer cell growth or survival, for the in vivo evaluation of a treatment of cancer, for in vivo production and collection of immune mediators, such as an antibody, and for use in testing the effect of agents that affect hematopoietic and immune cell function.

Engraftment of human hematopoietic cells in genetically modified and/or immunodeficient non-human animals has traditionally required conditioning prior to administration of the hematopoietic cells, either sub-lethal irradiation of the recipient animal with high frequency electromagnetic radiation, generally using gamma or X-ray radiation, or treatment with a radiomimetic drug such as busulfan or nitrogen mustard. Conditioning is believed to reduce numbers of host hematopoietic cells, create appropriate microenvironmental factors for engraftment of human hematopoietic cells, and/or create microenvironmental niches for engraftment of human hematopoietic cells. Standard methods for conditioning are known in the art, such as described herein and in J. Hayakawa et al, 2009, Stem Cells, 27(1):175-182. Methods for engraftment of human hematopoietic cells in immunodeficient animals are provided according to embodiments of the present invention which include providing human hematopoietic cells to the immunodeficient animals, with or without irradiating the animals prior to administration of the hematopoietic cells. Methods for engraftment of human hematopoietic cells in immunodeficient animals are provided according to embodiments of the present invention which include providing human hematopoietic cells to the genetically modified non-human animals of the invention, with or without, administering a radiomimetic drug, such as busulfan or nitrogen mustard, to the animals prior to administration of the hematopoietic cells.

In some embodiments, the methods of hematopoietic cell engraftment in a genetically modified non-human animal according to embodiments of the present invention include providing human hematopoietic cells to a genetically modified animal of the invention as elsewhere described here. In some embodiments, the genetically modified non-human animal of the invention is an immunodeficient animal that is deficient in non-human B cell number and/or function, non-human T cell number and/or function, and/or non-human NK cell number and/or function. In other embodiments, the immunodeficient animal has severe combined immune deficiency (SCID). SCID refers to a condition characterized by the absence of T cells and lack of B cell function. Examples of SCID include: X-linked SCID, which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+). In some embodiments, the genetically modified non-human animal of the invention is RAG1$^{-/-}$.

In some embodiments, the methods of hematopoietic cell engraftment in a genetically modified animal according to embodiments of the present invention include providing human hematopoietic cell to in a genetically modified non-human animal having the severe combined immunodeficiency mutation (Prkdc$^{scid}$), commonly referred to as the scid mutation. The scid mutation is well-known and located on mouse chromosome 16 as described in Bosma et al. (1989, Immunogenetics 29:54-56). Mice homozygous for the scid mutation are characterized by an absence of functional T cells and B cells, lymphopenia, hypoglobulinemia and a normal hematopoietic microenvironment. The scid mutation can be detected, for example, by detection of markers of the scid mutation using well-known methods.

In other embodiments, the methods of hematopoietic cell engraftment in a genetically modified animal according to embodiments of the present invention include providing human hematopoietic cells to genetically modified immunodeficient non-human animal having an IL2 receptor gamma chain deficiency, either alone, or in combination with, the severe combined immunodeficiency (scid) mutation. The term "IL2 receptor gamma chain deficiency" refers to decreased IL2 receptor gamma chain. Decreased IL2 receptor gamma chain can be due to gene deletion or mutation. Decreased IL2 receptor gamma chain can be detected, for example, by detection of IL2 receptor gamma chain gene deletion or mutation and/or detection of decreased IL2 receptor gamma chain expression using well-known methods.

In addition to the naturally occurring human nucleic acid and amino acid sequences, the term encompasses variants of human nucleic acid and amino acid sequences As used herein, the term "variant" defines either an isolated naturally occurring genetic mutant of a human or a recombinantly prepared variation of a human, each of which contain one or more mutations compared with the corresponding wild-type human. For example, such mutations can be one or more amino acid substitutions, additions, and/or deletions. The term "variant" also includes non-human orthologues. In some embodiments, a variant polypeptide of the present invention has at least 90%, 91%, 92%, 93%, 94%, 95%, 96%, 97%, 98% or 99% identity to a wild-type human polypeptide.

The percent identity between two sequences is determined using techniques as those described elsewhere herein. Mutations can be introduced using standard molecular biology techniques, such as site-directed mutagenesis and PCR-mediated mutagenesis. One of skill in the art will recognize that one or more amino acid mutations can be introduced without altering the functional properties of human proteins.

Conservative amino acid substitutions can be made in human proteins to produce human protein variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Human variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, methylhistidine, and ornithine.

Human variants are encoded by nucleic acids having a high degree of identity with a nucleic acid encoding a wild-type human. The complement of a nucleic acid encoding a human variant specifically hybridizes with a nucleic acid encoding a wild-type human under high stringency conditions.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

Nucleic acids encoding a human variant can be isolated or generated recombinantly or synthetically using well-known methodology.

Isolation of human hematopoietic cells, administration of the human hematopoietic cells to a host animal and methods for assessing engraftment thereof are well-known in the art. Hematopoietic cells for administration to host animal can be obtained from any tissue containing hematopoietic cells such as, but not limited to, umbilical cord blood, bone marrow, peripheral blood, cytokine or chemotherapy-mobilized peripheral blood and fetal liver. Hematopoietic cells can be administered into newborn or adult animals by administration via various routes, such as, but not limited to, intravenous, intrahepatic, intraperitoneal, intrafemoral and/or intratibial.

Engraftment of human hematopoietic cells in the genetically modified animal of the invention can be assessed by any of various methods, such as, but not limited to, flow cytometric analysis of cells in the animals to which the human hematopoietic cells are administered at one or more time points following the administration of hematopoietic cells.

Exemplary methods of isolating human hematopoietic cells, of administering human hematopoietic cells to a host animal, and of assessing engraftment of the human hematopoietic cells in the host animal are described herein and in Pearson et al. (2008, Curr. Protoc. Immunol. 81:1-15), Ito et al. (2002, Blood 100:3175-3182), Traggiai et al. (2004, Science 304:104-107), Ishikawa et al. (2005, Blood 106: 1565-1573), Shultz et al. (2005, J. Immunol. 174:6477-6489) and Holyoake et al. (1999, Exp Hematol. 27:1418-27).

In some embodiments of the invention, the human hematopoietic cells are isolated from an original source material to obtain a population of cells enriched for a particular hematopoietic cell population (e.g., HSCs, HSPCs, LICs, CD34+, CD34−, lineage specific marker, etc.). The isolated hematopoietic cells may or may not be a pure population. In one embodiment, hematopoietic cells useful in the compositions and methods of the invention are depleted of cells having a particular marker, such as CD34. In another embodiment, hematopoietic cells useful in the compositions and methods of the invention are enriched by selection for a marker, such as CD34. In some embodiments, hematopoietic cells useful in the compositions and methods of the invention are a population of cells in which CD34+ cells constitute about 1-100% of the cells, although in certain embodiments, a population of cells in which CD34+ cells constitute fewer than 1% of total cells can also be used. In certain embodiments, the hematopoietic cells useful in the compositions and methods of the invention are a T cell-depleted population of cells in which CD34+ cells make up about 1-3% of total cells, a lineage-depleted population of cells in which CD34+ cells make up about 50% of total cells, or a CD34+positive selected population of cells in which CD34+ cells make up about 90% of total cells.

The number of hematopoietic cells administered is not considered limiting with regard to the generation of a human hematopoietic and/or immune system in a genetically modified non-human animal expressing at least one human gene. Thus, by way of non-limiting example, the number of hematopoietic cells administered can range from about $1 \times 10^3$ to about $1 \times 10^7$, although in various embodiments, more or fewer can also be used. By way of another non-limiting example, the number of HSPCs administered can range from about $3 \times 10^3$ to about $1 \times 10^6$ CD34+ cells when the recipient is a mouse, although in various embodiments, more or fewer can also be used. For other species of recipient, the number of cells that need to be administered can be determined using only routine experimentation.

Generally, engraftment can be considered successful when the number (or percentage) of human hematopoietic cells present in the genetically modified non-human animal is greater than the number (or percentage) of human cells that were administered to the non-human animal, at a point in time beyond the lifespan of the administered human hematopoietic cells. Detection of the progeny of the administered hematopoietic cells can be achieved by detection of human DNA in the recipient animal, for example, or by detection of intact human hematopoietic cells, such as by the detection of the human cell surface marker, such as CD45 for example. Serial transfer of human hematopoietic cells from a first recipient into a secondary recipient, and engraftment of human hematopoietic cells in the second recipient, is a further optional test of engraftment in the primary recipient. Engraftment can be detected by flow cytometry as 0.05% or greater human CD45+ cells in the blood, spleen or bone marrow at 1-4 months after administration of the human hematopoietic cells. A cytokine (e.g., GM-CSF) can be used to mobilize stem cells, for example, as described in Watanabe (1997, Bone Marrow Transplantation 19:1175-1181).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Functional Innate Immune Responses and Solid Tumor Support in Human-Hemato-Lymphoid System Mice As described herein, mice repopulated with a human hemato-lymphoid system (HHLS) represent a powerful tool for predictive human preclinical in vivo research. A major limitation of current HHLS mice is the defective development of human cells critical for innate immunity. Here, a novel mouse strain is reported in which multiple genes encoding cytokines are genetically humanized. These humanized cytokines act synergistically to efficiently support human hematopoiesis and the development and function of human monocytes/macrophages and NK cells. In a tumor microenvironment, human macrophages acquire an immunosuppressive phenotype and support the growth of a human cancer. With a more complete and functional human innate immune system, this novel model of HHLS mice has exceptional potential to facilitate the study of physiology and pathology of human innate immunity in vivo.

Monocytes and macrophages are major cellular components of the innate immune response (Auffray et al., 2009, Annual review of immunology 27, 669). On the one hand, these cells are capable of sensing an infection and of mediating direct anti-microbial functions, by diverse mechanisms such as phagocytosis or the secretion of pro-inflammatory factors. On the other hand, monocytes/macrophages can acquire immunosuppressive functions, important for the resolution of inflammation and for tissue repair. Furthermore, these anti-inflammatory properties can be co-opted by tumor-infiltrating macrophages and provide a survival advantage to evolving tumors through a diversity of mechanisms (Allavena and Mantovani, 2012, Clinical and experimental immunology 167, 195; Qian and Pollard, 2010, Cell 141, 39).

Small animal models such as mice are frequently used to study in vivo mammalian immune responses. However, fundamental differences in immune function exist between species (Mestas and Hughes, 2004, Journal of Immunology 172, 2731; Rongvaux et al., 2013, Annual review of immunology 31, 635). In particular, major phenotypic and functional species-specific differences exist among monocytes/macrophages populations and generally, knowledge gained from mouse studies is only partly applicable to humans (Auffray et al., 2009, Annual review of immunology 27, 669; Rongvaux et al., 2013, Annual review of immunology 31, 635; Chow et al., 2011, Nature reviews Immunology 11, 788). One promising approach to study the specificities of human hematopoietic and immune function in vivo consists in using mice carrying a human hemato-lymphoid system (HHLS) (Rongvaux et al., 2013, Annual review of immunology 31, 635; Shultz et al., 2012, Nature reviews Immunology 12, 786). However, the development and function of several human immune cell types, such as monocytes/macrophages and NK cells, is largely defective in current HHLS mice (Rongvaux et al., 2013, Annual review of immunology 31, 635). These defects are most likely due to reduced cross-reactivity of mouse cytokines on the corresponding human receptors (Manz, 2007, Immunity 26, 537). To circumvent this limitation, a strategy was developed to replace mouse genes encoding cytokines by their human counterpart (Willinger et al., 2011, Trends in immunology 32, 321) and this approach resulted in significant improvements in the development and function of individual human cell types (FIG. 16) (Rathinam et al., 2011, Blood 118, 3119; Willinger et al., 2011, Proceedings of the National Academy of Sciences 108, 2390; Rongvaux et al., 2011, Proceedings of the National Academy of Sciences 108, 2378).

Figure 5:
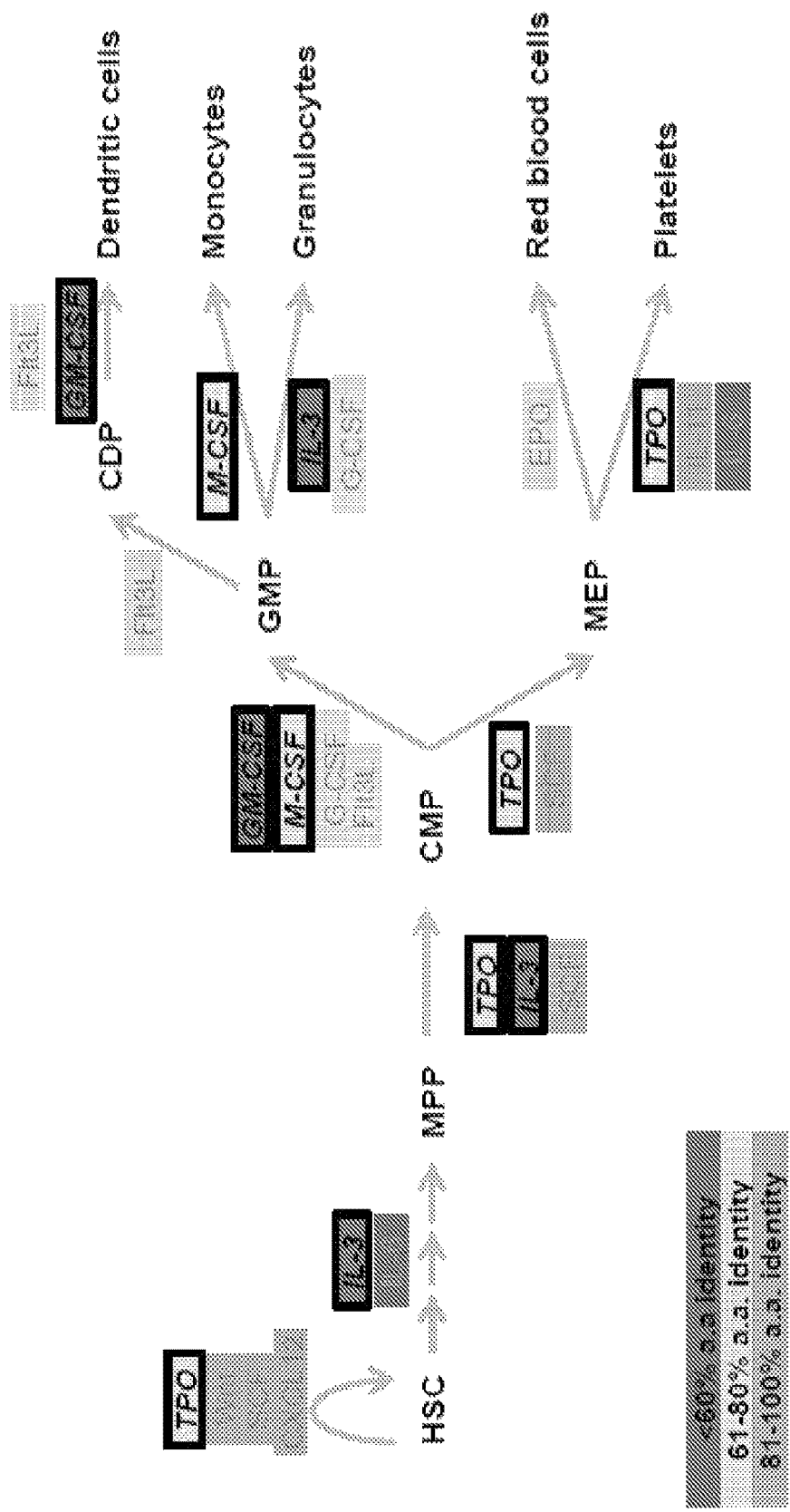
FIG. 5 depicts cytokines involved in HSC function and myeloid development. Schematic representation of hematopoietic stem cell development into myeloid cells and non-exhaustive list of cytokines known to regulate this process. Shading indicates the percentages of amino acid identity between human and mouse cytokines. The percentage of amino acid identity is the most objective measure of protein conservation between species, but it does not always correlate with functional inter-species cross-reactivity in vivo. Black rectangles indicate cytokines that are genetically humanized in MISTRG. HSC, hematopoietic stem cell; MPP, multipotent progenitor; CMP, common myeloid progenitor; GMP, granulocyte/macrophage progenitor; MEP, megakaryocyte/erythrocyte progenitor.

Hematopoiesis is a tightly regulated developmental process in which multipotent hematopoietic stem cells differentiate into more committed progenitors and then into mature blood cells (Kondo et al., 2003, Annual review of immunology 21, 759; Doulatov et al., 2012, Cell stem cell 10, 120). This process requires specific cytokines that support successive developmental steps (FIG. 5). Perhaps synergy between multiple humanized cytokines would be required to fully recapitulate human myelopoiesis in the mouse. Thus, a novel mouse strain, named MISTRG, was generated in which the genes encoding M-CSF (Rathinam et al., 2011, Blood 118, 3119), IL-3/GM-CSF (Willinger et al., 2011, Proceedings of the National Academy of Sciences 108, 2390) and TPO (Rongvaux et al., 2011, Proceedings of the National Academy of Sciences 108, 2378) were replaced by their human counterparts (Willinger et al., 2011, Trends in immunology 32, 321) in the hSIRPAtg RAG2−/− IL-2Rγ−/− background (Traggiai et al., 2004, Science 304, 104; Strowig et al., 2011, Proceedings of the National Academy of Sciences 108, 13218).

Figures 1B, 1C:
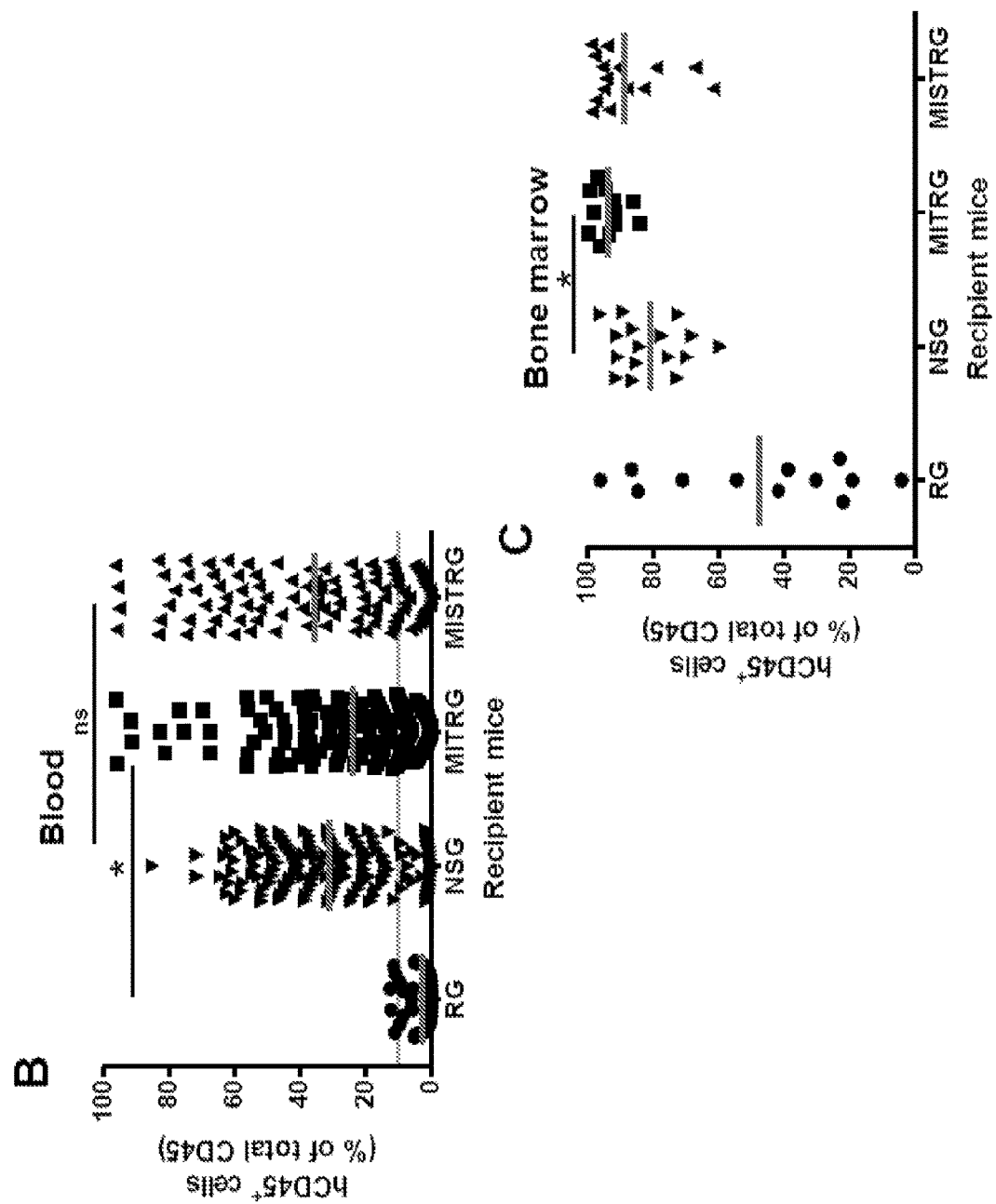
Figures 1D, 1E:
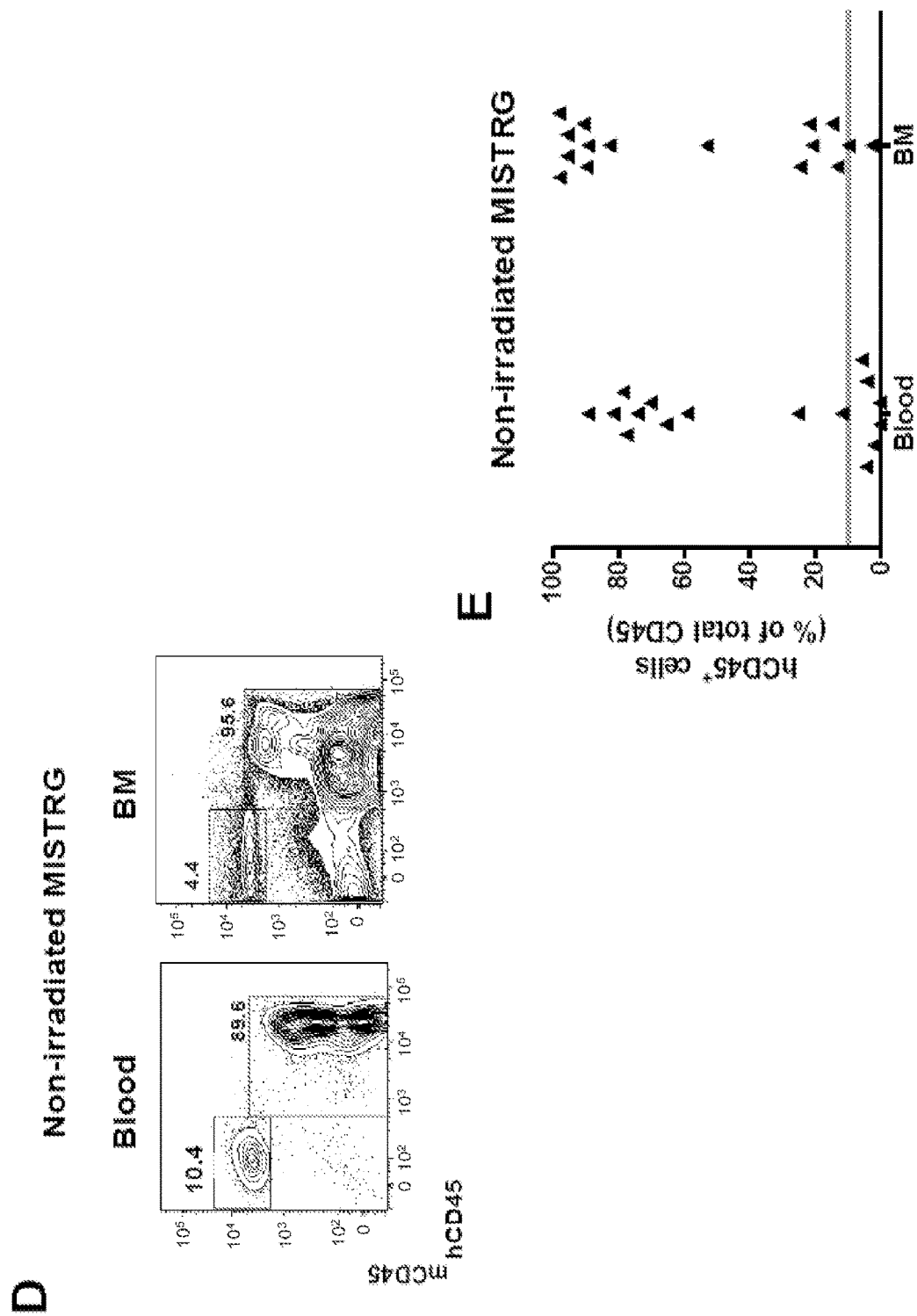
Figures 6A, 6B, 6C:
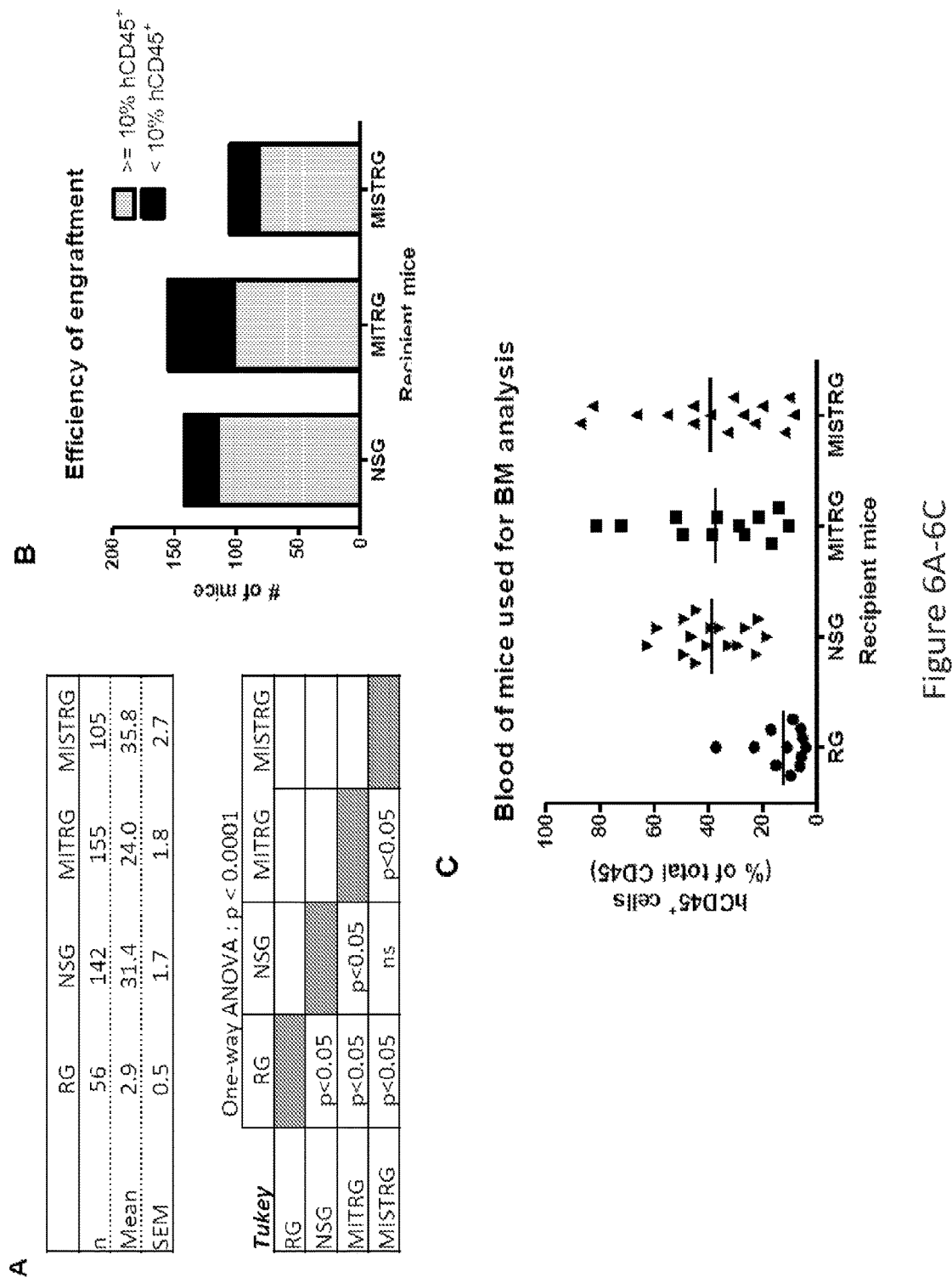
FIGS. 6A-6E, depicts the results of statistical analysis of engraftment levels in recipient mice.
Figures 6D, 6E:
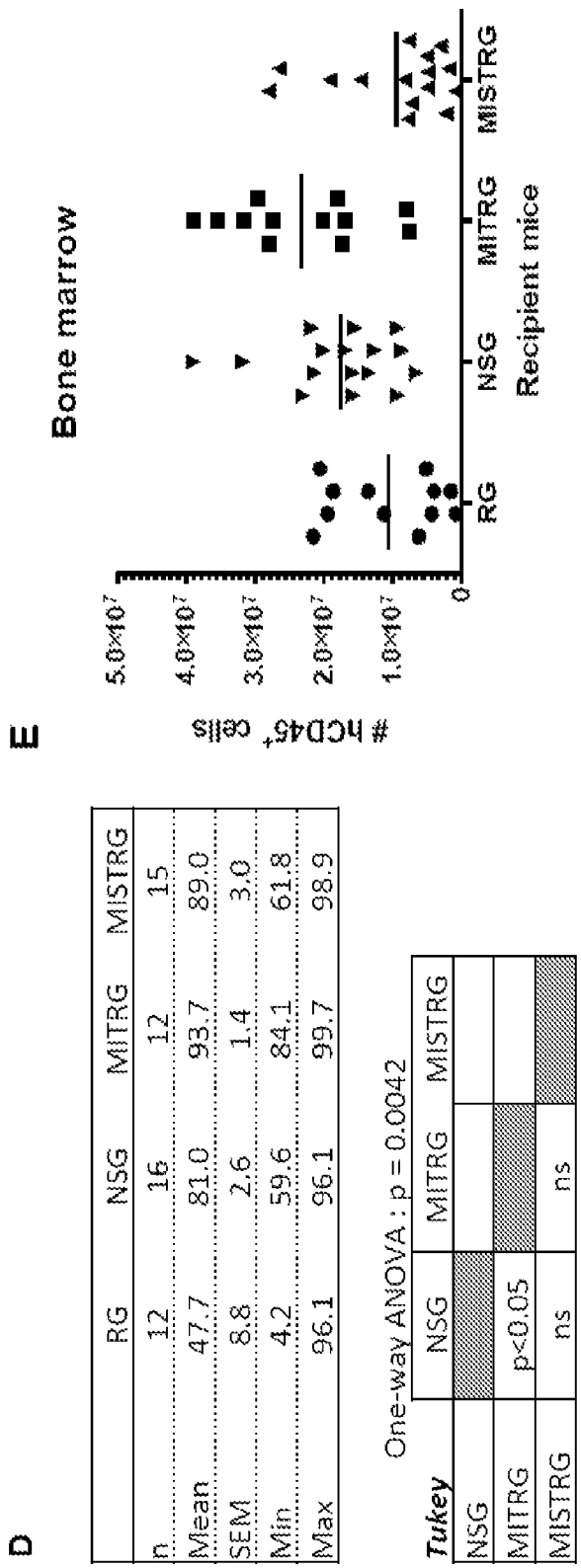

Newborn MISTRG mice and their littermates MITRG (lacking the hSIRPA transgene) were sublethally irradiated and transplanted with human fetal liver-derived CD34+ cells, following a standard protocol (Traggiai et al., 2004, Science 304, 104). RAG2−/− IL2-Rγ−/− (RG) mice that share the same genetic background but lack all the humanized alleles, and commercially available NOD-Scid IL2-Rγ−/− (NSG) mice served as controls. Blood engraftment levels (hCD45+ cell percentage; (FIGS. 1A and 1B; and FIG. 6A) were lower in RG and higher in NSG recipients as previously reported (Strowig et al., 2011, Proceedings of the National Academy of Sciences 108, 13218; Brehm et al., 2010, Clinical immunology 135, 84). The percentage of blood hCD45+ cells was similar in MISTRG and in NSG. Blood engraftment was also significantly increased in MITRG compared to RG, suggesting that the combined humanization of genes overcomes the need to induce phagocytic tolerance through SIRPα/CD47 cross-reactivity (Strowig et al., 2011, Proceedings of the National Academy of Sciences 108, 13218; Takenaka et al., 2007, Nature immunology 8, 1313; Legrand et al., 2011, Proceedings of the National Academy of Sciences 108, 13224), possibly by weakening the mouse innate response. Mice with at least 10% human CD45+ cells in the blood were selected for further experimentation (FIG. 6B). In the bone marrow (BM), the percentages of hCD45+ cells exceeded 90% and reached up to 99% in the majority of both MISTRG recipients (FIGS. 1A and 1C; and FIGS. 6C to 6E), and the high efficiency of engraftment in the BM was independent of SIRPα/CD47 interaction. To test the capacity of humanized cytokines to support human hematopoiesis in more competitive conditions, human CD34+ cells were transplanted into non-irradiated MISTRG. This protocol resulted in human CD45+ cells in the blood and BM of all recipients (FIGS. 1D and 1E) and remarkably, half of the mice showed chimerism as high as the highest levels measured in recipients engrafted after X-ray pre-conditioning (compare FIG. 1E to FIGS. 1B and 1C). The data described herein show that the genetic replacement of multiple cytokines in MISTRG creates a microenvironment in which human hematopoiesis can almost completely displace mouse hematopoiesis in the bone marrow, and obviate the need for pathology-inducing irradiation.

Figures 2A, 2B, 2C:
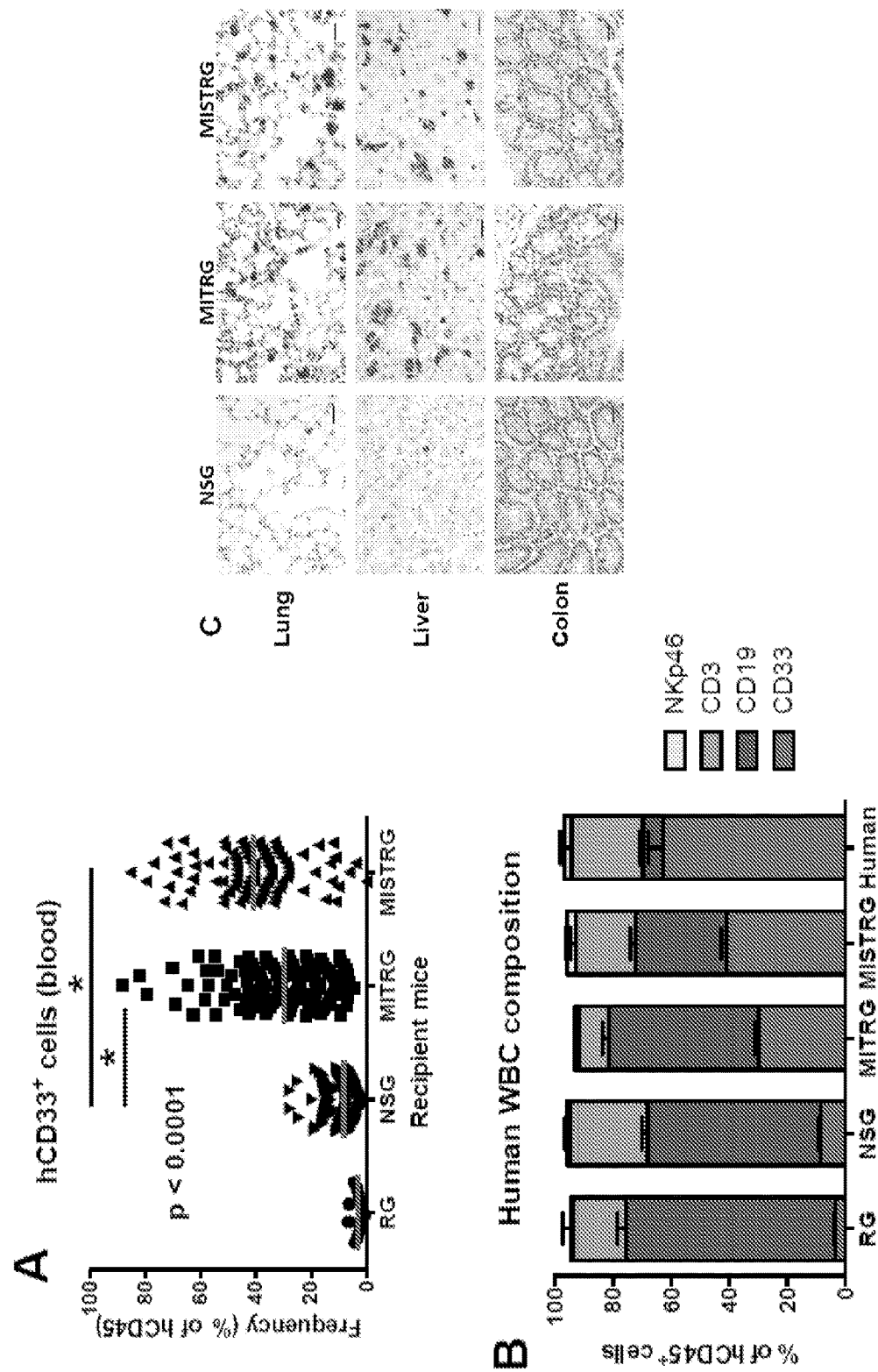
FIGS. 2A-2K, depicts the results of experiments showing that MISTRG mice support efficient myeloid development and maintenance in lymphoid and non-lymphoid tissues.
Figures 2D, 2E:
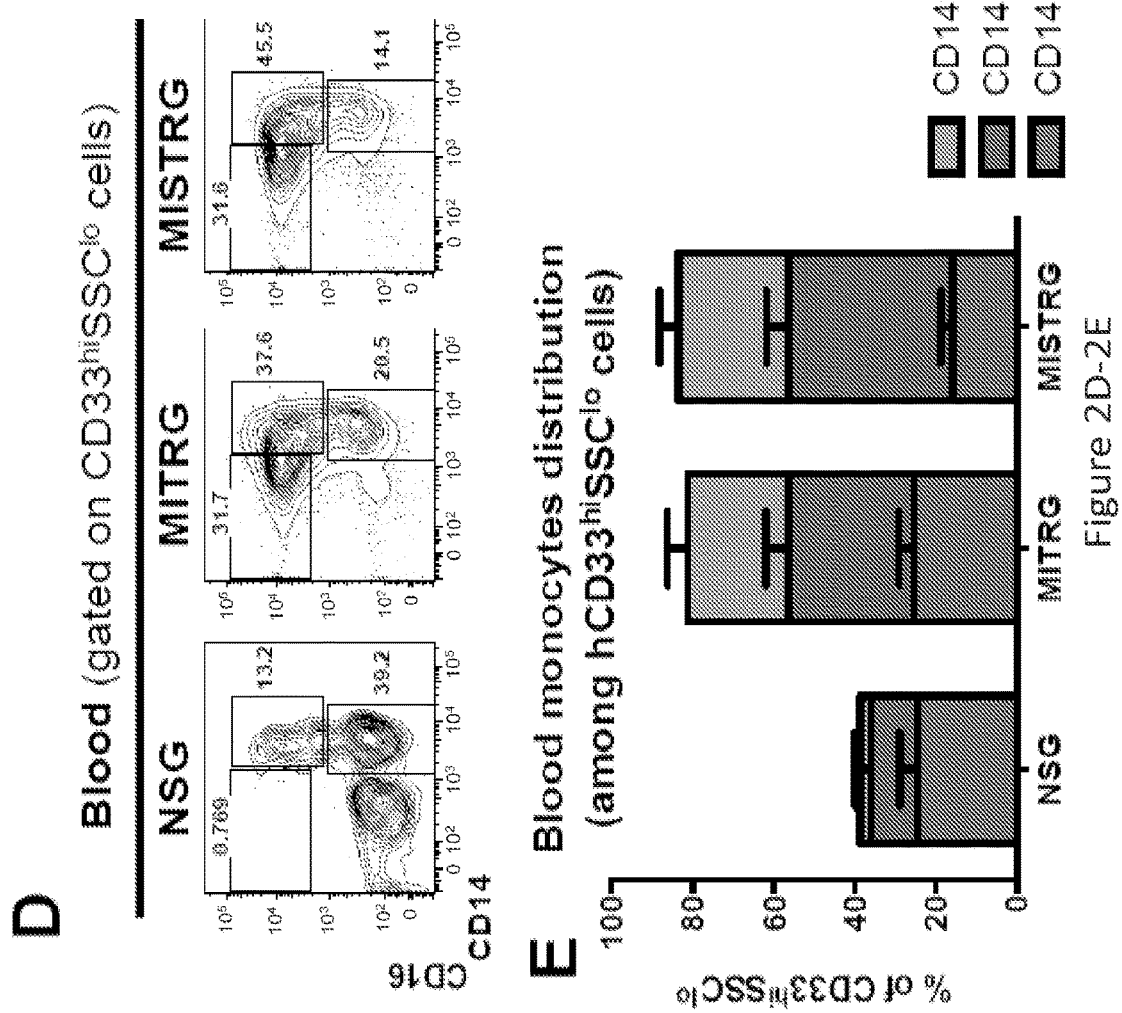
Figures 7A, 7B, 7C, 7D:
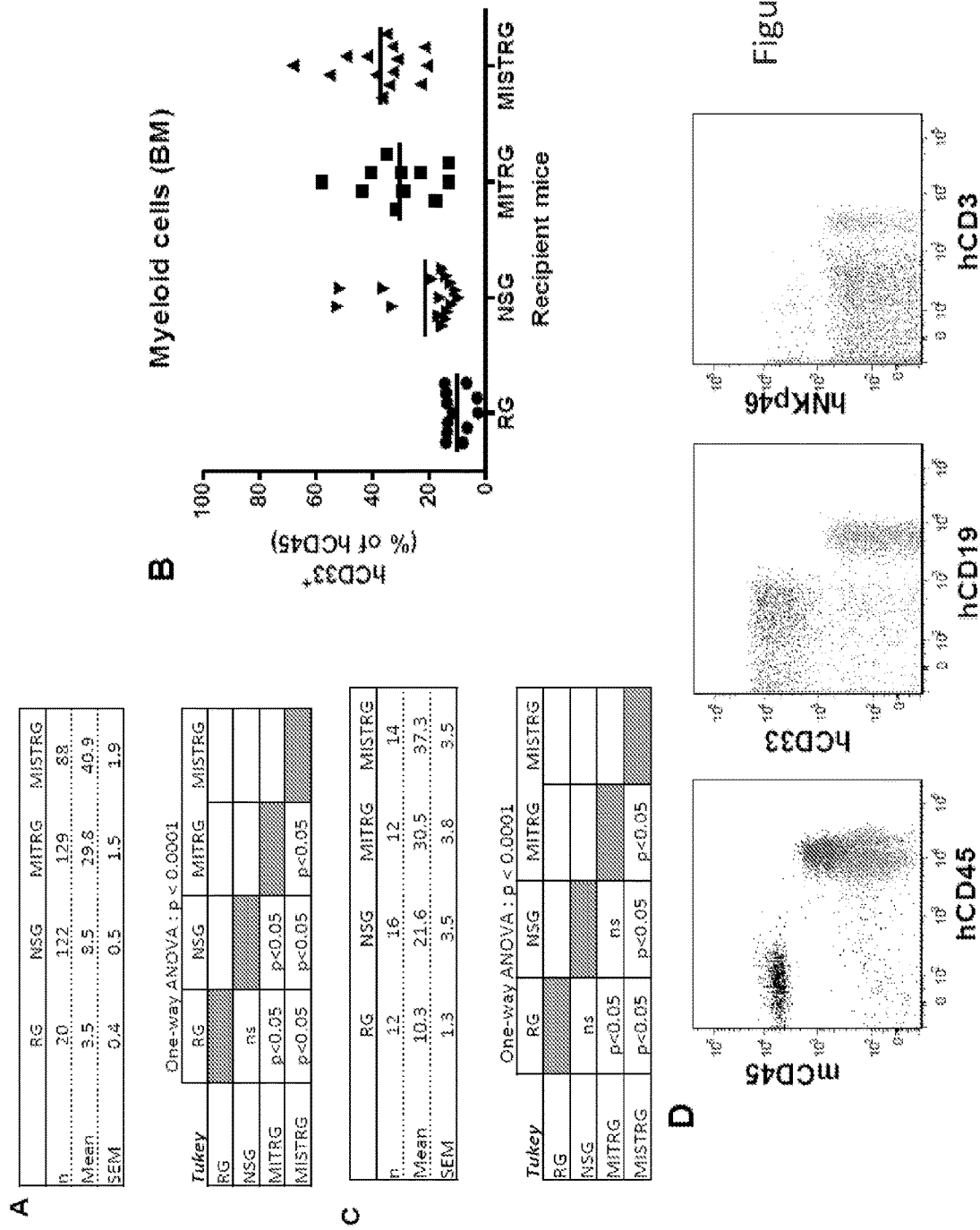
FIGS. 7A-7H, depicts the results of experiments assessing enhanced human myeloid development in MISTRG mice.
Figures 7E, 7F:
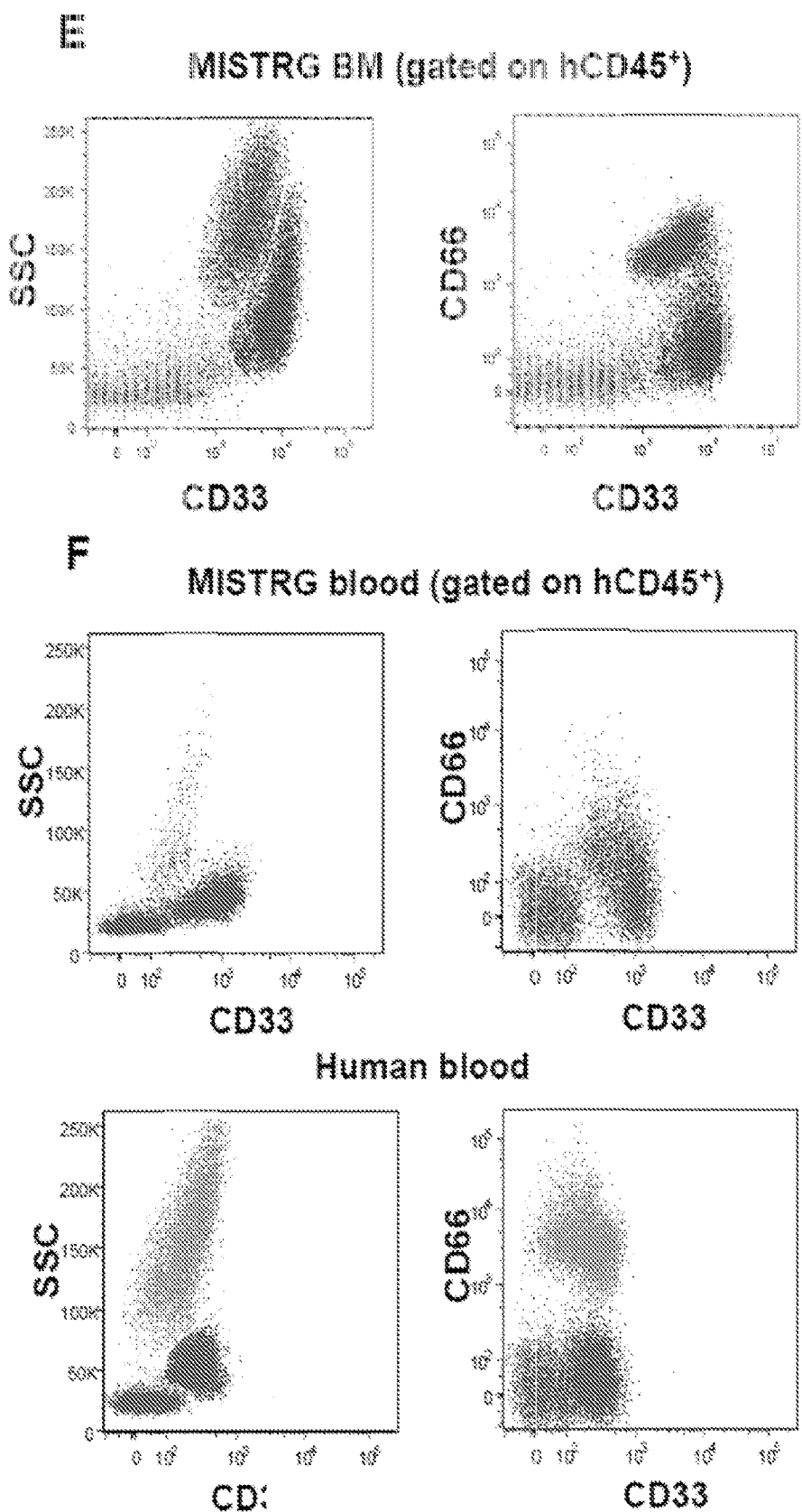
Figures 7G, 7H:
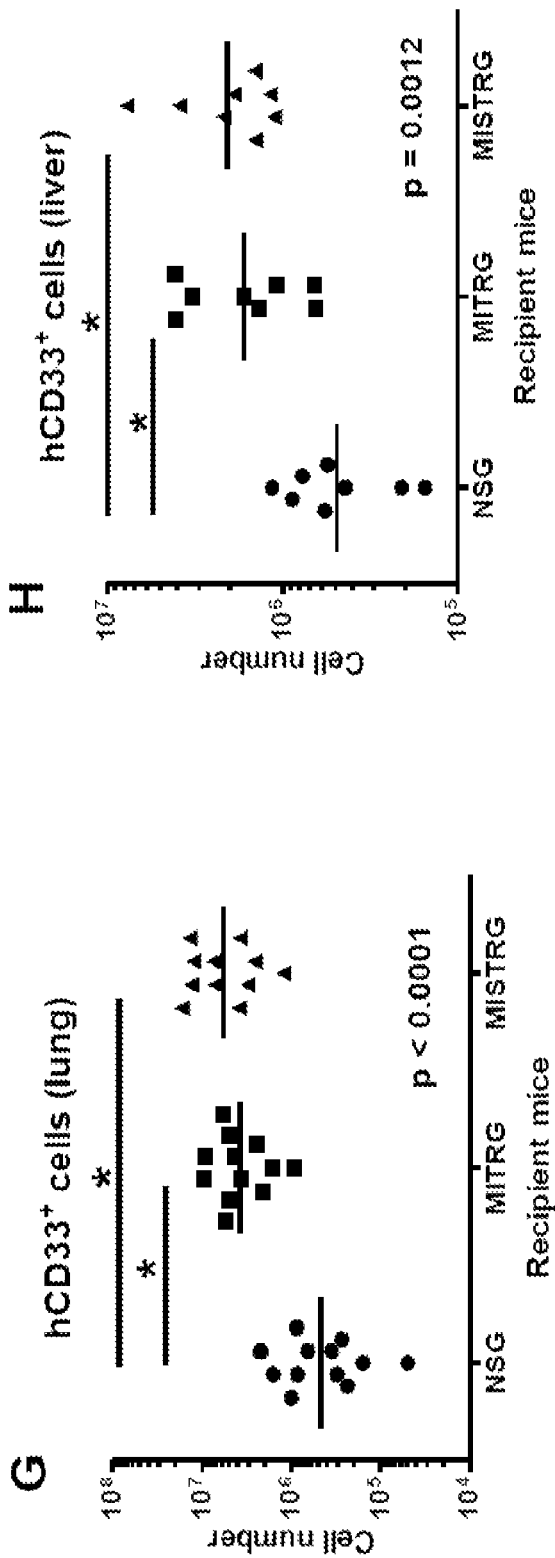
Figure 8A:
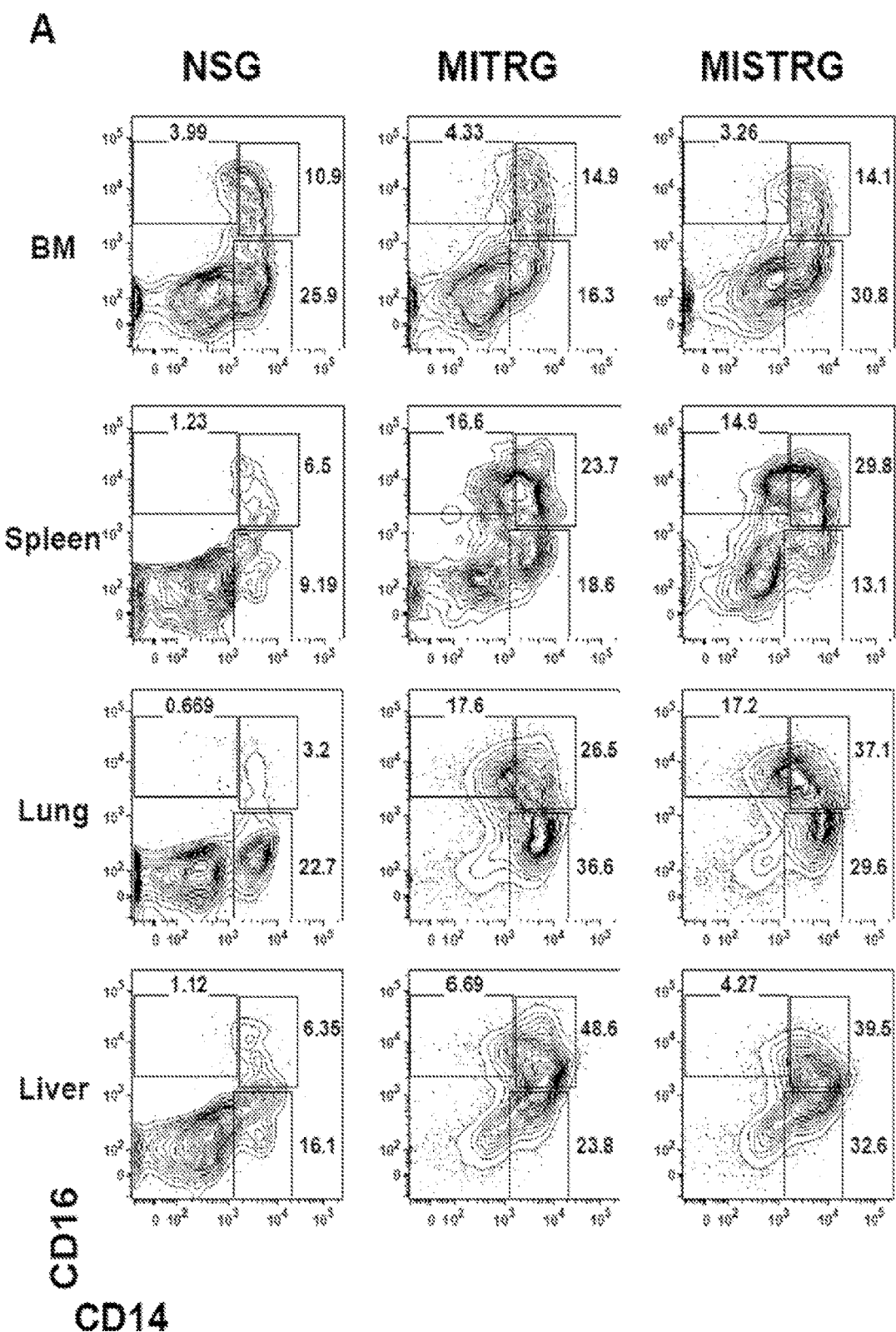
FIGS. 8A and 8B, depicts the results of experiments showing enhanced development of human monocyte subsets in MISTRG mice.
Figure 8B:
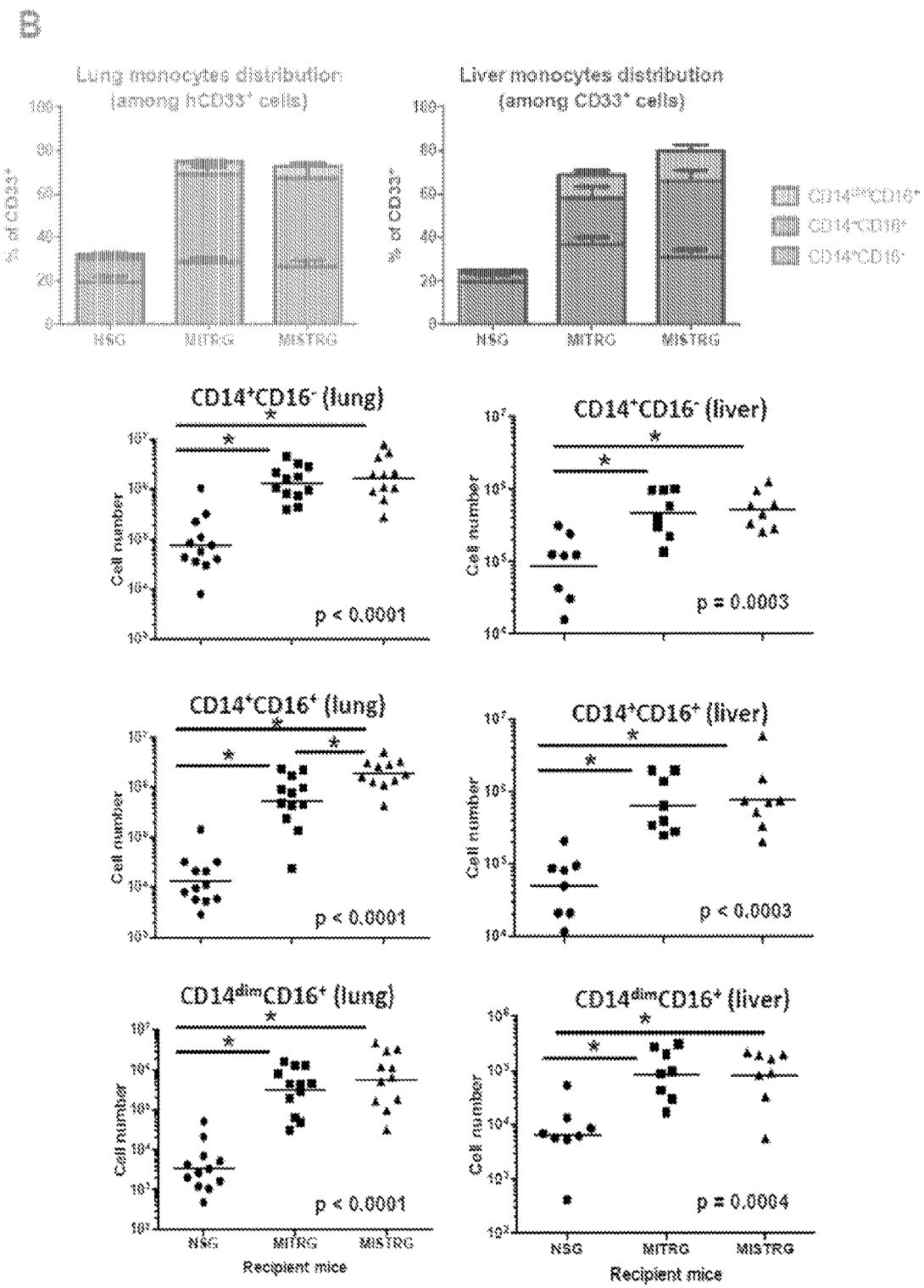

Next, the capacity of MISTRG mice to support human myelopoiesis was assessed. Human myeloid cells (hCD33+) were present in significantly higher proportions in the blood and bone marrow of MISTRG compared to RG and NSG (FIG. 2A; and FIGS. 7A to 7C). The increased proportion of myeloid cells in MISTRG resulted in a blood composition that resembles the physiological composition of human blood, which is rich in myeloid cells and radically different from that of lymphoid-rich mouse blood (Mestas and Hughes, 2004, Journal of Immunology 172, 2731; Rongvaux et al., 2013, Annual review of immunology 31, 6354) (FIG. 2B; and FIG. 7D). While both monocytes (CD33hiSSCloCD66−) and granulocytes (CD33+SSChiCD66+) were present in the BM (FIG. 7E), human myeloid cell populations in peripheral blood were composed mostly of monocytes (FIG. 7F), suggesting that the terminal differentiation and egress from the BM or peripheral survival of human granulocytes is still suboptimal in this mouse environment. Importantly however, human myeloid cells were present in high numbers in non-lymphoid tissues such as lung, liver and colon of MISTRG as shown by immunohistochemistry (hCD68+ cells; (FIG. 2C) or by flow cytometry (hCD33+; FIGS. 7G and 7H), and significantly exceeded human myeloid cell numbers found in NSG mice by a factor of ~10.

Figures 2F, 2G, 2H:
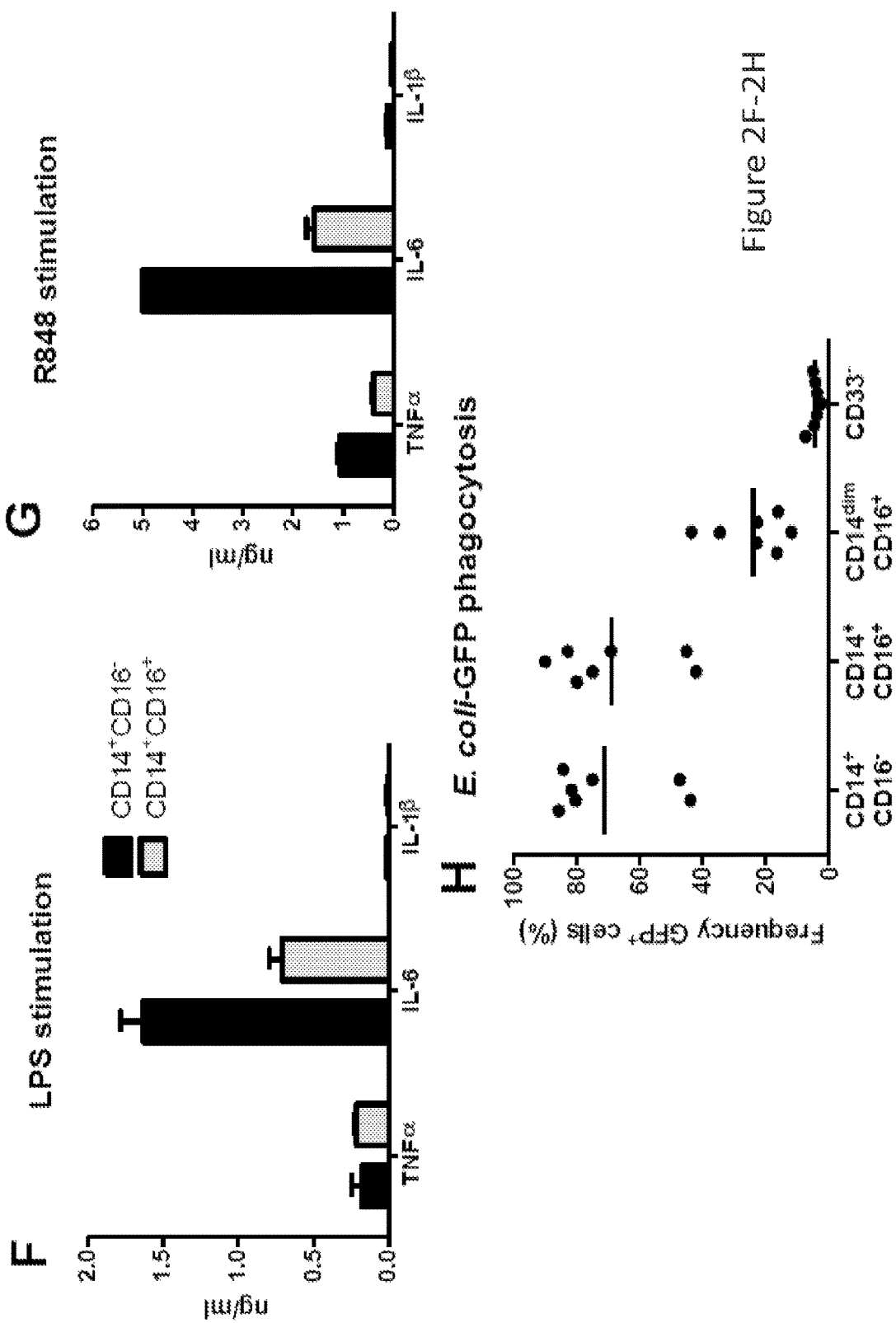
Figures 2I, 2J, 2K:
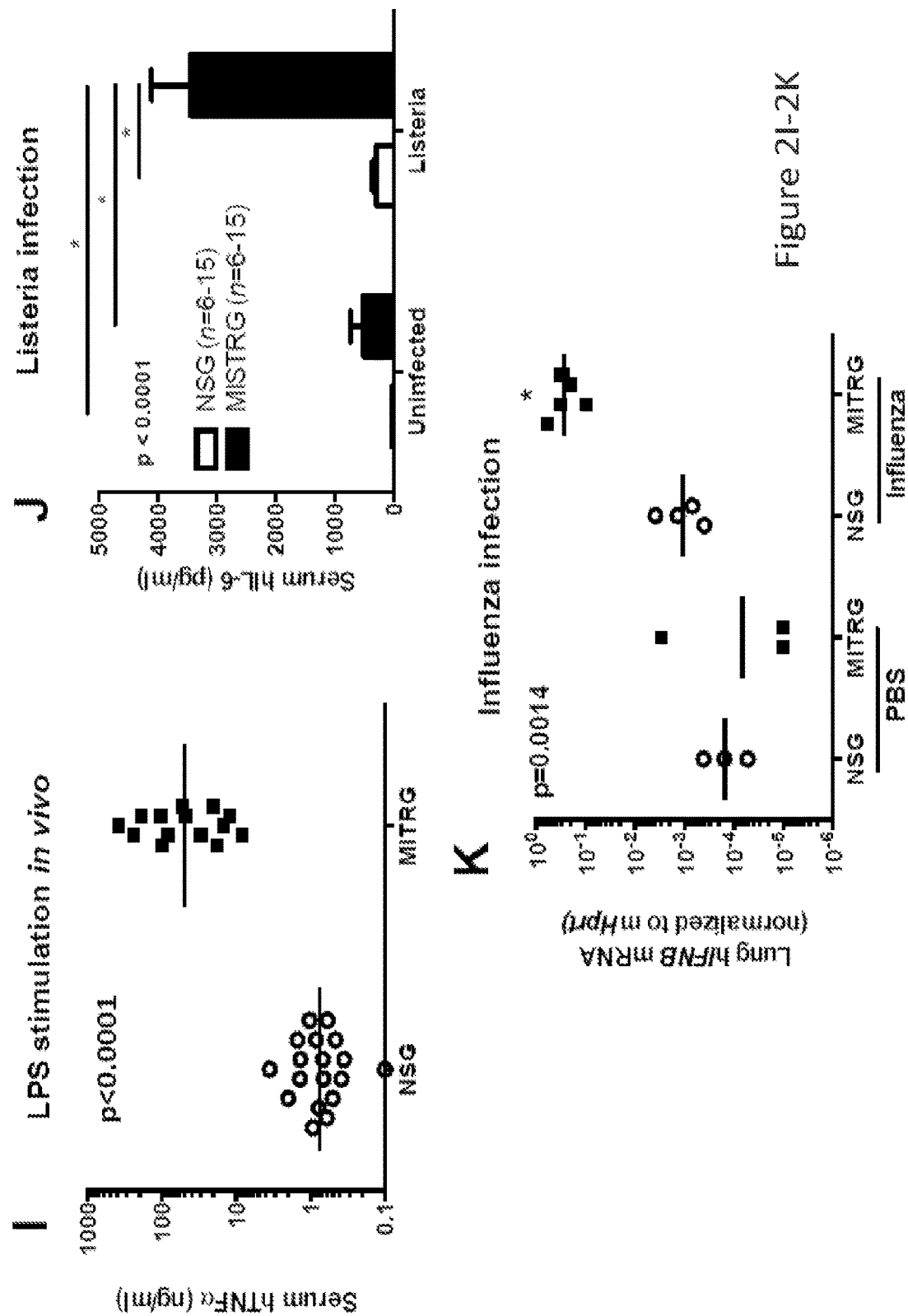
Figure 9A:
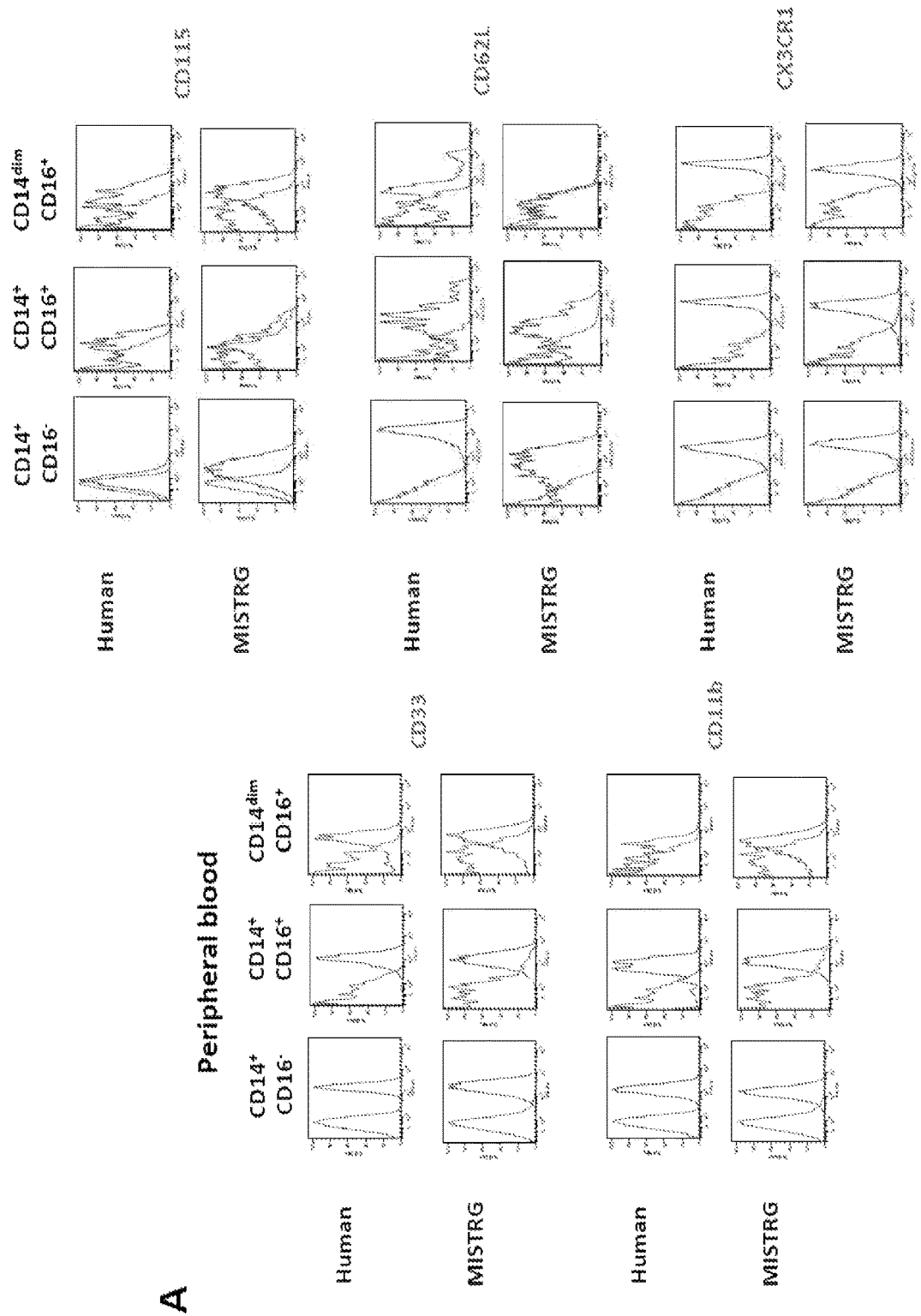
FIGS. 9A and 9B, depicts the results of experiments showing that human monocyte subsets are similar in MISTRG and in human donors. Extended immunophenotype of the indicated subsets of human monocytes in the blood (FIG. 9A) and BM (FIG. 9B) of MISTRG recipients and human donor. Staining with isotype control antibodies and specific antibodies is shown.
Figure 9B:
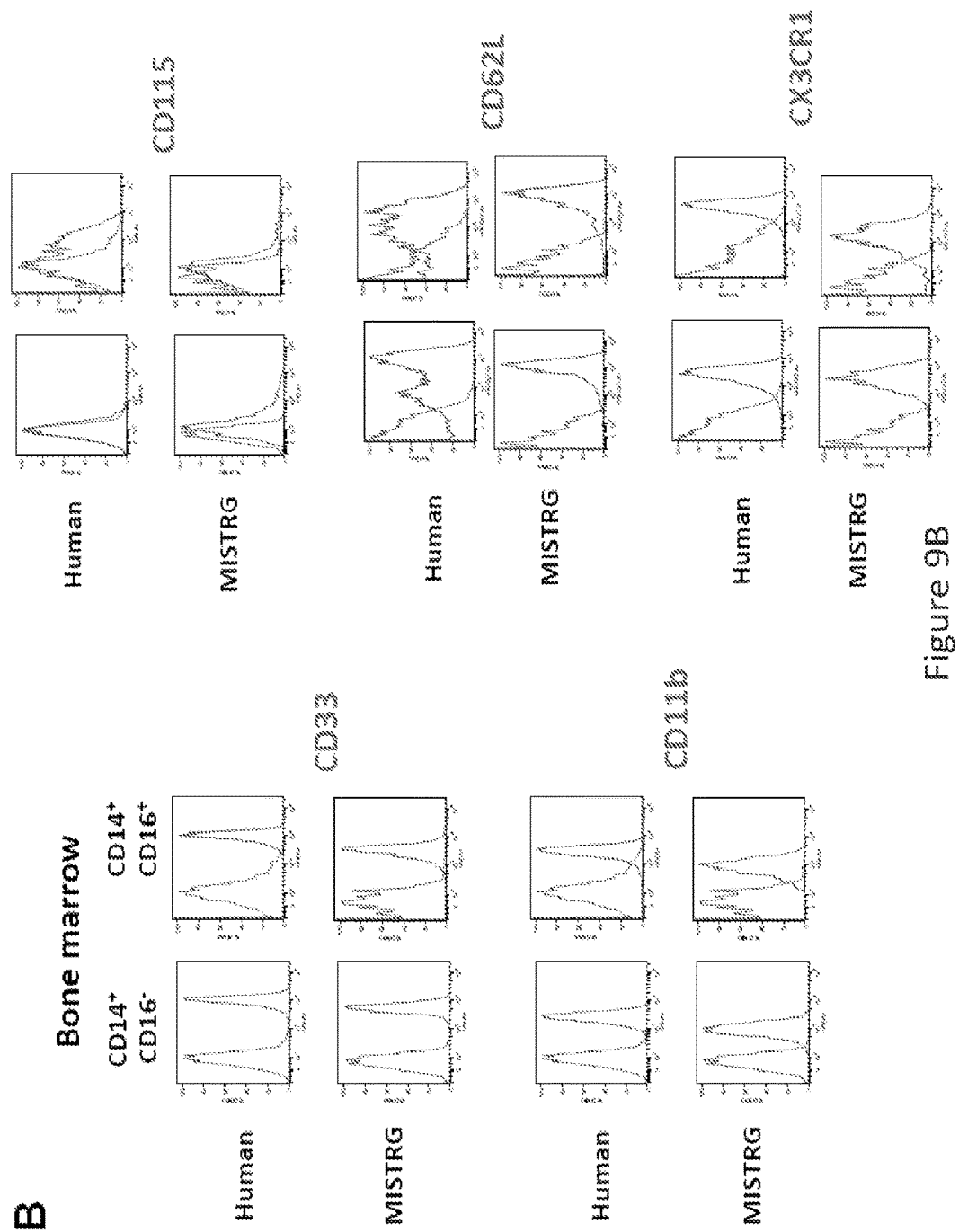
Figures 10A, 10B, 10C:
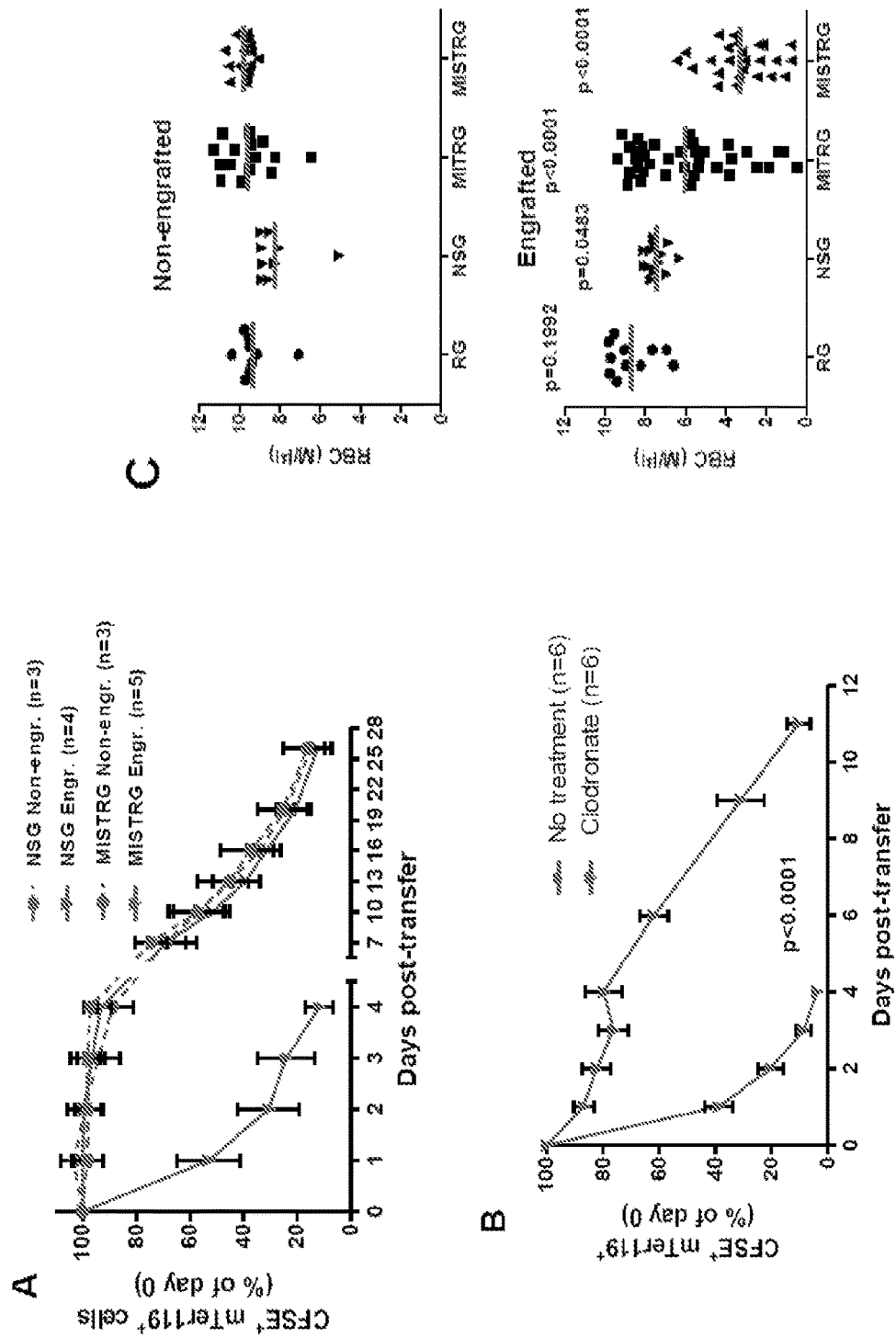
FIGS. 10A-10I, depicts the results of experiments showing that human myeloid cells breach human-to-mouse phagocytic tolerance.
Figures 10D, 10E, 10F:
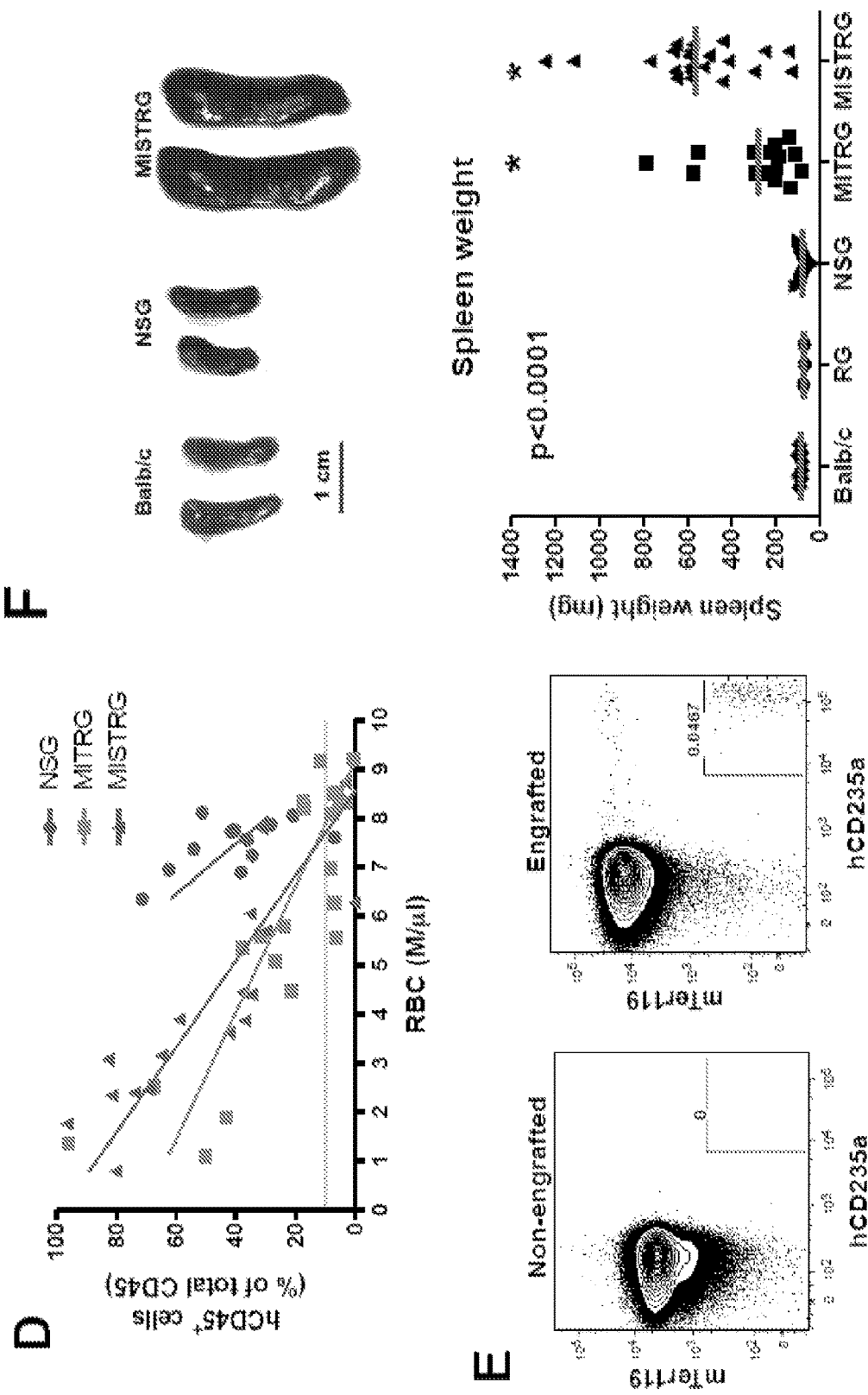
Figures 10G, 10H, 10I:
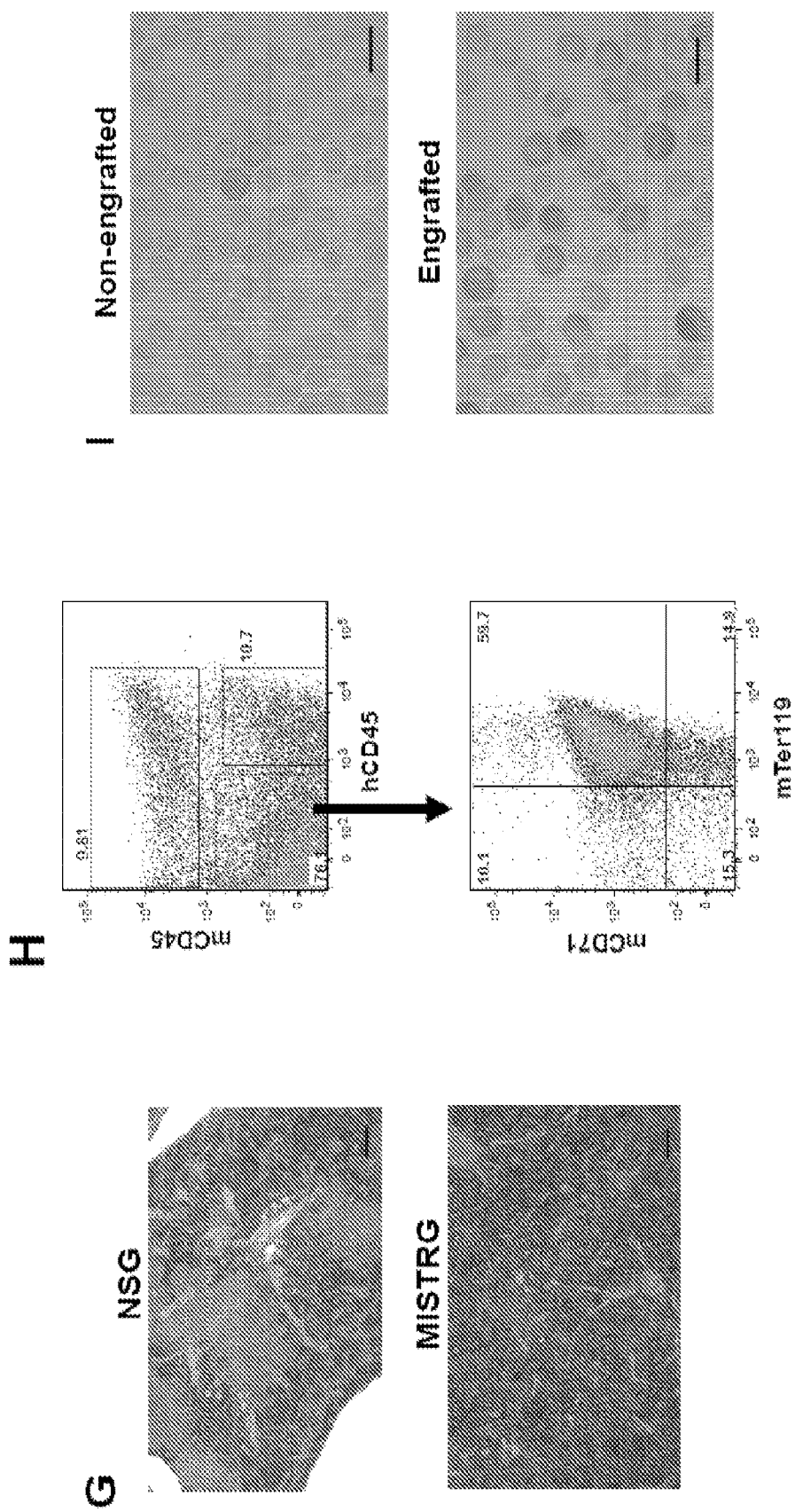

In humans, three subsets of monocytes have been phenotypically and functionally described, based on the expression of the CD14 and CD16 markers (Auffray et al., 2009, Annual review of immunology 27, 669; Cros et al., 2010, Immunity 33, 375). All three subpopulations of human monocytes (CD14+CD16−, CD14+CD16+ and CD14dimCD16+) were present in the lymphoid and non-lymphoid tissues, such as lung and liver, of MISTRG (FIGS. 2D and 2E; and FIGS. 8A and 8B). In contrast in NSG, in addition to the lower frequency of myeloid cells, only CD14+CD16− and to some extent CD14+CD16+ monocytes could be consistently detected, while CD14dimCD16+ cells were only marginally represented. The extended immunophenotype (CD33, CD11b, CD115, CD62L and CX3CR1) of the monocyte subpopulations found in MISTRG compared closely to the equivalent subsets in human peripheral blood (FIG. 9). Human CD14+CD16− and CD14+CD16+ monocytes isolated from the BM of MITRG produced high levels of inflammatory cytokines in response to TLR4 and TLR7/8 ligands (LPS and R848, respectively) (FIGS. 2F and sG). In an in vitro assay performed on WBCs of MITRG, both CD14+CD16− and CD14+CD16+ cells had a high capacity to phagocytose GFP-expressing E. coli, while CD14dimCD16+ monocytes had limited phagocytic ability (FIG. 2H), again reflecting the physiological properties of the corresponding subpopulations in human blood (Cros et al., 2010, Immunity 33, 375). When challenged in vivo with LPS or infected with the bacterial and viral human pathogens Listeria monocytogenes and influenza A, respectively, MISTRG mice responded with robust production of human inflammatory cytokines (TNFα, IL-6 and IFNγ, respectively), while NSG mice showed significantly lower, about one log lower, responses (FIGS. 2I to 2K). These results demonstrate that the human monocyte subsets that develop in MISTRG are functional in vitro and in vivo. However, a drawback of the presence of functional human phagocytic cells in the mouse is a breach of human-to-mouse phagocytic tolerance, to which mouse RBCs are particularly susceptible (FIGS. 10A and 10B). This destruction of mouse RBCs resulted in anemia (FIGS. 10C to 10I) and limited the lifespan of engrafted mice to 10-12 weeks (MISTRG) or 12-16 weeks (MITRG).

Figures 3A, 3B:
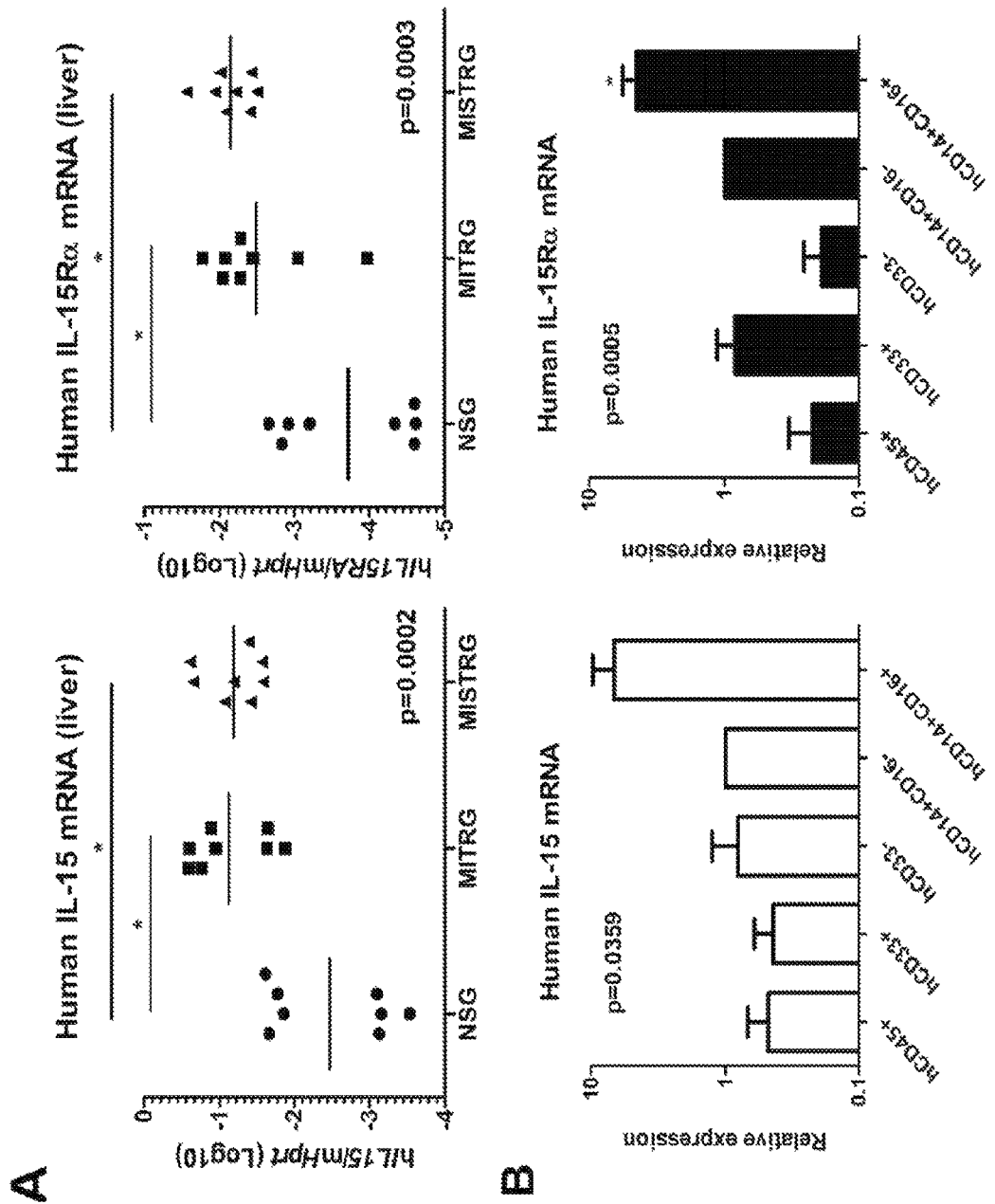
FIGS. 3A-3I, depicts the results of experiments showing that MISTRG mice efficiently support the development and function of human NK cells.
Figure 3C:
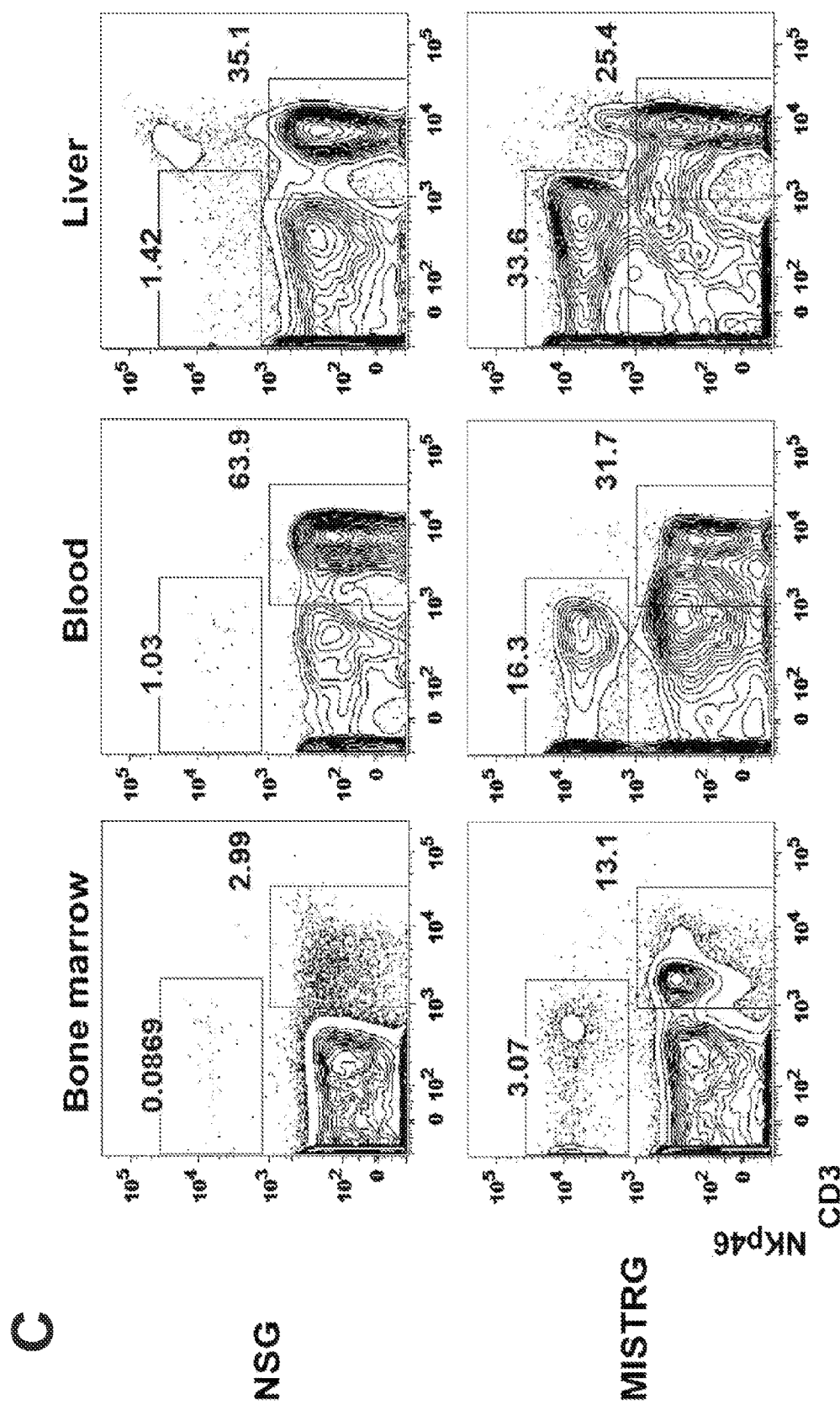
Figures 3D, 3E:
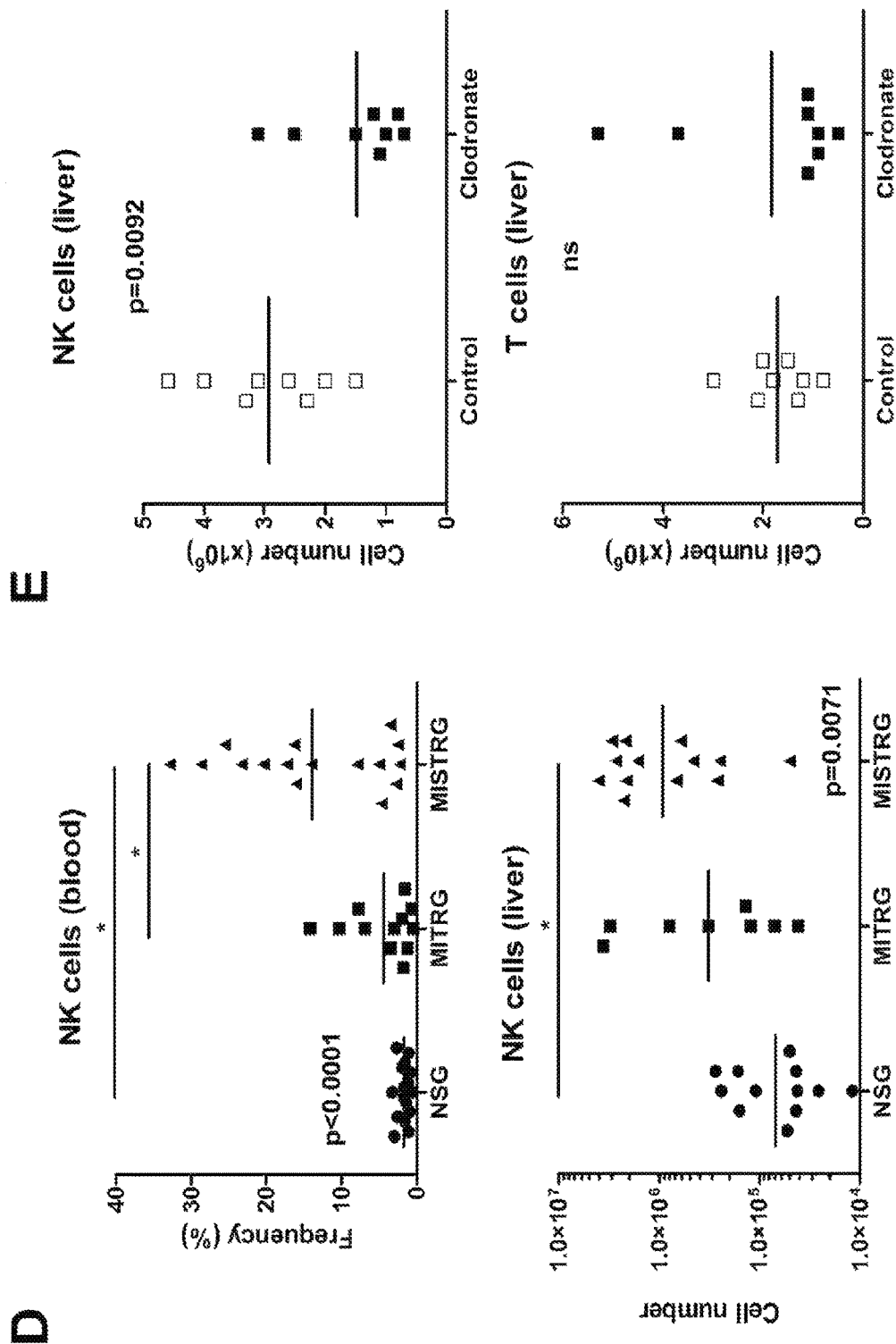
Figures 11A, 11B:
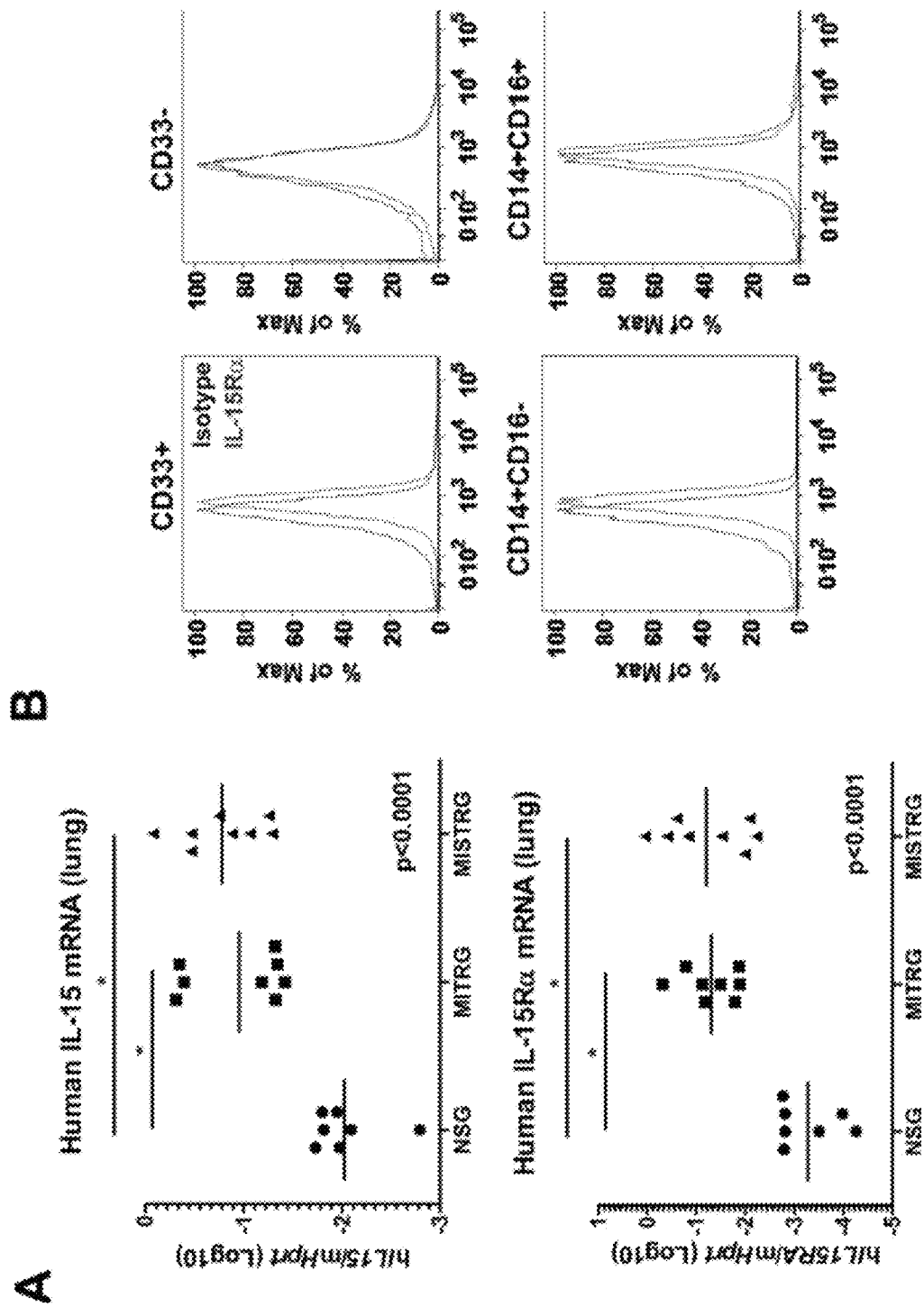
FIGS. 11A and 11B, depicts the results of experiments showing that MISTRG mice provide human IL-15/IL-15Rα.

Myeloid cells can support the development and differentiation of other immune cells through the production of cytokines. Whether the myeloid compartment of MISTRG mice was a source of human cytokines, such as IL-15, was assessed. Consistent with this notion, it was found that mRNA expression of human IL-15 and IL-15Rα was increased by a factor of greater than 10 in MISTRG when compared to NSG (FIG. 3A; and FIG. 11A). To define in more detail the cellular source of human IL-15/IL-15Rα in MISTRG, the abundance of human IL-15 and IL-15Rα transcripts in purified human cell populations was measured. Expression of human IL-15Rα mRNA was higher in human myeloid cells (hCD33+) than in non-myeloid cells (hCD33−) (FIG. 3B). In particular, CD14+CD16+ monocytes showed an enrichment of both IL-15 and IL-15Rα transcripts (FIG. 3B). The expression of human IL-15Rα protein on the surface of human myeloid cells from MISTRG was confirmed by flow cytometry (FIG. 11B).

Figure 12A:
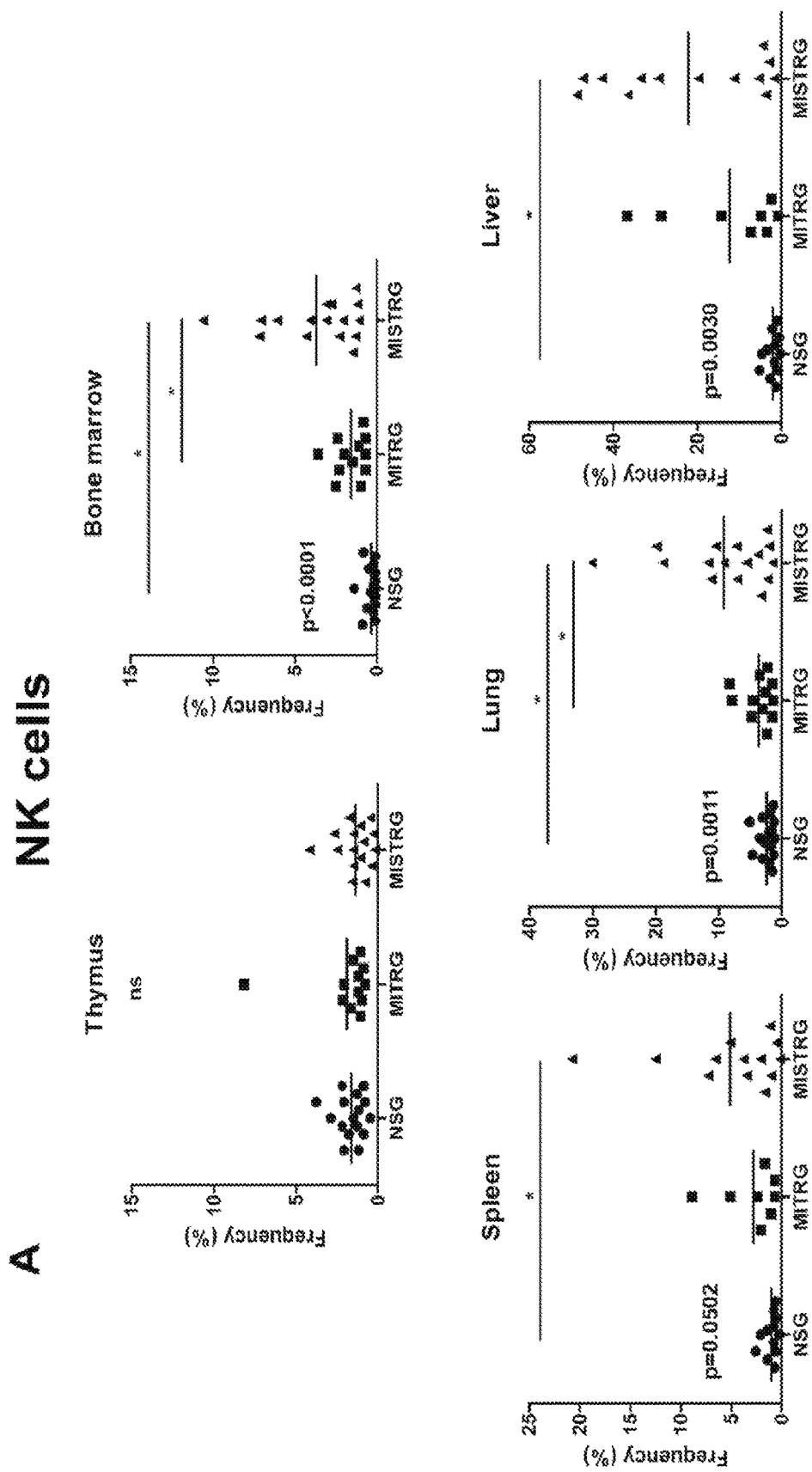
FIGS. 12A and 12B, depicts the results of experiments showing enhanced human NK cell development in MISTRG mice.
Figure 12B:
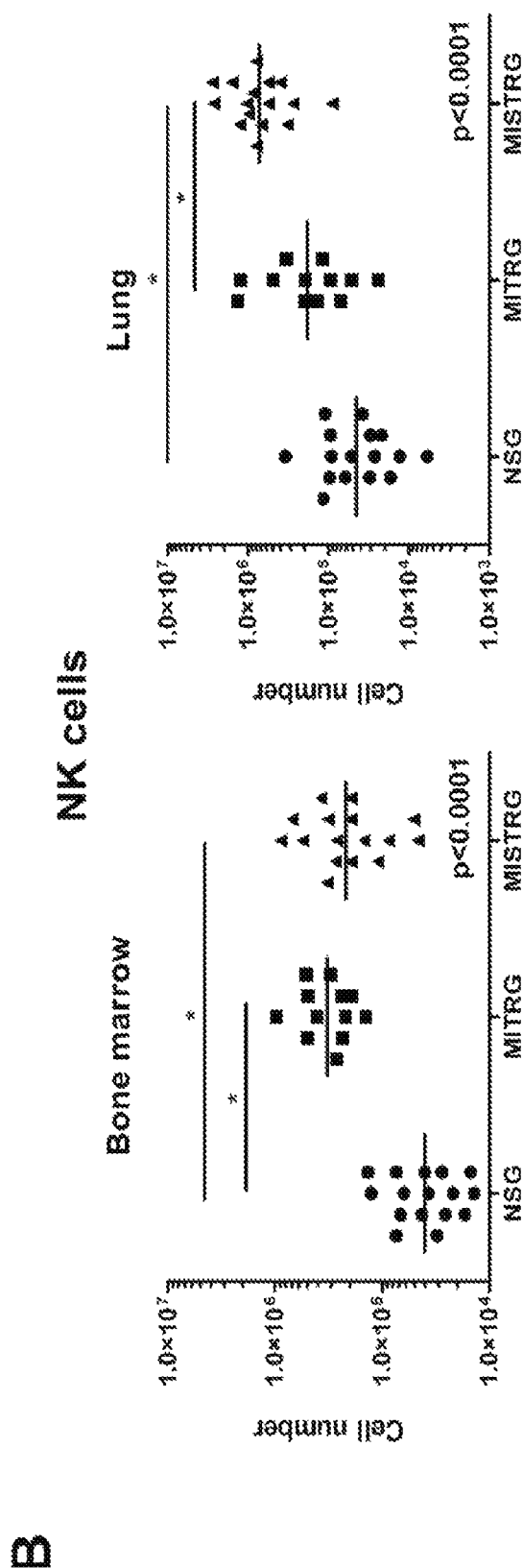
Figure 13A:
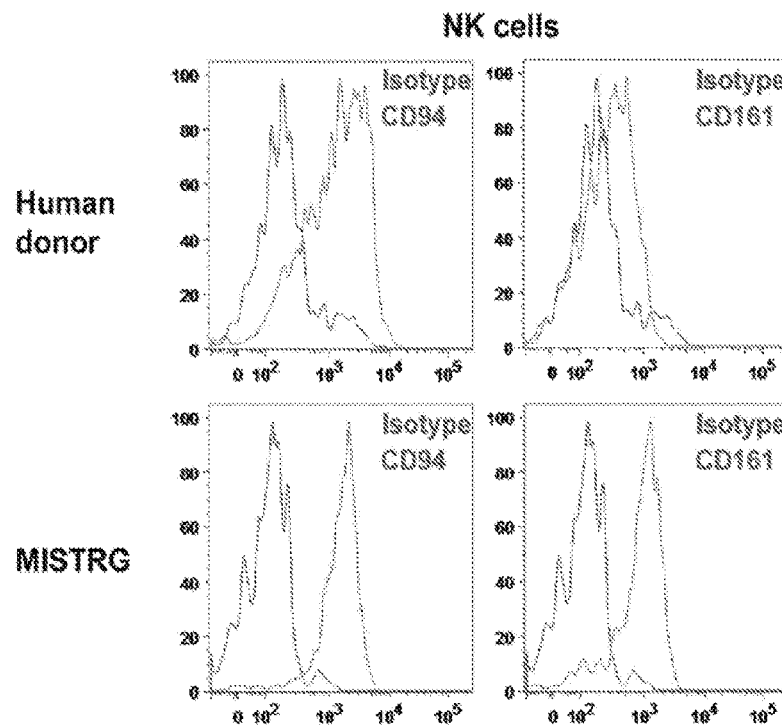
FIGS. 13A-13F, depicts the results of experiments showing that bona fide human NK cells exhibiting enhanced maturation are present in MISTRG mice.
Figure 13B:
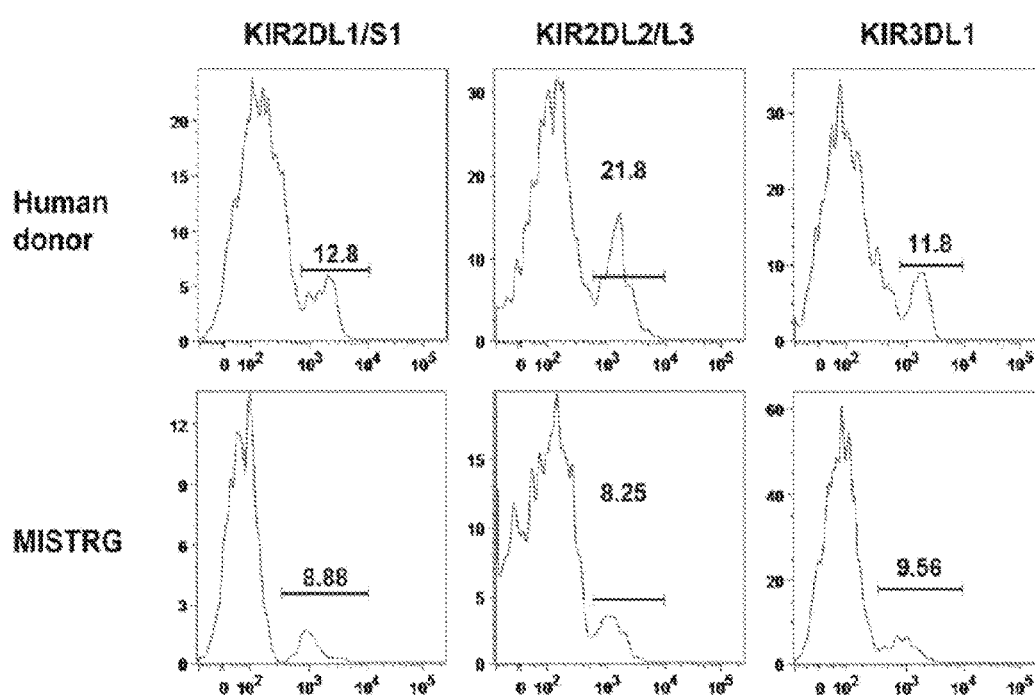
Figure 13C:
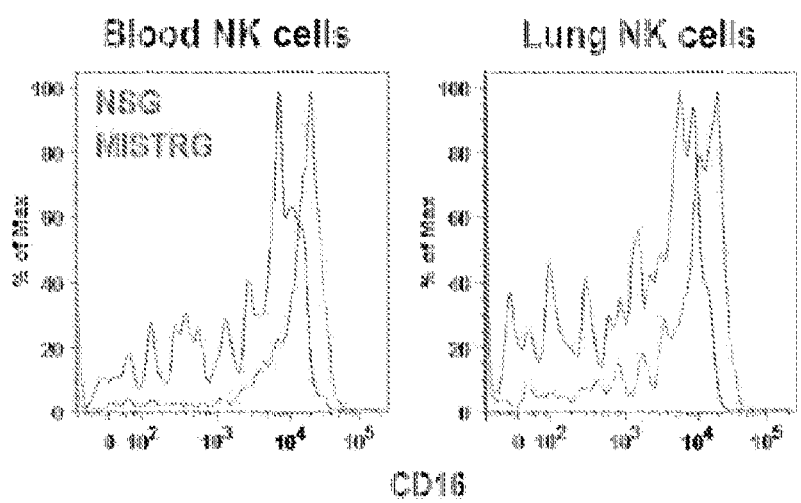
Figure 13D:
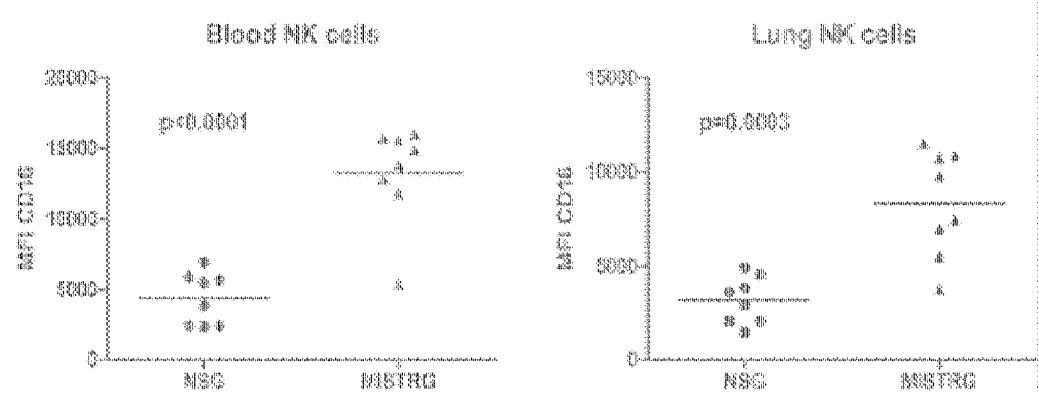
Figure 13E:
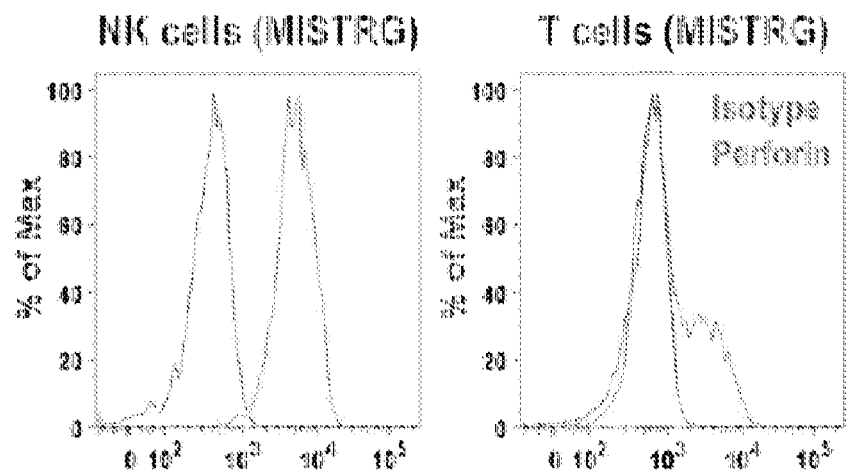
Figure 13F:
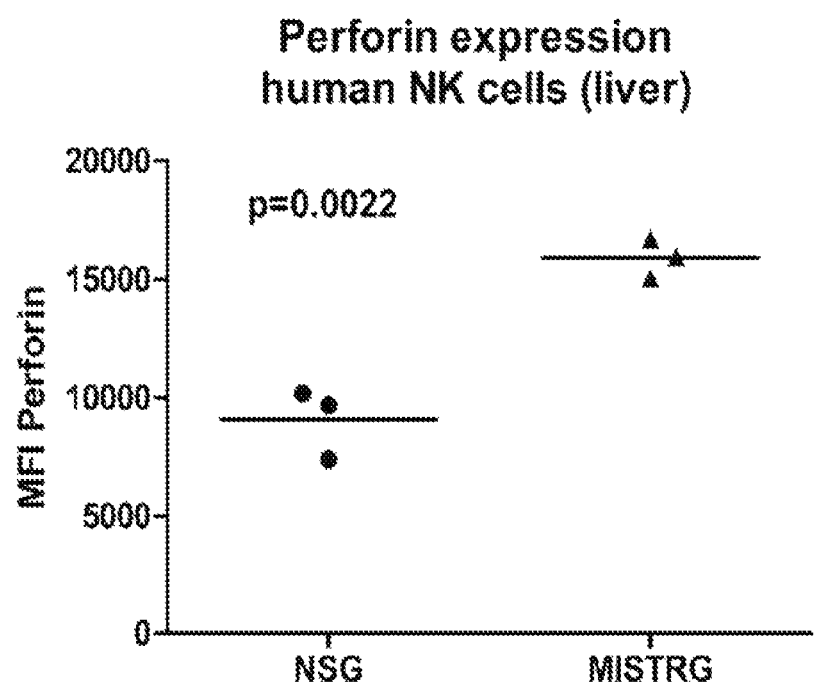

Based on these findings, whether MISTRG mice support the development of human immune cells dependent on IL-15 trans-presentation, such as NK cells (Ma et al., 2006, Annual review of immunology 24, 657; Soderquest et al., 2011, Blood 117, 4511), was assessed. The efficient development of human NK cells in current HHLS mouse models requires the exogenous pharmacologic delivery of human IL-15/IL-15Rα (Huntington et al., 2009, Journal of experimental medicine 206, 25; Chen et al., 2009, Proceedings of the National Academy of Sciences 106, 21783; Pek et al., 2011, Immunobiology 216, 218)23-25) since mouse IL-15 is not sufficient to support human NK cells in vivo. As previously reported (Huntington et al., 2009, Journal of experimental medicine 206, 25; Chen et al., 2009, Proceedings of the National Academy of Sciences 106, 21783; Pek et al., 2011, Immunobiology 216, 218), very few human NK cells (hNKp46+hCD3−) were observed in engrafted NSG (FIGS. 3C and 3D; and FIGS. 12A and 12B). In contrast, human NK cells were readily detected in multiple tissues of engrafted MISTRG and were increased by a factor of ~10 compared to NSG (FIGS. 3C and 3D; and FIGS. 12A and 12B). Apart from the bone marrow, MITRG had less human NK cells than MISTRG, which is most likely due to the previously reported requirement for human SIRPα for the survival of human NK cells in the periphery (Legrand et al., 2011, Proceedings of the National Academy of Sciences 108, 13224). The hNKp46+hCD3− cells in MISTRG mice represented bona fide NK cells because they expressed the typical NK cell surface markers CD94, CD161, and killer inhibitory receptors (KIRs) closely mimicking human controls (FIGS. 12A and 12B). In addition to its effect on development, IL-15 also promotes the maturation of NK cells. Consistently, it was found that surface expression of the maturation marker CD16 and the amounts of the lytic granule protein perforin were higher on NK cells from MISTRG compared to NSG (FIGS. 13C to 13F).

Figure 14:
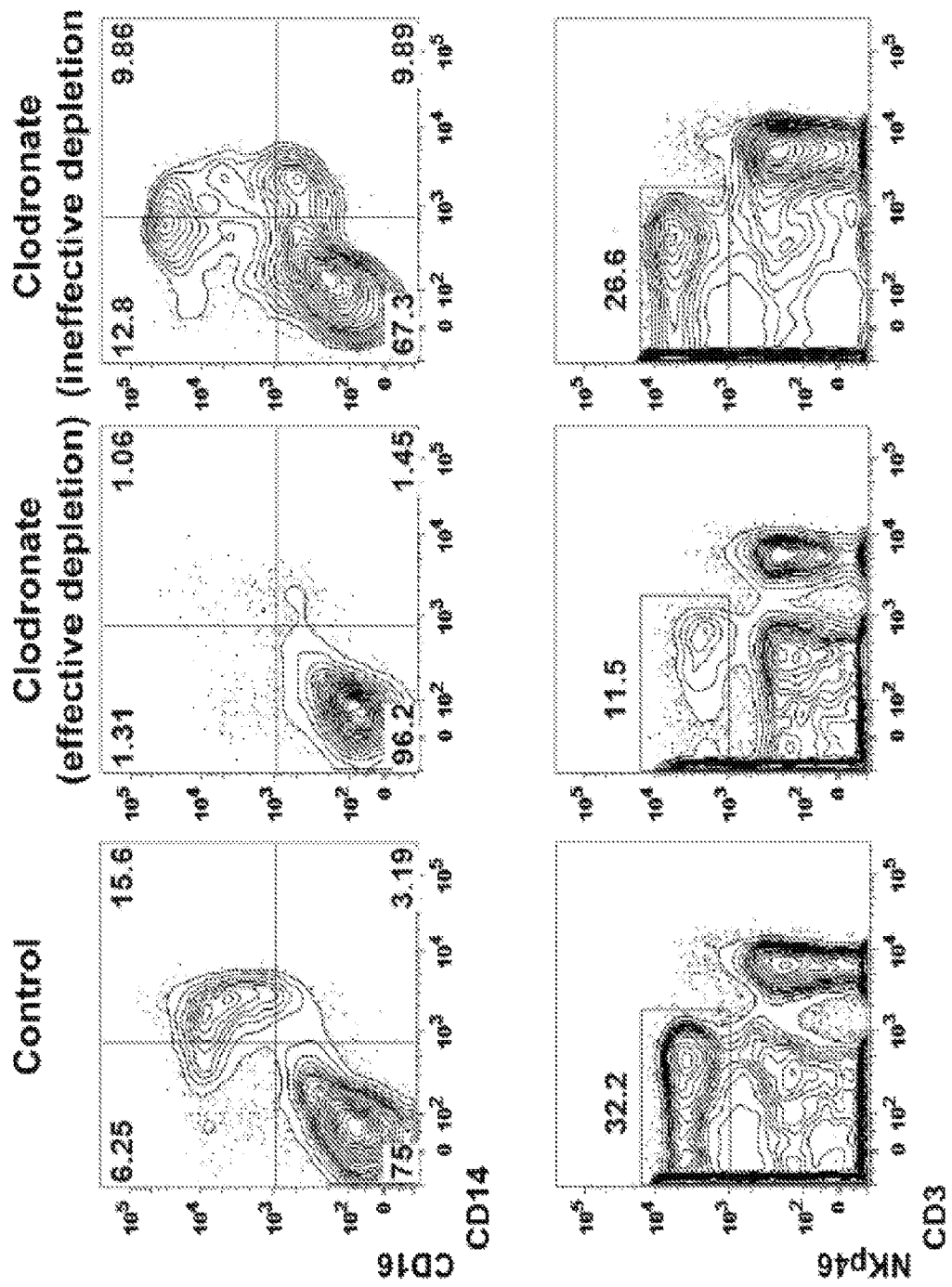
FIG. 14 depicts the results of experiments showing the effect of human monocyte/macrophage depletion on human NK cell homeostasis in MISTRG mice. Engrafted MISTRG mice were left untreated or treated for 3 consecutive days with liposome-encapsulated clodronate to deplete phagocytic cells. Flow cytometry analysis of human monocytes/macrophages (upper panel, gated on hCD33+ cells) and NK cells (hNKp46+hCD3−) in liver (n=8) is shown. Results are representative of two experiments. In 1 out of 8 mice, the clodronate-depletion of monocytes/macrophages was not effective, and no reduction in NK cell number was observed in that mouse.

The cellular source of IL-15 trans-presentation in vivo in humans is currently unknown, but human myeloid cells can support human NK cell proliferation in vitro (Huntington et al., 2009, Journal of experimental medicine 206, 25). To test if trans-presentation of human IL-15 by human monocytes/macrophages underlies the improved human NK cell development in MISTRG, the mice were treated with liposome-encapsulated clodronate to deplete phagocytic cells (FIG. 14). The depletion of phagocytic cells also induced a significant reduction of human NK cells (FIG. 3E), suggesting that human monocytes/macrophages are indeed a critical cell type that trans-presents IL-15 to support human NK cell homeostasis in vivo.

Figures 3F, 3G, 3H, 3I:
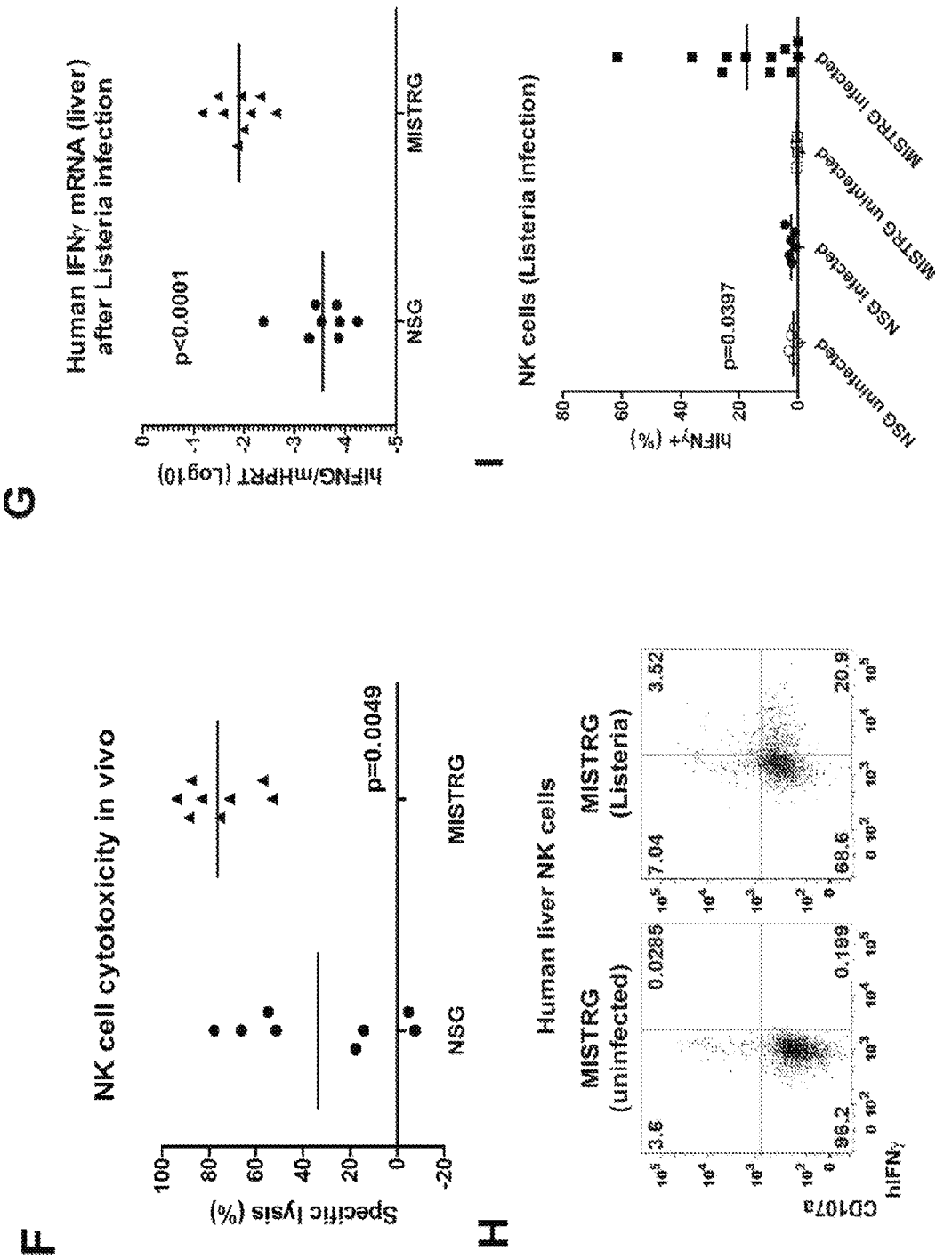

NK cells participate in the innate defense against pathogens by killing cells that lack the expression of MHC class I (missing-self) (Raulet, 2006, Seminars in immunology 18, 145), and by producing the key cytokine IFNγ (Vivier et al., 2008, Nature immunology 9, 503). Consistent with higher perforin expression (FIGS. 13E and 13F), significantly enhanced NK cell cytotoxic activity against human cells lacking MHC class I was observed in vivo in MISTRG compared to NSG (FIG. 3F). NK cells are an early source of IFNγ after Listeria infection. Accordingly, it was found that expression of human IFNγ mRNA in the liver was more than 10-fold higher in MISTRG than in NSG two days post-infection (FIG. 3G). At single-cell resolution, NK cells from Listeria-infected MISTRG showed production of human IFNγ without ex vivo restimulation (FIG. 3H), at frequencies significantly higher than in NSG (FIG. 3I). NK cells in MISTRG also had lytic activity (degranulation) after Listeria infection, as shown by plasma membrane exposure of CD107a (FIG. 3H). Overall, MISTRG via efficient production of human myeloid cells support the development, differentiation, and function of human NK cells, thereby overcoming one major limitation of current HHLS mouse models.

Figures 4A, 4B, 4C:
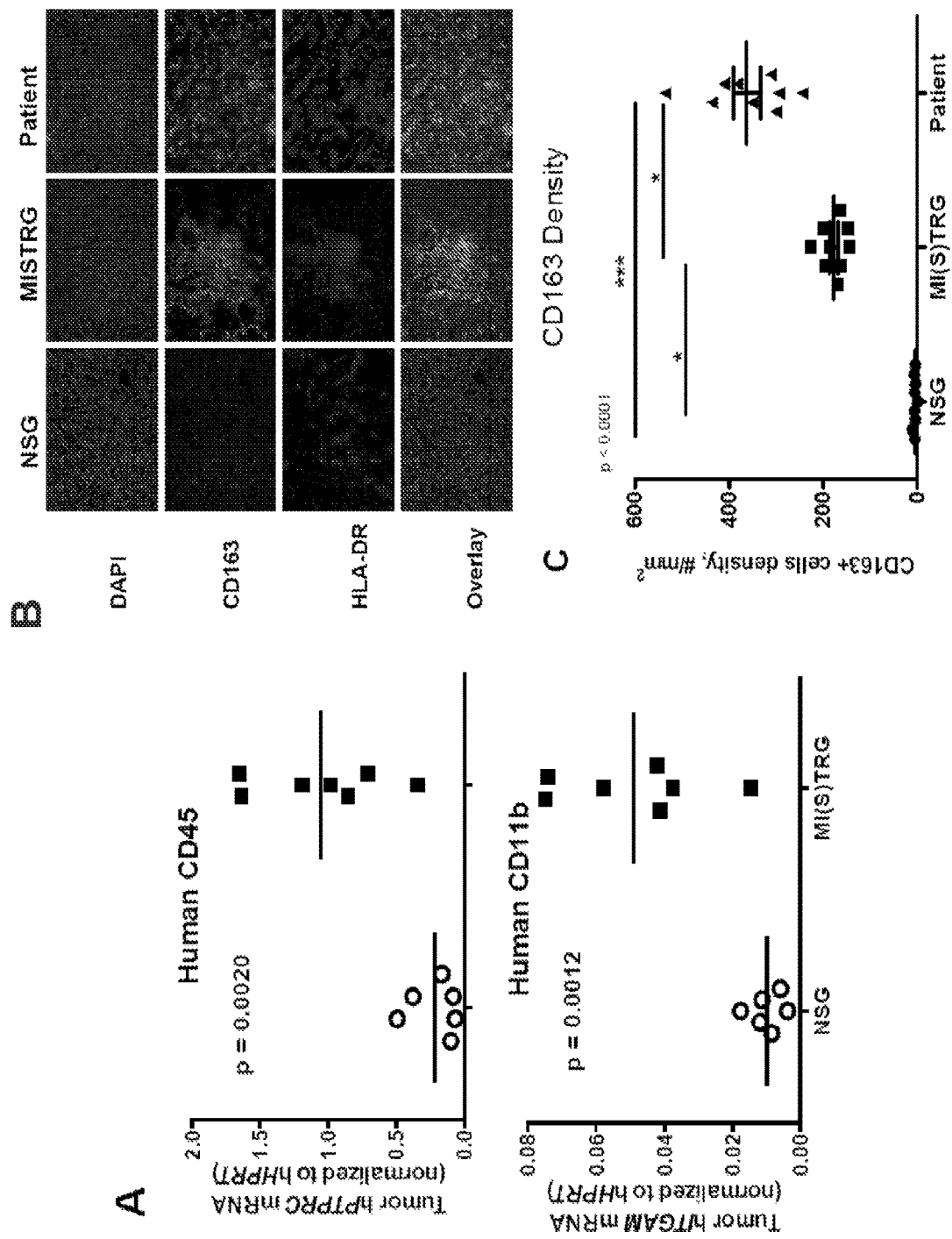
FIGS. 4A-4F, depicts the results of experiments showing that human myeloid cells in MISTRG infiltrate a tumor and support its growth. The human melanoma cell line Me290 was implanted in the flank of engrafted or non-engrafted NSG and MISTRG mice. Some mice were treated with the VEGF-inhibitor Avastin™. The tumors were measured and dissected for analysis 11 days later.
Figure 15:
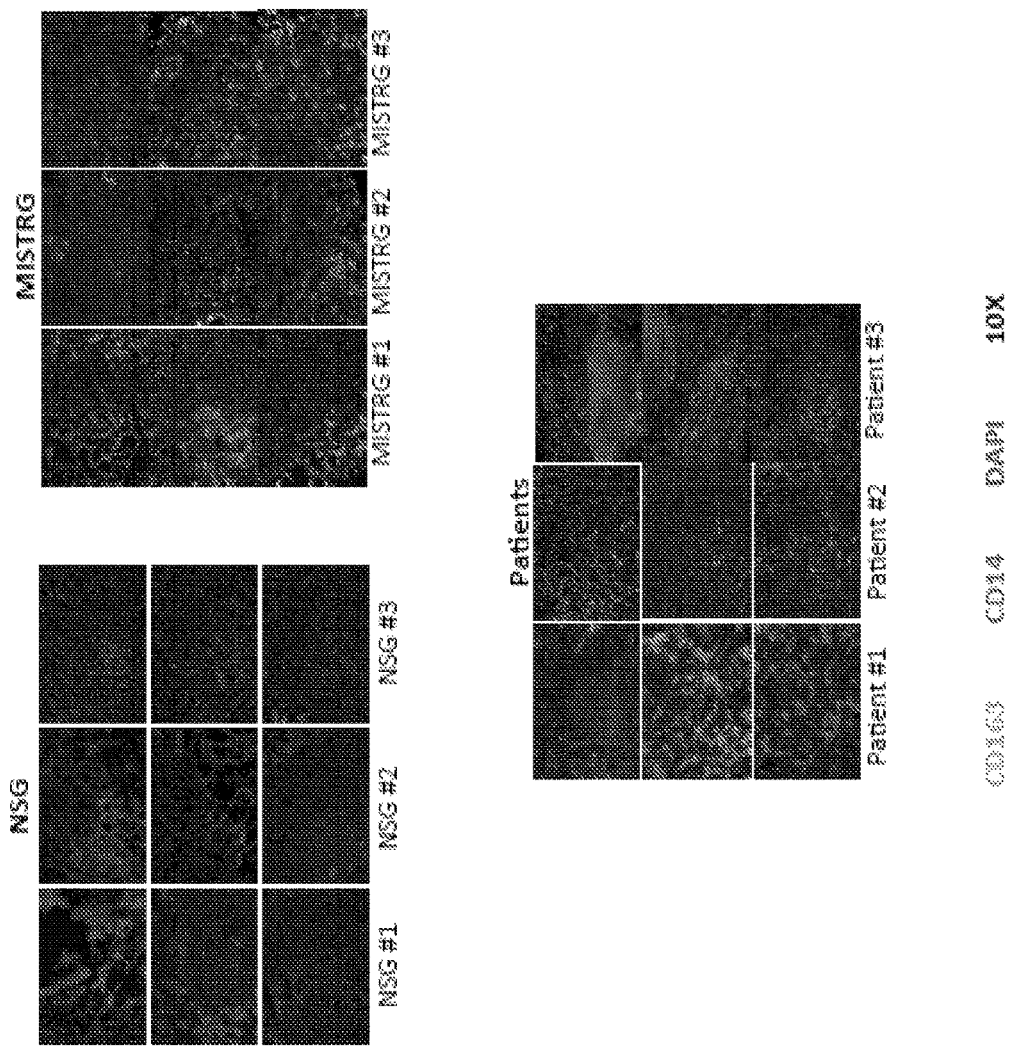
FIG. 15 depicts the results of experiments showing immunohistochemistry of human myeloid cells infiltrating melanoma. Representative immunohistochemistry staining of human myeloid cells in tumors from NSG, MISTRG or human patients. Three subject per group, and 3 pictures per subject are shown.

Next, the role of human myeloid cells in the context of a tumor microenvironment was assessed. Therefore, the human melanoma cell line Me290 was used as a tumor model (Valmori et al., 1998, Journal of immunology 160, 1750). Clinical observations show that myeloid cells infiltrate tumors in several solid tumors, and high densities of infiltrating macrophages correlate with poor patient prognosis in most types of cancer (Qian and Pollard, 2010, Cell 141, 39; Coussens et al., Science 339, 286; Egeblad et al., 2010, Developmental cell 18, 884; Nelson and Bissell, 2006, Annual review of cell and developmental biology 22, 287; Bingle et al., 2002, T Journal of pathology 196, 254). Accordingly, higher human myeloid cell infiltration was detected in tumors in MISTRG than in NSG, as shown by the expression of human PTPRC and ITGAM mRNA (encoding respectively CD45 and CD11b) (FIG. 4A). Closely resembling human tumors in patients, cells expressing the macrophage markers CD163 and CD14 were abundant in tumors in MISTRG, but were almost undetectable in the same tumors in NSG (FIGS. 4B and 4C; and FIG. 15). Most of the CD163+ cells also expressed low levels of HLA-DR and high levels of CD206 (FIGS. 4B and 4D), an immunophenotype generally associated with "M2-like" macrophages (Hao et al., 2012, Clinical & developmental immunology 2012, 948098; Tang, 2013, Cancer Lett 332, 3).

Figures 4D, 4E, 4F:
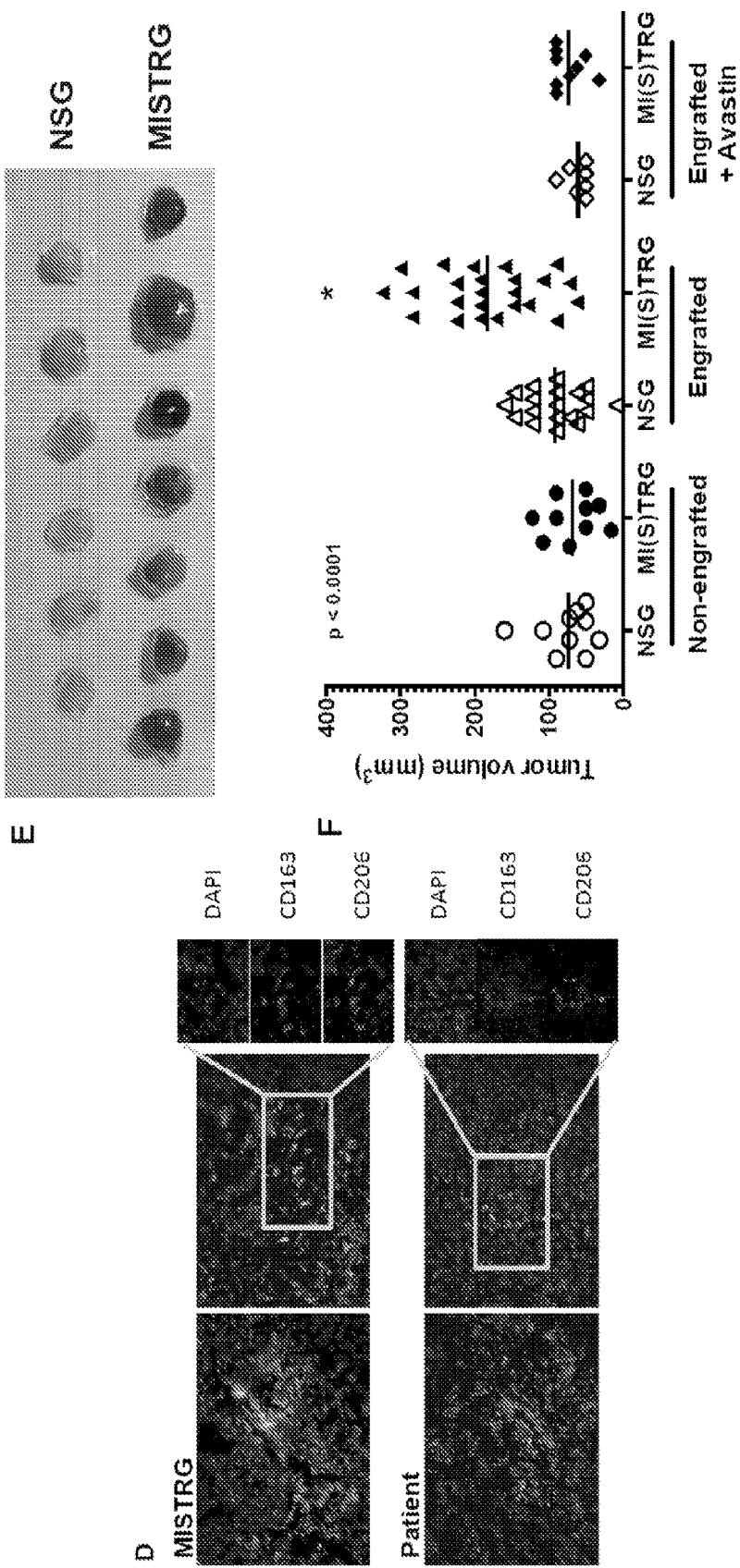

The M2 subtype of macrophages promotes tumor progression via a variety of effector mechanisms, including proliferative signals to cancer cells, anti-apoptotic signals, pro-angiogenic activity, enabling cancer cell egress from primary tumors and formation of metastasis (Qian and Pollard, 2010, Cell 141, 39; Coussens et al., Science 339, 286; Egeblad et al., 2010, Developmental cell 18, 884). Macrophage infiltration in tumors could promote tumor growth in MISTRG was assessed. Remarkably, it was observed that the size of the tumors in CD34+-engrafted MISTRG, which are heavily infiltrated by human CD163+ HLA-DRlow CD206+ macrophages, was significantly greater than tumors in NSG, which are not infiltrated by human macrophages and are the same small size seen in non-engrafted NSG or MISTRG mice (FIGS. 4E and 4F). One of the mechanisms by which macrophages support tumor growth is through the production of cytokines or enzymes that promote vascularization and immune suppression. VEGF is an important polyfunctional tumor-supporting molecule (Kandalaft et al., Current topics in microbiology and immunology 344, 129; Motz and Coukos, Immunity 39, 61), and to test whether this factor was involved in tumor growth in MISTRG, the mice were treated with the human-VEGF inhibitor Avastin™. This treatment completely reversed the tumor-growth phenotype (FIG. 4F), demonstrating that myeloid cells in MISTRG support melanoma growth through a VEGF-dependent mechanism. Overall, these results show that MISTRG mice recapitulate the role of human macrophages in tumor development and fulfill a critical need for models allowing studies of the interaction between human tumors and human macrophages in vivo, especially at onset of tumor development.

The data described here have demonstrated that the provision of multiple human cytokines in MISTRG mice resulted in synergistic effects (FIG. 16) on human hematopoiesis and on direct or indirect support for human immune cell function. The MISTRG model of HHLS mice offers a unique opportunity to study human innate immune responses in vivo.

The materials and methods are now described.

Mouse Strains

The generation of mice with knockin replacement of the genes encoding TPO, IL-3/GM-CSF and M-CSF or with BAC-transgenic expression of human SIRPα in the RAG2−/−γc−/− Balb/c x 129 genetic background was reported (Rathinam et al., 2011, Blood 118, 3119; Willinger et al., 2011, Proceedings of the National Academy of Sciences 108, 2390; Rongvaux et al., 2011, Proceedings of the National Academy of Sciences 108, 2378; Strowig et al., 2011, Proceedings of the National Academy of Sciences 108, 13218). These strains were crossbred to obtain MITRG (M-CSFh/hIL-3/GM-CSFh/hTPOh/hRAG2−/−γc−/−) and MISTRG (M-CSFh/hIL-3/GM-CSFh/hhSIRPAtgTPOh/hRAG2−/−γc−/−) mice. Those mice are viable, healthy and fertile. The mice were maintained under specific pathogen free conditions with continuous treatment with enrofloxacin in the drinking water (Baytril, 0.27 mg/ml). NOD Scid γc−/−(NSG) mice were obtained from Jackson Laboratory.

Human HSPC Preparation and Engraftment into Recipient Mice

Recipient mice were engrafted with human hematopoietic stem and progenitor cells as described (Rathinam et al., 2011, Blood 118, 3119; Willinger et al., 2011, Proceedings of the National Academy of Sciences 108, 2390; Rongvaux et al., 2011, Proceedings of the National Academy of Sciences 108, 2378; Traggiai et al., 2004, Science 304, 104; Strowig et al., 2011, Proceedings of the National Academy of Sciences 108, 13218). Fetal liver samples were cut in small fragments, treated for 45 min at 37° C. with Collagenase D (Roche, 100 ng/mL) and a cell suspension was prepared. Human CD34+ cells were purified by density gradient centrifugation (Lymphocyte Separation Medium, MP Biomedicals) followed by positive immunomagnetic selection with anti-human CD34 microbeads (Miltenyi Biotec). Cells were frozen in FBS containing 10% DMSO and kept in liquid nitrogen.

For engraftment, newborn pups (within first 2 days of life) were sublethally irradiated (X-ray irradiation; RG, 2×180 cGy 4 h apart; NSG, 1×100 cGy; MISTRG, 1×150 cGy) and 100,000 FL-CD34+ cells in 20 μL of PBS were injected into the liver with a 22-gauge needle (Hamilton Company). In specific experiments (FIGS. 1D and 1E), 200,000-300,000 cells were injected into non-irradiated MISTRG newborn recipients. The mice were bled 7-9 weeks later and the percentage of human CD45+ cells was measured by flow cytometry. Mice in which human CD45+ cells represented at least 5% (RG) or 10% (NSG, MITRG and MISTRG) of the total (mouse and human combined) CD45+ populations were selected for further experimentation. The mice were sacrificed or used for experiments 9-12 weeks after transplantation.

All experiments were performed in compliance with Yale University Human Investigation Committee and Yale Institutional Animal Care and Use Committee protocols.

Immunophenotypic Analysis of Human Cell Populations

To prepare WBCs, heparinized blood was treated twice with ACK lysis buffer to eliminate RBCs. Single cell suspension of the spleen and bone marrow (flushed from the femur and tibia) were treated with ACK lysis buffer. Liver and lung leukocytes were isolated by mechanically dissociating and digesting tissues with 100 U/ml collagenase IV and 0.02 mg/ml DNase I (Sigma) for 1 h at 37° C., followed by density gradient centrifugation.

For FACS analysis, antibodies against the following antigens were used:

Mouse antigens: CD45 (clone 30-F11), CD71 (RI7217), Ter119

Human antigens: CD1c (BDCA1, clone L161), CD3 (UCHT1), CD11b (ICRF44), CD11c (3.9), CD14 (M5E2), CD16 (3G8), CD19 (HIB19), CD33 (WM53), CD45 (H130), CD62L (DREG-56), CD66 (ASL-32), CD94 (DX22), CD107a (H4A3), CD115 (9-4D2-1E4), CD123 (6H6), CD141 (BDCA3, M80), CD161 (HP-3G10), CD235a (HI264), CD303 (BDCA2, 201A), NKp46 (9E2), IL-15Rα (JM7A4), CX3CR1 (2A9-1), HLA-A,B,C (W6/32), HLA-DR (L243), IFNγ (B27) KIR2DL1/S1 (HP-MA4), KIR2DL2/L3 (DX27), KIR3DL1 (DX9), perforin (dG9).

Human lineage cocktail: CD3, CD15, CD19, CD56, NKp46

All antibodies were obtained from Biolegend, BD Biosciences or Miltenyi Biotec. Data were acquired with FACSDiva on a LSRII flow cytometer (BD Biosciences) and analyzed with FlowJo software.

For histological analysis, spleen, lung, liver and colon tissues were fixed overnight in IHC zinc fixative (BD Biosciences) or 4% paraformaldehyde and embedded in paraffin. Sections were stained with hematoxylin and eosin, or with anti-human CD68 antibody (clone PGM1) followed by a HRP-conjugated secondary antibody and revealed with the peroxidase substrate 3, 3'-diaminobenzidine.

Phagocytosis Assay in vitro

*E. Coli* expressing GFP were grown in LB medium overnight at 37° C. to an OD600 of 1.5-1.8, at which point the bacteria were diluted and grown for 1-2 hours to an OD600 of approximately 1.0. The *E. coli* were washed three times with PBS and incubated with WBCs from MITRG mice for 4 hours at 37° C. in a volume of 200 µl with about $2\times10^8$ *E. coli* per $1\times10^7$ WBCs. After the incubation, the cells were washed with PBS and analyzed by flow cytometry.

TLR Stimulation in vitro and Infection in vivo

Human monocyte subsets were isolated from the BM of mice. Briefly, BM cells were recovered and pooled from the hind legs and the spine of six mice. Human CD33+ cells were enriched by magnetic isolation (EasySep CD33 selection kit, StemCell Technologies). CD14+CD16− and CD14+CD16+ subsets were purified on a FACSAria cell sorter (BD Biosciences). 100,000 cells in 200 µl media were cultivated overnight in the presence of the TLR4 ligand LPS (*E. Coli* 0111:B4, Sigma-Aldrich, 100 ng/ml) or the TLR7/8 ligand R848 (Invivogen, 10 µg/ml).

For in vivo stimulation, 35 µg of LPS (*E. coli* 0111:B4, Sigma-Aldrich) in 100 µl PBS were injected intra-peritoneally and the serum was collected 90 minutes later.

Mice were infected with $3\times10^3$ colony-forming units (CFU) of Listeria monocytogenes (strain 10403S) by intravenous injection. Forty-eight hours after infection, sera and tissues were harvested for ELISA and qPCR, respectively. Liver lymphocytes from uninfected or infected mice were incubated at 37C°/5% $CO_2$ for 4 hours in medium containing monensin (GolgiStop, BD Biosciences) and anti-human CD107a antibody. Cells were then stained for surface antigens, permeabilized using Cytofix/Cytoperm kit (BD Biosciences), and stained for intracellular human IFNγ.

Mice were infected intranasally with $2\times10^4$ PFU of influenza A/PR8 (H1N1) virus, and lungs were harvested on day 3 postinfection for qPCR analysis.

Cytokine concentrations (human TNFα, IL-6 and IL-1β) in mouse serum and in culture supernatants were measured using ELISA MAX Standard kits (Biolegend), following the manufacturer's instructions.

RBC Analysis

RBC counts were measured on a Hemavet 950 (Drew Scientific). Blood smears were stained with Wright-Giemsa. For mouse RBC transfer experiments, blood was obtained from RG mice, labeled with CFSE (20 µM, 15 minutes at 37° C.), washed three times with PBS and 200 µl of labeled RBCs were injected by retro-orbital intravenous injection. The mice were bled 5 minutes later to determine the initial frequency (Day 0, 100%) of CFSE-positive cells among Ter119+ cells by flow cytometry. They were then bled at the indicated time points and the maintenance of CFSE-labeled Ter119+ cells was calculated as a percentage of Day 0 values.

Depletion of Phagocytic Cells in vivo

Phagocytic cells were depleted by intravenous retro-orbital injection of 100 µl of clodronate-loaded liposomes (Van Rooijen and Sanders, 1994, Journal of immunological methods 174, 83). Clodronate-liposomes were injected 3 times daily and human NK cells in mouse liver were analyzed 24 h after the last injection. For RBC phagocytosis assay, clodronate-liposomes were injected 3 days and 1 day prior to transfer of CFSE-labeled RBCs.

Quantitative RT-PCR

Total RNA was extracted from tissues or purified cells with TRIzol reagent (Invitrogen) according to the manufacturer's instructions and used for cDNA synthesis with the SuperScript First-Strand Synthesis System (Invitrogen). Quantitative RT-PCR was performed on a 7500 Fast Real-Time PCR system with primer-probe sets purchased from ABI. Expression values were calculated using the comparative threshold cycle method and normalized to mouse Hprt or human HPRT, as indicated.

In vivo NK Cell Cytotoxicity Assays

Human NK cell cytotoxicity in vivo was determined following a previously reported protocol (Strowig et al., 2010, Blood 116, 4158). LCL721.221 (HLA class I negative) and LCL721.45 (class I positive) cells were mixed in a 1:1 ratio, labeled with CellTrace Violet (Invitrogen) and injected intravenously ($1\times10^7$ cells/mouse) into engrafted NSG or MISTRG mice. Mice were sacrificed 12 hours later and single cell suspension of the spleens were prepared and analyzed by flow cytometry. The proportions of HLA class I positive and negative among violet cells were measured and specific lysis was calculated as (MHC class I positive−MHC class I negative)×100/MHC class I positive.

Tumorigenesis

The human melanoma cell line Me290 (Valmori et al., 1998, Journal of immunology 160, 1750) was grown to ~90% confluency and the cells (~7 million cells per mouse) were injected subcutaneously under anesthesia in the flank of the mouse. For some experiments, the mice were treated every other day, starting on the day of tumor implantation, with the anti-human VEGF antibody Avastin™ (Roche; 100 µg intravenously). The size of the tumors was measured 11 days later and the volume calculated using the following formula: Volume=0.5*Length2*Width.

Patients and mouse tissues were frozen in Optimum Cutting Temperature (OCT, Sakura Finetek). Cryosections (7 µm) were consecutively treated with Triton-100X 0.1% for 15 min, Hyaluronidase 0.03% for 15 min, Background Buster (Innovex bioscience) for 15 min, Fc Receptor Block (Innovex bioscience) for 15 min and Background Buster for an additional 15 min. The sections were then stained with primary antibodies, diluted in PBS supplemented with 5% BSA and 0.01% Saponin for 1 h at room temperature, washed and stained with the secondary antibodies at room temperature for 40 minutes. Nuclei were stained with 4',6-diamidino -2-phenylindole (1 µg/mL) for 2 min.

Primary antibodies: human CD14 (1:200, UCHM1, AbD Serotec); human CD163 (1:200, EDHu-1, AbD Serotec); human CD206 (1:100, 15-2, AbD Serotec); human HLA-DR (1:100, LN3, Biolegend). For CD163/CD206 combined staining, both antibodies were labeled with Alexa Fluor 488 or 568 Antibody Labeling Kit (Molecular Probes) prior tissue staining.

Secondary antibodies: goat anti-rat Alexa Fluor 568; goat anti-mouse Alexa Fluor 488; goat anti-mouse Alexa Fluor 588 or goat anti-mouse Alexa Fluor 647 (1:700, Molecular Probes).

Immunofluorescence imaging was performed on an Eclipse Ti inverted microscope system (Nikon Instruments Inc.) operated via NIS-Element Ar software (Nikon Instruments Inc).

For quantification of the density of CD163+ cell infiltration, tumors from 3 different melanoma patients, 3 NSG and 3 MISTRG were selected. From each tumor, 3 cryosections were stained for human CD163. From each stained section 3 representative pictures were acquired, totaling 27 representative pictures from each group (Patients, MISTRG and NSG). For each picture, CD163+ cells were counted using the NIS-Element Ar software (Niko Instruments Inc.). Each picture was analyzed using the "split channels+overlay" display and by zooming simultaneously on each separate channel and on the overlay.

Statistical Analysis

Statistical analysis was performed with the GraphPad Prism 5 software, using one-way ANOVA followed by Tukey post hoc test, two-tailed unpaired Student's t-test or repeated measure ANOVA.

Example 2

Human Myeloid Neoplasms can be Engrafted in MISTRG

Myeloid leukemia is a form of cancer that affects cells of the myeloid lineage. Myeloid leukemias are classified in different types, including acute myeloid leukemia (AML), myeloproliferative disorder (MPD), chronic myelo-monocytic leukemia (CMML) and myelodysplastic syndrome (MDS). The risk of developing myeloid leukemias increases with age and the incidence of these diseases is likely to increase with ageing of the population. Although therapeutic and supportive care approaches are available in the clinic, a better understanding of this group of diseases and novel therapies are needed.

One of the methods used to study human leukemias relies on the xeno-transplantation of patient samples into immunodeficient mice. However, currently available recipient mice are not optimal for this purpose: only a subset of AML samples can be engrafted successfully; and robust engraftment of MPD, CMML or MDS (including RCUD, RAEB I and RAEB II) has not been reported so far. Thus, optimized strains of recipient mice are needed for better engraftment of human myeloid leukemia.

It is demonstrated herein that MISTRG supports better engraftment of human hematopoietic cells, leading to the almost complete replacement of mouse hematopoiesis by human hematopoiesis in the bone marrow. It is also shown herein that samples isolated from patients with AML, CMML and MDS can be engrafted in MISTRG (FIG. 17).

Therefore, the genetically modified non-human animals described herein represent a novel in vivo animal model of human myeloid leukemia that will be useful to (i) study the cellular and molecular pathogenesis of the disease; (ii) to identify biomarkers with predictive or prognostic value; (iii) to identify novel targets for therapies; and (iv) to test therapies in a pre-clinical and patient-specific setting.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of transplanting human cancer cells, comprising:
   transplanting human cancer cells into a genetically modified, immunodeficient mouse; and
   transplanting human hematopoietic cells into the genetically modified, immunodeficient mouse,
   wherein the genetically modified, immunodeficient mouse comprises in its genome a recombination activating gene 2 (Rag-2) gene knock-out, an IL2 receptor gamma chain (IL2 rg) gene knock-out, a replacement of a mouse M-CSF gene with a nucleic acid encoding a human M-CSF polypeptide at a mouse M-CSF gene locus, a replacement of a mouse IL-3 gene with a nucleic acid encoding a human IL-3 polypeptide at a mouse IL-3 gene locus, a replacement of a mouse GM-CSF gene with a nucleic acid encoding a human GM-CSF polypeptide at a mouse GM-CSF gene locus, an insertion of a nucleic acid encoding a human SIRPA polypeptide, and a replacement of a mouse TPO gene with a nucleic acid encoding a human TPO polypeptide at a mouse TPO gene locus, wherein each of the nucleic acids encoding the human M-CSF polypeptide, the human IL-3 polypeptide, the human GM-CSF polypeptide, the human SIRPA polypeptide, and the human TPO polypeptide is operably linked to a promoter, and wherein the mouse expresses the human M-CSF polypeptide, the human IL-3 polypeptide, the human GM-CSF polypeptide, the human SIRPA polypeptide, and the human TPO polypeptide.

2. The method of claim 1, wherein the human cancer cells are primary human cancer cells isolated from a patient.

3. The method of claim 2, wherein the human cancer cells and the human hematopoietic cells are isolated from the same patient.

4. The method of claim 1, wherein the human cancer cells are from a cancer cell line.

5. The method of claim 1, wherein the human cancer cells are selected from leukemia cells, breast cancer cells, lung cancer cells, and melanoma cells.

6. The method of claim 5, wherein the human cancer cells are leukemia cells.

7. The method of claim 5, wherein the human cancer cells are melanoma cells.

8. The method of claim 1, wherein the human hematopoietic cells comprise CD34+cells.

9. The method of claim 1, wherein the human SIRPA polypeptide is a biologically active fragment of a full-length human SIRPA polypeptide.

10. A method of human hematopoietic cell engraftment, comprising:
    administering at least one human hematopoietic cell to a genetically modified, immunodeficient mouse, wherein the genetically modified, immunodeficient mouse comprises in its genome a recombination activating gene 2 (Rag-2) gene knock-out, an IL2 receptor gamma chain (IL2 rg) gene knock-out, a replacement of a mouse M-CSF gene with a nucleic acid encoding a human M-CSF polypeptide at a mouse M-CSF gene locus, a replacement of a mouse IL-3 gene with a nucleic acid encoding a human IL-3 polypeptide at a mouse IL-3 gene locus, a replacement of a mouse GM-CSF gene with a nucleic acid encoding a human GM-CSF polypeptide at a mouse GM-CSF gene locus, an insertion of a nucleic acid encoding a human SIRPA polypeptide, and a replacement of a mouse TPO gene with a nucleic acid encoding a human TPO polypeptide at a mouse TPO gene locus, wherein each of the nucleic acids encoding the human M-CSF polypeptide, the human IL-3 polypeptide, the human GM-CSF polypeptide, the human SIRPA polypeptide, and the human TPO polypeptide is operably linked to a promoter, and wherein the mouse expresses the human M-CSF polypeptide, the human IL-3 polypeptide, the human GM-CSF polypeptide, the human SIRPA polypeptide, and the human TPO polypeptide, and wherein the method does not comprise sub-lethally irradiating the genetically modified, immunodeficient mouse or treating the genetically modified, immunodeficient mouse with a radiomimetic drug prior to the administering.

11. The method of claim 10, wherein the human SIRPA polypeptide is a biologically active fragment of a full-length human SIRPA polypeptide.

12. The method of claim 10, wherein the human hematopoietic cells comprise CD34+cells.

* * * * *